(12) United States Patent
Matthews

(10) Patent No.: US 8,748,478 B2
(45) Date of Patent: *Jun. 10, 2014

(54) SULFAMIDES AS TRPM8 MODULATORS

(71) Applicant: Janssen Pharmaceutica, NV, Beerse (BE)

(72) Inventor: Jay M Matthews, Lansdale, PA (US)

(73) Assignee: Janssen Pharmaceutica, NV (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/851,988

(22) Filed: Mar. 28, 2013

(65) Prior Publication Data

US 2013/0237547 A1 Sep. 12, 2013

Related U.S. Application Data

(62) Division of application No. 12/638,506, filed on Dec. 15, 2009, now Pat. No. 8,436,041.

(60) Provisional application No. 61/138,598, filed on Dec. 18, 2008.

(51) Int. Cl.
*C07D 333/66* (2006.01)
*A61K 31/381* (2006.01)

(52) U.S. Cl.
USPC .............. 514/443; 514/438; 514/447; 549/57

(58) Field of Classification Search
USPC ............................ 514/443, 438, 447; 549/57
See application file for complete search history.

(56) References Cited

U.S. PATENT DOCUMENTS

| | | | |
|---|---|---|---|
| 3,828,070 A | 8/1974 | Naito | |
| 2007/0191452 A1* | 8/2007 | Smith-Swintosky | 514/397 |

FOREIGN PATENT DOCUMENTS

| | | |
|---|---|---|
| EP | 1911753 A | 4/2007 |
| WO | WO 99/28306 | 6/1999 |
| WO | WO 2006/040136 A1 | 4/2006 |
| WO | WO 2007/013691 A | 2/2007 |
| WO | WO 2007/017092 A1 | 2/2007 |
| WO | WO 2007/017093 A1 | 2/2007 |
| WO | WO 2007/017094 A | 2/2007 |
| WO | WO 2007/134107 A2 | 11/2007 |
| WO | WO 2009/012430 A1 | 1/2009 |

OTHER PUBLICATIONS

Beers, S.A., et al., "N-(5-Substituted) Thiophene-2-Alkylsulfonamides as Potent Inhibitors of 5-Lipoxygenase" Bioorganic & Medicinal Chemistry, vol. 5, No. 4, Jan. 1, 1997, pp. 779-786, XP001085465, ISSN: 0968-0896, introduction; compounds 4m, 4t, 4aa, table I.

Casy, Alan F., et al. "Opioid Analgesics, Chemistry and receptors", Plenum Press. 1986, pp. 229-249.

Cheruku, Srinivasa R., et al. "Carbon Isosteres of the 4-Aminopyridine Substructure of Chloroquine: Effects on pK a, Hematin Binding, Inhibition of Hemozoin Formation, and Parasite Growth", J. Med. Chem. 2003, 46, pp. 3166-3169.

Childers, W.E., et al., "Advances in the Development of Novel Analgesics" Expert Opinion on Therapeutic Patents, Informa Healthcare, GB LNKD-DOI:10.1517/13543776.18.9.1027, vol. 18, No. 9, Sep. 1, 2008, pp. 1027-1067, XP002556736, ISSN: 1354-3776, figures 7,13.

Dorwald, F. Zaragoza. Side Reactions in Organic Synthesis: A Guide to Successful Synthesis Design, Weinheim: Wiley-VCH Verlag GmbH & Co. KGaA, 2005, Preface.

Jordan, V. C. Nature Reviews: Drug Discovery, 2, 2003, pp. 205-213.

Patani et al. Chem. Rev. 1996,96,3147-3176.

Sheridan, R.P. J. Chem. Inf. Comput. Sci. 2002, 42, 103-108.

Souillac, et al., Characterization of Delivery Systems, Differential Scanning Calorimetry, pp. 217-218 (in Encyclopedia of Controlled Drug Delivery, 1999, John Wiley & Sons, pp. 212-227).

Vippagunta et al. Advanced Drug Delivery Reviews, 48 (2001), pp. 3-26.

PCT International Search Report and Written Opinion, PCT/2009/068034, dated May 7, 2010, 17 pages.

State Intellectual Property of Office of People'S Republic China Search Report, dated May 27, 2013, 3 pages.

* cited by examiner

*Primary Examiner* — Sreeni Padmanabhan
*Assistant Examiner* — Irina Neagu

(57) ABSTRACT

Disclosed are compounds, compositions and methods for treating various diseases, syndromes, conditions and disorders, including pain. Such compounds are represented by Formula I as follows:

(I)

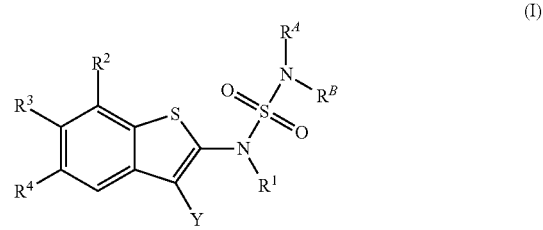

wherein Y, $R^1$, $R^2$, $R^3$, $R^4$, $R^A$, and $R^B$ are defined herein.

8 Claims, No Drawings

US 8,748,478 B2

SULFAMIDES AS TRPM8 MODULATORS

CROSS-REFERENCE TO RELATED APPLICATIONS

The present application is a divisional application of U.S. application Ser. No. 12/638,506, filed on Dec. 15, 2009 which claims the benefit of the filing of U.S. Provisional Application No. 61/138,598, filed on Dec. 18, 2008. The complete disclosures of the aforementioned related patent applications are hereby incorporated herein by reference for all purposes.

FIELD OF THE INVENTION

The present invention relates to sulfamides that act as modulators of the TRPM8 receptor. The present invention also relates to processes for the preparation of sulfamides and to their use in treating various diseases, syndromes, and disorders, including those that cause inflammatory or neuropathic pain, cold intolerance or cold allodynia, peripheral vascular pain, itch, urinary incontinence, chronic obstructive pulmonary disease (COPD), pulmonary hypertension and anxiety, including other stress-related disorders, and combinations thereof.

BACKGROUND OF THE INVENTION

Transient receptor potential (TRP) channels are non-selective cation channels that are activated by a variety of stimuli. Numerous members of the ion channel family have been identified to date, including the cold-menthol receptor, also called TRPM8 (McKemy D. D., et al., *Nature* 2002, 416 (6876), 52-58). Collectively, the TRP channels and related TRP-like receptors connote sensory responsivity to the entire continuum of thermal exposure, selectively responding to threshold temperatures ranging from noxious hot to noxious cold, as well as to certain chemicals that mimic these sensations. Specifically, TRPM8 may be stimulated by cool to cold temperatures as well as by chemical agents such as menthol and icilin, which may be responsible for the therapeutic cooling sensation that these agents provoke.

TRPM8 is located on primary nociceptive neurons (A-delta and C-fibers) and is also modulated by inflammation-mediated second messenger signals (Abe, J., et al., *Neurosci Lett* 2006, 397(1-2), 140-144; Premkumar, L. S., et al., *J. Neurosci*, 2005, 25(49), 11322-11329). The localization of TRPM8 on both A-delta and C-fibers may provide a basis for abnormal cold sensitivity in pathologic conditions wherein these neurons are altered, resulting in pain, often of a burning nature (Kobayashi, K., et al., *J Comp Neurol*, 2005, 493(4), 596-606; Roza, C., et al., *Pain,* 2006, 120(1-2), 24-35; and Xing, H., et al., *J Neurophysiol,* 2006, 95(2), 1221-30). Cold intolerance and paradoxical burning sensations induced by chemical or thermal cooling closely parallel symptoms seen in a wide range of clinical disorders and thus provide a strong rationale for the development of TRPM8 modulators as novel antihyperalgesic or antiallodynic agents. TRPM8 is also known to be expressed in the brain, lung, bladder, gastrointestinal tract, blood vessels, prostate and immune cells, thereby providing the possibility for therapeutic modulation in a wide range of maladies.

International patent application WO 2006/040136 A1 from Bayer Healthcare AG purportedly describes substituted 4-benzyloxy-phenylmethylamide derivatives as cold menthol receptor-1 (CMR-1) antagonists for the treatment of urological disorders. International patent application WO 2006/040103 A1 from Bayer Healthcare AG purportedly describes methods and pharmaceutical compositions for treatment and/or prophylaxis of respiratory diseases or disorders. International patent applications WO 2007/017092A1, WO 2007/017093A1 and WO 2007/017094A1, from Bayer Healthcare AG, purportedly describe benzyloxyphenylmethyl carbamate, substituted 2-benzyloxybenzoic acid amide and substituted 4-benzyloxybenzoic acid amide derivatives for the treatment of diseases associated with the cold menthol receptor (CMR), a.k.a. TRPM8.

There is a need in the art for TRPM8 antagonists that can be used to treat a disease, syndrome, or condition in a mammal in which the disease, syndrome, or condition is affected by the modulation of TRPM8 receptors, such as pain, the diseases that lead to such pain, and pulmonary or vascular dysfunction.

SUMMARY OF THE INVENTION

The present invention provides, inter alia, compounds of Formula (I)

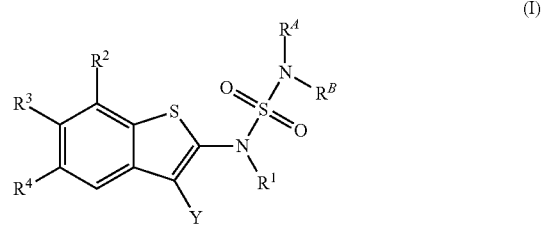

wherein
Y is
(i) H;
(ii) bromo;
(iii) chloro;
(iv) fluoro;
(v) iodo;
(vi) $C_{3-6}$ cycloalkyl; or
(vii) $C_{1-6}$ alkyl;
$R^1$ is
(i) $C_{3-6}$ cycloalkyl;
(ii) $C_{1-6}$ alkyl substituted with one $C_{6-10}$ aryl group and optionally one additional substituent selected from the group consisting of hydroxy and oxo, wherein said $C_{6-10}$ aryl group is optionally substituted with 1 to 3 substituents independently selected from the group consisting of chloro, fluoro, bromo, $C_{1-4}$ alkyl, $C_{1-4}$ alkoxy optionally substituted with 1 to 3 fluoro substituents, hydroxy, $C_{1-4}$ alkoxycarbonyl, $C_{1-3}$ alkylthio, trifluoromethylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, and $C_{1-3}$ alkylcarbonyl; with the proviso that not more than two of the substituents are selected from the group consisting of $C_{1-4}$ alkoxy substituted with 1 to 3 fluoro substituents, $C_{1-4}$ alkoxycarbonyl, $C_{1-3}$ alkylthio, trifluoromethylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, and $C_{1-3}$ alkylcarbonyl;
(iii) $C_{1-6}$ alkyl substituted with phenyl, wherein phenyl is substituted with 4 or 5 fluoro substituents; or phenyl is substituted with methoxy and 3 to 4 fluoro substituents;

(iv) $C_{1-6}$ alkyl optionally substituted with $C_{3-6}$cycloalkyl or trifluoromethyl; or (v) methylene substituted with benzo[1,3]dioxol-5-yl, 2,2-difluoro-benzo[1,3]dioxol-5-yl, or 2,3-dihydro-benzo[1,4]dioxin-6-yl;

$R^2$ is
(i) hydrogen,
(ii) fluoro,
(iii) chloro,
(iv) methoxy, or
(v) methyl;

$R^3$ is
(i) hydrogen,
(ii) fluoro,
(iii) chloro, or
(iv) methyl;

$R^4$ is
(i) hydrogen,
(ii) $C_{1-6}$ alkyl,
(iii) trifluoromethyl,
(iv) $C_{1-4}$ alkoxy,
(v) bromo,
(vi) chloro,
(vii) fluoro, or
(viii) hydroxy;

$R^A$ is $C_{1-6}$ alkyl substituted at a terminal carbon atom with a substituent selected from the group consisting of carboxy, $C_{1-4}$ alkoxycarbonyl, $C_{1-3}$alkoxy, and hydroxy;

$R^B$ is hydrogen or $C_{1-6}$alkyl;

or, $R^A$ and $R^B$ are taken together with the nitrogen atom to which they are attached to form a 6 membered ring containing one heteroatom selected from the group consisting of O, S, and $S(O_2)$;

or, $R^A$ and $R^B$ are taken together with the nitrogen atom to which they are attached to form a 5 or 6 membered ring, optionally containing one additional N atom, to form (i) piperizin-1-yl wherein the piperizinyl nitrogen is substituted with $R^C$;

(ii) pyrrolidin-1-yl optionally substituted at the 3-position with $NR^DR^E$; wherein $R^D$ and $R^E$ are independently selected from the group consisting of hydrogen and $C_{1-4}$alkyl; or, $R^D$ and $R^E$ are taken together with the nitrogen atom to which they are both attached to form a 5 or 6 membered ring; or (iii) piperidin-1-yl optionally substituted with carboxy; $C_{1-3}$alkoxycarbonyl; or $C_{1-4}$alkyl substituted at a terminal carbon atom with a substituent selected from the group consisting of carboxy, $C_{1-3}$alkoxy, and hydroxy;

or piperidinyl is optionally substituted at the 4-position with (i) $C(O)NR^YR^Z$; wherein $R^Y$ is hydrogen or $C_{1-6}$alkyl; and $R^Z$ is hydrogen or $C_{1-6}$ alkyl optionally substituted with amino, $C_{1-2}$ alkylamino, or di($C_{1-2}$ alkyl)amino; or, $R^Y$ and $R^Z$ are taken together with the nitrogen atom to which they are both attached to form a 5 or 6 membered ring, and said 6 membered ring is optionally containing O or 4-N(methyl);

(ii) $NR^HR^J$; wherein $R^H$ and $R^J$ are independently selected from the group consisting of hydrogen and $C_{1-4}$alkyl; or, $R^H$ and $R^J$ are taken together with the nitrogen atom to which they are both attached to form a 5 or 6 membered ring; or (iii) a spirofused pyrrolidinyl ring bound via a carbon atom of said ring, wherein the pyrrolidinyl nitrogen atom is optionally substituted with $C_{1-4}$alkyl, $C_{3-6}$cycloalkyl($C_{1-3}$)alkyl, or $CH_2CF_3$;

and wherein a piperidinyl ring is optionally benzofused to form a 1,2,3,4-tetrahydro-isoquinolin-1-yl, wherein said 1,2,3,4-tetrahydro-isoquinolin-1-yl is optionally substituted on the heterocyclyl portion of said ring with one to two substituents independently selected from the group consisting of methyl and fluoro;

or, the heterocyclyl portion of said 1,2,3,4-tetrahydro-isoquinolin-1-yl is unsubstituted and the benzo portion of said ring is optionally substituted with one to two substituents independently selected from the group consisting of fluoro, chloro, bromo, iodo, methyl, trifluoromethyl, cyano, ethoxycarbonyl, carboxy, and methoxy; provided that no more than one of the substituents is carboxy or ethoxycarbonyl;

$R^C$ is
(i) hydrogen;
(ii) $C_{1-8}$ alkyl;
(iii) $C_{3-6}$cycloalkyl;
(iv) $C_{3-6}$cycloalkyl($C_{1-4}$)alkyl;
(v) $CH_2CF_3$;
(vi) phenyl optionally independently substituted with one to two substituents selected from the group consisting of methyl, methoxy, chloro, fluoro, and trifluoromethyl;
(vii) $C(O)R^{1a}$ wherein $R^{1a}$ is $C_{1-6}$alkyl, $C_{3-6}$cycloalkyl, or phenyl; or
(viii) $SO_2R^{2a}$ wherein $R^{2a}$ is methyl or phenyl;

and enantiomers, diastereomers, solvates, and pharmaceutically acceptable salts thereof.

The present invention also provides, inter alia, a pharmaceutical composition comprising, consisting of and/or consisting essentially of a pharmaceutically acceptable carrier, a pharmaceutically acceptable excipient, and/or a pharmaceutically acceptable diluent and a compound of Formula (I) or a pharmaceutically acceptable salt form thereof.

Also provided are processes for making a pharmaceutical composition comprising, consisting of, and/or consisting essentially of admixing a compound of Formula (I) and a pharmaceutically acceptable carrier, a pharmaceutically acceptable excipient, and/or a pharmaceutically acceptable diluent.

The present invention further provides, inter alia, methods for treating or ameliorating a TRPM8-modulated disorder in a subject, including a mammal and/or human in which the disease, syndrome, or condition is affected by the modulation of TRPM8 receptors, such as pain, the diseases that lead to such pain, and pulmonary or vascular dysfunction using a compound of Formula (I). In particular, the methods of the present invention are directed to treating or ameliorating a TRPM8 receptor-modulated disorder including inflammatory pain, cold-intolerance or cold allodynia, peripheral vascular pain, itch, urinary incontinence, chronic obstructive pulmonary disease, pulmonary hypertension and anxiety, including other stress-related disorders, using a compound of Formula (I).

The present invention also provides, inter alia, methods for producing the instant compounds and pharmaceutical compositions and medicaments thereof.

DETAILED DESCRIPTION OF THE INVENTION

The term "independently" means that when more than one of such substituent is possible, such substituents may be the same or different from each other.

The term "alkyl" whether used alone or as part of a substituent group refers to straight and branched carbon chains having 1 to 8 carbon atoms or any number within this range.

Therefore, designated numbers of carbon atoms (e.g., $C_{1-8}$) shall refer independently to the number of carbon atoms in an alkyl moiety or to the alkyl portion of a larger alkyl-containing substituent. In substituent groups with multiple alkyl groups such as ($C_{1-6}$ alkyl)$_2$amino- the $C_{1-6}$ alkyl groups of the dialkylamino may be the same or different.

The term "alkoxy" refers to an O-alkyl substituent group, wherein alkyl is as defined supra. To the extent substituted, an alkyl and alkoxy chain may be substituted on a carbon atom.

The terms "alkenyl" and "alkynyl" refer to straight and branched carbon chains having 2 or more carbon atoms, wherein an alkenyl chain has at least one double bond in the chain and an alkynyl chain has at least one triple bond in the chain.

The term "cycloalkyl" refers to saturated or partially unsaturated, monocyclic or polycyclic hydrocarbon rings of from 3 to 14 carbon atom members. Examples of such rings include, and are not limited to cyclopropyl, cyclobutyl, cyclopentyl, cyclohexyl, cycloheptyl and adamantyl. Similarly, "cycloalkenyl" refers to a cycloalkyl that contains at least one double bond in the ring. Additionally, a "benzofused cycloalkyl" is a cycloalkyl ring that is fused to a benzene ring. A "heteroaryl-fused cycloalkyl" is a cycloalkyl ring that is fused to a 5 or 6-membered heteroaryl ring (containing one of O, S or N and, optionally, one additional nitrogen).

The term "heterocyclyl" refers to a nonaromatic cyclic ring of 5 to 7 members in which 1 to 2 members are nitrogen, or a nonaromatic cyclic ring of 5 to 7 members in which zero, one or two members are nitrogen and up to two members are oxygen or sulfur; wherein, optionally, the ring contains zero to one unsaturated bonds, and, optionally, when the ring is of 6 or 7 members, it contains up to two unsaturated bonds. As used herein, "benzofused heterocyclyl" includes a 5 to 7 membered monocyclic heterocyclic ring fused to a benzene ring. As used herein, "heteroaryl-fused heterocyclyl" refers to 5 to 7 membered monocyclic heterocyclic ring fused to a 5 or 6 membered heteroaryl ring (containing one of O, S or N and, optionally, one additional nitrogen). As used herein, "cycloalkyl-fused heterocyclyl" refers to a 5 to 7 membered monocyclic heterocyclic ring fused to a 5 to 7 membered cycloalkyl or cycloalkenyl ring. Furthermore, as used herein, "heterocyclyl-fused heterocycyl" refers to a 5 to 7 membered monocyclic heterocyclic ring fused to a 5 to 7 membered heterocyclyl ring (of the same definition as above but absent the option of a further fused ring). For instant compounds of the invention, the carbon atom ring members that form the heterocyclyl ring are fully saturated. Other compounds of the invention may have a partially saturated heterocyclyl ring. As used herein, "heterocyclyl" also includes a 5 to 7 membered monocyclic heterocycle bridged to form bicyclic rings. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

The term "heteroaryl" refers to an aromatic ring of 5 or 6 members wherein the ring consists of carbon atoms and has at least one heteroatom member. Suitable heteroatoms include N, O, or S. In the case of 5 membered rings, the heteroaryl ring contains one member of N, O, or S and, in addition, may contain up to three additional nitrogen atoms In the case of 6 membered rings, the heteroaryl ring may contain from one to three nitrogen atoms. For the case wherein the 6 membered ring has three nitrogen atoms, at most two nitrogen atoms are adjacent.

Optionally, the heteroaryl ring is fused to a benzene ring to form a "benzo fused heteroaryl"; similarly, the heteroaryl ring is optionally fused to a 5 or 6 membered heteroaryl ring (containing one of O, S or N and, optionally, one additional nitrogen atom) to form a "heteroaryl-fused heteroaryl"; similarly, the heteroaryl ring is optionally fused to a 5 to 7 membered cycloalkyl ring or a 5 to 7 membered heterocyclo ring (as defined supra but absent the option of a further fused ring) to form a "cycloalkyl-fused heteroaryl". Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; examples of heteroaryl groups with the optionally fused benzene rings include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl.

The term "arylalkyl" means an alkyl group substituted with an aryl group (e.g., benzyl, phenethyl). Similarly, "arylalkoxy" indicates an alkoxy group substituted with an aryl group (e.g., benzyloxy).

The term "halogen" refers to fluorine, chlorine, bromine and iodine. Substituents that are substituted with multiple halogens are substituted in a manner that provides compounds that are stable.

Whenever the terms "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "phenyl$C_1$-$C_6$ alkylamido$C_1$-$C_6$alkyl" substituent refers to a group of the formula:

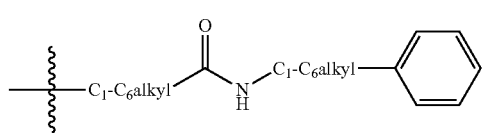

Unless otherwise noted, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "subject" as used herein, refers to an animal, preferably a mammal, most preferably a human, who has been the object of treatment, observation or experiment.

The term "therapeutically effective amount" means that amount of active compound or pharmaceutical agent that elicits the biological or medicinal response in a tissue system, animal or human that is being sought by a researcher, veterinarian, medical doctor or other clinician, which includes alleviation or partial alleviation of the symptoms of the disease, syndrome, condition or disorder being treated.

The term "composition" is intended to encompass a product comprising the specified ingredients in therapeutically effective amounts, as well as any product that results, directly or indirectly, from combinations of the specified ingredients in the specified amounts.

The term "antagonist" is used to refer to a compound capable of producing, depending on the circumstance, a functional antagonism of the TRPM8 ion channel, including, but not limited to, competitive antagonists, non-competitive antagonists, desensitizing agonists, and partial agonists.

As used herein, "inflammatory hypersensitivity" is used to refer to a condition that is characterized by one or more hallmarks of inflammation, including edema, erythema, hyperthermia and pain, and/or by an exaggerated physiologic or pathophysiologic response to one or more than one type of stimulation, including thermal, mechanical, and/or chemical stimulation.

The term "TRPM8-modulated" is used to refer to the condition of being affected by the modulation of the TRPM8 receptor, including the state of being mediated by the TRPM8 receptor.

An embodiment of the invention is a method of treating or preventing at least one of the following diseases, syndromes, and conditions selected from the group consisting of migraine, post herpetic neuralgia, post traumatic neuralgia, post chemotherapy neuralgia, complex regional pain syndrome I and II (CRPS I/II), fibromyalgia, inflammatory bowel disease, pruritis, asthma, chronic obstructive pulmonary disease, toothache, bone pain and pyresis in a subject, which method comprises, consists of, and/or consists essentially of administering to the subject, including an animal, a mammal, and a human in need of such treatment or prevention, a therapeutically effective amount of a TRPM8 antagonist that is a compound of Formula (I).

Another embodiment of the invention is a method of treating or preventing at least one of the following diseases, syndromes, and conditions selected from hypertension, peripheral vascular disease, Raynaud's disease, reperfusion injury or frostbite in a subject, which method comprises administering to the subject, including an animal, a mammal, and a human in need of such treatment or prevention a therapeutically effective amount of a TRPM8 antagonist that is a compound of Formula (I).

A further embodiment of the invention is a method of accelerating post-anesthetic recovery or post-hypothermia recovery in a subject, including an animal, a mammal, and a human, which method comprises administering to the subject, including an animal, a mammal, and a human in need of such accelerated recovery, a therapeutically effective amount of a TRPM8 antagonist that is a compound of Formula (I).

An embodiment of the present invention is directed to compounds of Formula (I).

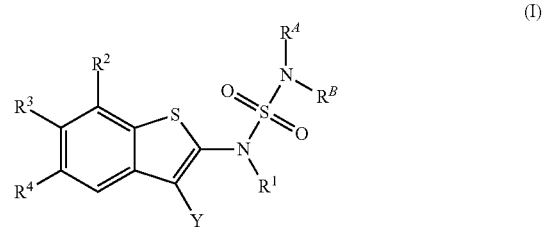

wherein
a) Y is hydrogen; bromo; chloro; fluoro; iodo; $C_{3-6}$ cycloalkyl; or $C_{1-4}$ alkyl;
b) Y is hydrogen; methyl; isopropyl; chloro; cyclopropyl; cyclobutyl; cyclopentyl; or bromo;
c) Y is hydrogen; methyl; isopropyl; chloro; cyclopropyl; or bromo;
d) $R^1$ is
   (i) $C_{3-6}$ cycloalkyl;
   (ii) $C_{1-6}$ alkyl substituted with one $C_{6-10}$ aryl group, wherein said $C_{6-10}$ aryl group is optionally substituted with 1 to 3 substituents independently selected from the group consisting of chloro, fluoro, bromo, $C_{1-4}$ alkyl, $C_{1-4}$ alkoxy, hydroxy, $C_{1-4}$ alkoxycarbonyl, $C_{1-3}$ alkylthio, trifluoromethylthio, cyano, trifluoromethyl, $C_{1-3}$ alkylsulfonyl optionally substituted with 1 to 3 fluoro substituents, nitro, and $C_{1-3}$ alkylcarbonyl; with the proviso that not more than two of the substituents are selected from the group consisting of $C_{1-4}$ alkoxy, $C_{1-4}$ alkoxycarbonyl, $C_{1-3}$ alkylthio, trifluoromethylthio, cyano, trifluoromethyl, $C_{1-3}$ alkylsulfonyl, nitro, and $C_{1-3}$ alkylcarbonyl;
   (iii) $C_{1-6}$ alkyl substituted with phenyl, wherein phenyl is substituted with 4 or 5 fluoro substituents; or phenyl is substituted with methoxy and 3 to 4 fluoro substituents; or
   (iv) $C_{1-3}$ alkyl optionally substituted with cyclopropyl or trifluoromethyl;
   (v) methylene substituted with benzo[1,3]dioxol-5-yl, 2,2-difluoro-benzo[1,3]dioxol-5-yl, or 2,3-dihydro-benzo[1,4]dioxin-6-yl;
e) $R^1$ is
   (i) $C_{1-6}$ alkyl substituted with one $C_{6-10}$ aryl group, wherein said $C_{6-10}$ aryl group is optionally substituted with 1 to 3 substituents independently selected from the group consisting of chloro, fluoro, bromo, $C_{1-4}$ alkyl, $C_{1-4}$ alkoxy, hydroxy, $C_{1-3}$ alkylthio, trifluoromethylthio, cyano, trifluoromethyl, and $C_{1-3}$ alkylcarbonyl; with the proviso that not more than two of the substituents are selected from the group consisting of $C_{1-4}$ alkoxy, $C_{1-3}$ alkylthio, trifluoromethylthio, cyano, trifluoromethyl, and $C_{1-3}$ alkylcarbonyl;
   (ii) $C_{1-3}$ alkyl substituted with phenyl, wherein phenyl is substituted with 4 or 5 fluoro substituents; or phenyl is substituted with methoxy and 3 to 4 fluoro substituents;
   (iii) $C_{1-3}$ alkyl optionally substituted with cyclopropyl or trifluoromethyl; or
   (iv) methylene substituted with benzo[1,3]dioxol-5-yl, 2,2-difluoro-benzo[1,3]dioxol-5-yl, or 2,3-dihydro-benzo[1,4]dioxin-6-yl;
f) $R^2$ is
   (i) hydrogen or
   (ii) fluoro;

g) R³ is
   (i) hydrogen or
   (ii) fluoro;
h) R⁴ is
   (i) hydrogen;
   (ii) methyl; or
   (iii) fluoro;
i) $R^A$ is $C_{1-4}$alkyl substituted at a terminal carbon atom with a substituent selected from the group consisting of carboxy, $C_{1-3}$alkoxy, and hydroxy;
j) $R^B$ is hydrogen or $C_{1-4}$alkyl;
   or, $R^A$ and $R^B$ are taken together with the nitrogen atom to which they are attached to form a 6 membered ring containing one heteroatom selected from the group consisting of O, S, and $S(O_2)$;
   or, $R^A$ and $R^B$ are taken together with the nitrogen atom to which they are attached to form a 5 or 6 membered ring, optionally containing one additional N atom, to form
      (i) piperizin-1-yl wherein the piperizinyl nitrogen is substituted with $R^C$;
      (ii) pyrrolidin-1-yl optionally substituted at the 3-position with $C_{1-4}$alkyl or $NR^DR^E$; wherein $R^D$ and $R^E$ are independently selected from the group consisting of hydrogen and $C_{1-4}$alkyl; or, $R^D$ and $R^E$ are taken together with the nitrogen atom to which they are both attached to form a 5 or 6 membered ring; or
      (iii) piperidin-1-yl optionally substituted with carboxy; $C_{1-3}$alkoxycarbonyl; or $C_{1-4}$alkyl substituted at a terminal carbon atom with a substituent selected from the group consisting of carboxy, $C_{1-3}$alkoxy, and hydroxy;
      or piperidinyl is optionally substituted at the 4-position with
         (i) $C(O)NR^YR^Z$; wherein $R^Y$ is hydrogen or $C_{1-6}$alkyl; and $R^Z$ is hydrogen or $C_{1-6}$alkyl optionally substituted with amino, $C_{1-2}$alkylamino, or di($C_{1-2}$alkyl)amino; or, $R^Y$ and $R^Z$ are taken together with the nitrogen atom to which they are both attached to form a 5 or 6 membered ring, and said 6 membered ring is optionally containing O or 4-N(methyl); or
         (ii) $NR^HR^J$; wherein $R^H$ and $R^J$ are independently selected from the group consisting of hydrogen and $C_{1-4}$alkyl; or, $R^H$ and $R^J$ are taken together with the nitrogen atom to which they are both attached to form a 5 or 6 membered ring;
   $R^C$ is
      (i) hydrogen;
      (ii) $C_{1-8}$ alkyl;
      (iii) $C_{3-6}$cycloalkyl;
      (iv) $C_{3-6}$cycloalkyl($C_{1-4}$)alkyl;
      (v) $CH_2CF_3$; or
      (vi) phenyl optionally independently substituted with one to two substituents selected from the group consisting of methyl, methoxy, chloro, fluoro, and trifluoromethyl;
   and any combination of embodiments a) through j) above, provided that it is understood that combinations in which different embodiments of the same substituent would be combined are excluded;
   and enantiomers, diastereomers, solvates, and pharmaceutically acceptable salts thereof.

A further embodiment of the present invention is directed to a compound of Formula (I)

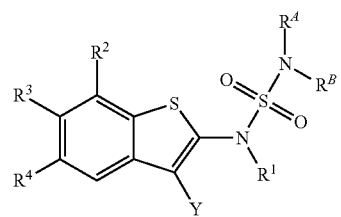

wherein
Y is hydrogen; bromo; chloro; fluoro; iodo; $C_{3-6}$ cycloalkyl; or $C_{1-4}$ alkyl;
$R^1$ is
   (i) $C_{3-6}$ cycloalkyl;
   (ii) $C_{1-6}$ alkyl substituted with one $C_{6-10}$ aryl group, wherein said $C_{6-10}$ aryl group is optionally substituted with 1 to 3 substituents independently selected from the group consisting of chloro, fluoro, bromo, $C_{1-4}$ alkyl, $C_{1-4}$ alkoxy, hydroxy, $C_{1-4}$ alkoxycarbonyl, $C_{1-3}$ alkylthio, trifluoromethylthio, cyano, trifluoromethyl, $C_{1-3}$ alkylsulfonyl optionally substituted with 1 to 3 fluoro substituents, nitro, and $C_{1-3}$ alkylcarbonyl; with the proviso that not more than two of the substituents are selected from the group consisting of $C_{1-4}$ alkoxy, $C_{1-4}$ alkoxycarbonyl, $C_{1-3}$ alkylthio, trifluoromethylthio, cyano, trifluoromethyl, $C_{1-3}$ alkylsulfonyl, nitro, and $C_{1-3}$ alkylcarbonyl;
   (iii) $C_{1-6}$ alkyl substituted with phenyl, wherein phenyl is substituted with 4 or 5 fluoro substituents; or phenyl is substituted with methoxy and 3 to 4 fluoro substituents;
   (iv) $C_{1-6}$alkyl optionally substituted with $C_{3-6}$cycloalkyl or trifluoromethyl; or
   (v) methylene substituted with benzo[1,3]dioxol-5-yl, 2,2-difluoro-benzo[1,3]dioxol-5-yl, or 2,3-dihydro-benzo[1,4]dioxin-6-yl;
$R^2$ is
   (i) hydrogen or
   (ii) fluoro;
$R^3$ is
   (i) hydrogen or
   (ii) fluoro;
$R^4$ is
   (i) hydrogen;
   (ii) methyl; or
   (iii) fluoro;
$R^A$ is $C_{1-4}$alkyl substituted at a terminal carbon atom with a substituent selected from the group consisting of carboxy, $C_{1-3}$alkoxy, and hydroxy;
$R^B$ is hydrogen or $C_{1-4}$alkyl;
   or, $R^A$ and $R^B$ are taken together with the nitrogen atom to which they are attached to form a 6 membered ring containing one additional heteroatom selected from the group consisting of O, S, and $S(O_2)$;
   or, $R^A$ and $R^B$ are taken together with the nitrogen atom to which they are attached to form a 5 or 6 membered ring, optionally containing one additional N atom, to form
      (i) piperizin-1-yl wherein the piperizinyl nitrogen is substituted with $R^C$;
      (ii) pyrrolidin-1-yl optionally substituted at the 3-position with $C_{1-4}$alkyl or $NR^DR^E$; wherein $R^D$ and $R^E$ are independently selected from the group consisting of hydrogen and $C_{1-4}$alkyl; or, $R^D$ and $R^E$ are taken together with the nitrogen atom to which they are both attached to form a 5 or 6 membered ring; and (iii) piperidin-1-yl optionally substituted with carboxy; $C_{1-3}$alkoxycarbonyl; or $C_{1-4}$alkyl substituted at a terminal carbon atom with a substituent selected from the group consisting of carboxy, $C_{1-3}$alkoxy, and hydroxy or piperidinyl is optionally substituted at the 4-position with
(i) C(O)NR$^Y$R$^Z$; wherein R$^Y$ is hydrogen or $C_{1-6}$alkyl; and R$^Z$ is hydrogen or $C_{1-6}$alkyl optionally substituted with amino, $C_{1-2}$alkylamino, or di($C_{1-2}$alkyl)amino; or, R$^Y$ and R$^Z$ are taken together with the nitrogen atom to which they are both attached to form a 5 or 6 membered ring, and said 6 membered ring is optionally containing O or 4-N(methyl); or
(ii) NR$^H$R$^J$; wherein R$^H$ and R$^J$ are independently selected from the group consisting of hydrogen and $C_{1-4}$alkyl; or, R$^H$ and R$^J$ are taken together with the nitrogen atom to which they are both attached to form a 5 or 6 membered ring;

R$^C$ is
(i) hydrogen;
(ii) $C_{1-8}$ alkyl;
(iii) $C_{3-6}$cycloalkyl;
(iv) $C_{3-6}$cycloalkyl($C_{1-4}$alkyl;
(v) CH$_2$CF$_3$; or
(vi) phenyl optionally independently substituted with one to two substituents selected from the group consisting of methyl, methoxy, chloro, fluoro, and trifluoromethyl;

and enantiomers, diastereomers, solvates, and pharmaceutically acceptable salts thereof.

A further embodiment of the present invention is directed to a compound of Formula (I)

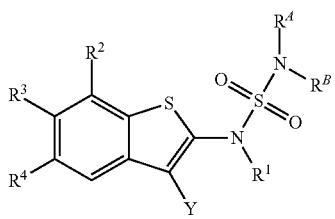

(I)

wherein
Y is hydrogen; methyl; isopropyl; chloro; cyclopropyl; cyclobutyl; cyclopentyl; or bromo;

R$^1$ is
(i) $C_{1-6}$ alkyl substituted with one $C_{6-10}$ aryl group, wherein said $C_{6-10}$ aryl group is optionally substituted with 1 to 3 substituents independently selected from the group consisting of chloro, fluoro, bromo, $C_{1-4}$ alkyl, $C_{1-4}$ alkoxy, hydroxy, $C_{1-3}$ alkylthio, trifluoromethylthio, cyano, trifluoromethyl, and $C_{1-3}$ alkylcarbonyl; with the proviso that not more than two of the substituents are selected from the group consisting of $C_{1-4}$ alkoxy, $C_{1-3}$ alkylthio, trifluoromethylthio, cyano, trifluoromethyl, and $C_{1-3}$ alkylcarbonyl;
(ii) $C_{1-3}$ alkyl substituted with phenyl, wherein phenyl is substituted with 4 or 5 fluoro substituents; or phenyl is substituted with methoxy and 3 to 4 fluoro substituents;
(iii) $C_{1-3}$alkyl optionally substituted with cyclopropyl or trifluoromethyl; or
(iv) methylene substituted with benzo[1,3]dioxol-5-yl, 2,2-difluoro-benzo[1,3]dioxol-5-yl, or 2,3-dihydro-benzo[1,4]dioxin-6-yl;

R$^C$ is
(i) hydrogen or
(ii) fluoro;
R$^3$ is
(i) hydrogen or
(ii) fluoro;
R$^4$ is
(i) hydrogen;
(ii) methyl; or
(iii) fluoro;
R$^A$ is $C_{1-4}$alkyl substituted at a terminal carbon atom with a substituent selected from the group consisting of carboxy, $C_{1-3}$alkoxy, and hydroxy;
R$^B$ is hydrogen or $C_{1-4}$alkyl;
or, R$^A$ and R$^B$ are taken together with the nitrogen atom to which they are attached to form a 6 membered ring containing one heteroatom selected from the group consisting of O, S, and S(O$_2$);
or, R$^A$ and R$^B$ are taken together with the nitrogen atom to which they are attached to form a 5 or 6 membered ring, optionally containing one additional N atom, selected from the group consisting of
(i) piperizin-1-yl wherein the piperizinyl nitrogen is substituted with R$^C$;
(ii) pyrrolidin-1-yl optionally substituted at the 3-position with $C_{1-4}$alkyl or NR$^D$R$^E$; wherein R$^D$ and R$^E$ are independently selected from the group consisting of hydrogen and $C_{1-4}$alkyl; or, R$^D$ and R$^E$ are taken together with the nitrogen atom to which they are both attached to form a 5 or 6 membered ring; and
(iii) piperidin-1-yl optionally substituted with carboxy; $C_{1-3}$alkoxycarbonyl; or $C_{1-4}$alkyl substituted at a terminal carbon atom with a substituent selected from the group consisting of carboxy, $C_{1-3}$alkoxy, and hydroxy;

or, piperidinyl is optionally substituted at the 4-position with
(i) C(O)NR$^Y$R$^Z$; wherein R$^Y$ is hydrogen or $C_{1-6}$alkyl; and R$^Z$ is hydrogen or $C_{1-6}$alkyl optionally substituted with amino, $C_{1-2}$alkylamino, or di($C_{1-2}$alkyl)amino; or, R$^Y$ and R$^Z$ are taken together with the nitrogen atom to which they are both attached to form a 5 or 6 membered ring, and said 6 membered ring is optionally containing O or 4-N(methyl); or
(ii) NR$^H$R$^J$; wherein R$^H$ and R$^J$ are independently selected from the group consisting of hydrogen and $C_{1-4}$alkyl; or, R$^H$ and R$^J$ are taken together with the nitrogen atom to which they are both attached to form a 5 or 6 membered ring;

R$^C$ is
(i) hydrogen;
(ii) $C_{1-8}$ alkyl;
(iii) $C_{3-6}$cycloalkyl;
(iv) $C_{3-6}$cycloalkyl($C_{1-4}$)alkyl;
(v) CH$_2$CF$_3$; or
(vi) phenyl optionally independently substituted with one to two substituents selected from the group consisting of methyl, methoxy, chloro, fluoro, and trifluoromethyl;

and enantiomers, diastereomers, solvates, and pharmaceutically acceptable salts thereof.

A further embodiment of the present invention is directed to a compound of Formula (I)

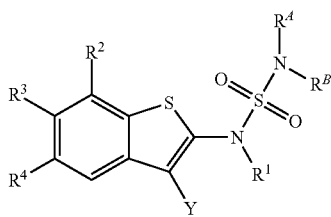

(I)

wherein

Y is hydrogen; methyl; isopropyl; chloro; cyclopropyl; or bromo;

$R^1$ is
(i) $C_{1-6}$ alkyl substituted with one $C_{6-10}$ aryl group, wherein said $C_{6-10}$ aryl group is optionally substituted with 1 to 3 substituents independently selected from the group consisting of chloro, fluoro, bromo, $C_{1-4}$ alkyl, $C_{1-4}$ alkoxy, hydroxy, $C_{1-3}$alkylthio, trifluoromethylthio, cyano, trifluoromethyl, and $C_{1-3}$alkylcarbonyl; with the proviso that not more than two of the substituents are selected from the group consisting of $C_{1-4}$ alkoxy, $C_{1-3}$alkylthio, trifluoromethylthio, cyano, trifluoromethyl, and $C_{1-3}$ alkylcarbonyl;
(ii) $C_{1-3}$ alkyl substituted with phenyl, wherein phenyl is substituted with 4 or 5 fluoro substituents; or phenyl is substituted with methoxy and 3 to 4 fluoro substituents;
(iii) $C_{1-3}$alkyl optionally substituted with cyclopropyl or trifluoromethyl; or
(iv) methylene substituted with benzo[1,3]dioxol-5-yl, 2,2-difluoro-benzo[1,3]dioxol-5-yl, or 2,3-dihydro-benzo[1,4]dioxin-6-yl;

$R^C$ is
(i) hydrogen or
(ii) fluoro;

$R^3$ is
(i) hydrogen or
(ii) fluoro;

$R^4$ is
(i) hydrogen;
(ii) methyl; or
(iii) fluoro;

$R^A$ is $C_{1-4}$alkyl substituted at a terminal carbon atom with a substituent selected from the group consisting of carboxy, $C_{1-3}$alkoxy, and hydroxy;

$R^B$ is hydrogen or $C_{1-4}$alkyl;
or, $R^A$ and $R^B$ are taken together with the nitrogen atom to which they are attached to form a 6 membered ring containing one heteroatom selected from the group consisting of O, S, and S(O$_2$);
or, $R^A$ and $R^B$ are taken together with the nitrogen atom to which they are attached to form a 5 or 6 membered ring, optionally containing one additional N atom, selected from the group consisting of
(i) piperizin-1-yl wherein the piperizinyl nitrogen is substituted with $R^C$;
(ii) pyrrolidin-1-yl optionally substituted at the 3-position with $C_{1-4}$alkyl or $NR^DR^E$; wherein $R^D$ and $R^E$ are independently selected from the group consisting of hydrogen and $C_{1-4}$alkyl; or, $R^D$ and $R^E$ are taken together with the nitrogen atom to which they are both attached to form a 5 or 6 membered ring; and
(iii) piperidin-1-yl optionally substituted with carboxy; $C_{1-3}$alkoxycarbonyl; or $C_{1-4}$alkyl substituted at a terminal carbon atom with a substituent selected from the group consisting of carboxy, $C_{1-3}$alkoxy, and hydroxy
or piperidinyl is optionally substituted at the 4-position with
(i) C(O)NR$^Y$R$^Z$; wherein $R^Y$ is hydrogen or $C_{1-6}$alkyl; and $R^Z$ is hydrogen or $C_{1-6}$alkyl optionally substituted with amino, $C_{1-2}$alkylamino, or di($C_{1-2}$alkyl)amino; or, $R^Y$ and $R^Z$ are taken together with the nitrogen atom to which they are both attached to form a 5 or 6 membered ring, and said 6 membered ring is optionally containing O or 4-N(methyl); or
(ii) NR$^H$R$^J$; wherein $R^H$ and $R^J$ are independently selected from the group consisting of hydrogen and $C_{1-4}$alkyl; or, $R^H$ and $R^J$ are taken together with the nitrogen atom to which they are both attached to form a 5 or 6 membered ring;

$R^C$ is
(iv) hydrogen;
(v) $C_{1-8}$ alkyl;
(vi) $C_{3-6}$cycloalkyl;
(vii) $C_{3-6}$cycloalkyl($C_{1-4}$)alkyl;
(viii) CH$_2$CF$_3$; or
(ix) phenyl optionally independently substituted with one to two substituents selected from the group consisting of methyl, methoxy, chloro, fluoro, and trifluoromethyl;
and enantiomers, diastereomers, solvates, and pharmaceutically acceptable salts thereof.

A further embodiment of the present invention is directed to compounds of Formula (I)

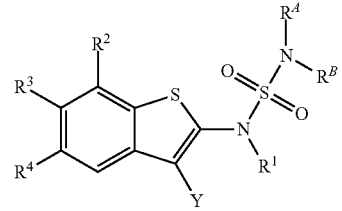

(I)

selected from the group consisting of
a compound wherein Y is bromo, $R^1$ is 4-fluoro-3-trifluoromethylphenylmethyl, $R^2$, $R^3$, and $R^4$ are H, $R^A$ is H, and $R^B$ is carboxymethyl;
a compound wherein Y is bromo, $R^1$ is 4-fluoro-3-trifluoromethylphenylmethyl, $R^2$, $R^3$, and $R^4$ are H, $R^A$ is H, and $R^B$ is 3-carboxypropyl;
a compound wherein Y is methyl, $R^1$ is 4-fluoro-3-trifluoromethylphenylmethyl, $R^2$, $R^3$, and $R^4$ are H, $R^A$ is H, and $R^B$ is 3-carboxypropyl;
a compound wherein Y is bromo, $R^1$ is 4-fluoro-3-trifluoromethylphenylmethyl, $R^2$, $R^3$, and $R^4$ are H, $R^A$ is H, and $R^B$ is 4-carboxybutyl;
a compound wherein Y is methyl, $R^1$ is 4-trifluoromethoxyphenylmethyl, $R^2$, $R^3$, and $R^4$ are H, and $R^A$ and $R^B$ are taken together with the nitrogen atom to which they are both attached to form 4-methylpiperazin-1-yl;
a compound wherein Y is methyl, $R^1$ is 4-trifluoromethoxyphenylmethyl, $R^2$, $R^3$, and $R^4$ are H, and $R^A$ and $R^B$ are taken together with the nitrogen atom to which they are both attached to form 4-carboxypiperidin-1-yl;
a compound wherein Y is methyl, $R^1$ is 4-trifluoromethoxyphenylmethyl, $R^2$, $R^3$, and $R^4$ are H, and $R^A$ and $R^B$ are taken together with the nitrogen atom to which they are both attached to form 4-(4-methylpiperazin-1-ylcarbonyl)piperidin-1-yl;

a compound wherein Y is methyl, $R^1$ is 4-trifluoromethoxyphenylmethyl, $R^2$, $R^3$, and $R^4$ are H, and $R^A$ and $R^B$ are taken together with the nitrogen atom to which they are both attached to form 4-(2-dimethylamino-ethylaminocarbonyl)piperidin-1-yl;

a compound wherein Y is methyl, $R^1$ is 4-trifluoromethoxyphenylmethyl, $R^2$, $R^3$, and $R^4$ are H, and $R^A$ and $R^B$ are taken together with the nitrogen atom to which they are both attached to form piperazin-1-yl;

a compound wherein Y is methyl, $R^1$ is 4-trifluoromethoxyphenylmethyl, $R^2$, $R^3$, and $R^4$ are H, and $R^A$ and $R^B$ are taken together with the nitrogen atom to which they are both attached to form 4-isopropyl-piperazin-1-yl;

a compound wherein Y is methyl, $R^1$ is 4-trifluoromethoxyphenylmethyl, $R^2$, $R^3$, and $R^4$ are H, and $R^A$ and $R^B$ are taken together with the nitrogen atom to which they are both attached to form 4-(3-methyl-butyl)-piperazin-1-yl;

a compound of Formula (I) wherein Y is methyl, $R^1$ is 4-trifluoromethoxyphenylmethyl, $R^2$, $R^3$, and $R^4$ are H, and $R^A$ and $R^B$ are taken together with the nitrogen atom to which they are both attached to form 4-(2,2,2-trifluoroethyl)-piperazin-1-yl;

a compound of Formula (I) wherein Y is methyl, $R^1$ is 4-trifluoromethoxyphenylmethyl, $R^2$, $R^3$, and $R^4$ are H, and $R^A$ and $R^B$ are taken together with the nitrogen atom to which they are both attached to form 4-(dimethylamino)piperidin-1-yl;

a compound of Formula (I) wherein Y is methyl, $R^1$ is 4-trifluoromethoxyphenylmethyl, $R^2$, $R^3$, and $R^4$ are H, and $R^A$ and $R^B$ are taken together with the nitrogen atom to which they are both attached to form 4-(pyrrolidin-1-yl)piperidin-1-yl;

a compound of Formula (I) wherein Y is methyl, $R^1$ is 4-trifluoromethoxyphenylmethyl, $R^2$, $R^3$, and $R^4$ are H, and $R^A$ and $R^B$ are taken together with the nitrogen atom to which they are both attached to form piperidin-1-yl;

a compound of Formula (I) wherein Y is methyl, $R^1$ is 4-trifluoromethoxyphenylmethyl, $R^2$, $R^3$, and $R^4$ are H, and $R^A$ and $R^B$ are taken together with the nitrogen atom to which they are both attached to form morpholin-4-yl;

and enantiomers, diastereomers, solvates, and pharmaceutically acceptable salts thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salts thereof. Suitable pharmaceutically acceptable salts of compounds of Formula (I) include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts, such as sodium or potassium salts; alkaline earth metal salts, such as calcium or magnesium salts; and salts formed with suitable organic ligands, such as quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, a-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide. Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985. Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula I.

Where the processes for the preparation of the compounds according to certain embodiments of the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as During any of the processes for preparation of the compounds of the various embodiments of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1999. The protecting groups may be removed at a convenient subsequent stage using methods known from the art. Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient, and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms, such as tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration includes transdermal administration by using a skin or transdermal patch. The pharmaceutical compositions of the present invention (as well as the compounds of the present invention alone) can also be injected parenterally, for example intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus for liquid oral preparations, such as suspensions, syrups, elixirs and solutions, suitable carriers, excipients and diluents include water, glycols, oils, alcohols, flavoring agents, preservatives, stabilizers, coloring agents and the like; for solid oral preparations, such as powders, capsules and tablets, suitable carriers, excipients and diluents include starches, sugars, diluents, granulating agents, lubricants, binders, disintegrating agents and the like. Solid oral preparations also may be optionally coated with substances, such as sugars, or be enterically-coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives, such as solubilizers and preservatives.

A therapeutically effective amount of a compound of Formula (I) or a pharmaceutical composition thereof includes a dose range from about 0.1 mg to about 3000 mg, in particular from about 1 mg to about 1000 mg or, more particularly, from about 10 mg to about 500 mg of active ingredient in a regimen of about 1 to 4 times per day for an average (70 kg) human; although, it is apparent to one skilled in the art that the therapeutically effective amount for active compounds of the invention will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of the inventive compound as the active ingredient.

Advantageously, a compound of Formula (I) may be administered in a single daily dose, or the total daily dosage may be administered in divided doses of two, three and four times daily. Optimal dosages of a compound of Formula (I) to be administered may be readily determined and will vary with the particular compound used, the mode of administration, the strength of the preparation, and the advancement of the disease, syndrome, condition, or disorder. In addition, factors associated with the particular subject being treated, including subject age, weight, diet and time of administration, will result in the need to adjust the dose to achieve an appropriate therapeutic level. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof. As antagonists of the TRPM8 ion channel, the compounds of Formula (I) are useful in methods for treating and preventing a disease, a syndrome, a condition, or a disorder in a subject, including an animal, a mammal and a human in which the disease, the syndrome, the condition, or the disorder is affected by the modulation of TRPM8 receptors. Such methods comprise, consist of, and consist essentially of administering to a subject, including an animal, a mammal, and a human in need of such treatment or prevention a therapeutically effective amount of a compound, salt, or solvate of Formula (I). In particular, the compounds of Formula (I) are useful for preventing or treating pain, or diseases, syndromes, conditions, or disorders causing such pain, or pulmonary or vascular dysfunction. More particularly, the compounds of Formula (I) are useful for preventing or treating inflammatory pain, inflammatory hypersensitivity conditions, neuropathic pain, anxiety, depression, and cardiovascular disease aggravated by cold, including peripheral vascular disease, vascular hypertension, pulmonary hypertension, Raynaud's disease, and coronary artery disease, by administering to a subject in need thereof a therapeutically effective amount of a compound of Formula (I).

Examples of inflammatory pain include pain due to a disease, condition, syndrome, disorder, or a pain state including inflammatory bowel disease, visceral pain, migraine, post-operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, sinus headache, tension headache, or arachnoiditis.

One type of inflammatory pain is inflammatory hyperalgesia, which can be further distinguished as inflammatory somatic hyperalgesia or inflammatory visceral hyperalgesia. Inflammatory somatic hyperalgesia can be characterized by the presence of an inflammatory hyperalgesic state in which a hypersensitivity to thermal, mechanical and/or chemical stimuli exists. Inflammatory visceral hyperalgesia can also be characterized by the presence of an inflammatory hyperalgesic state, in which an enhanced visceral irritability exists.

Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, inflammatory bowel diseases including Crohn's Disease or ulcerative colitis.

One embodiment of the present invention is directed to a method for treating inflammatory somatic hyperalgesia in which a hypersensitivity to thermal, mechanical and/or chemical stimuli exists, comprising the step of administering to a subject in need of such treatment a therapeutically effective amount of a compound, salt or solvate of Formula (I).

A further embodiment of the present invention is directed to a method for treating inflammatory visceral hyperalgesia in which a enhanced visceral irritability exists, comprising, consisting of, and/or consisting essentially of the step of administering to a subject in need of such treatment a therapeutically effective amount of a compound, salt or solvate of Formula (I).

A further embodiment of the present invention is directed to a method for treating neuropathic cold allodynia in which a hypersensitivity to a cooling stimuli exists, comprising, consisting of, and/or consisting essentially of the step of administering to a subject in need of such treatment a therapeutically effective amount of a compound, salt or solvate of Formula (I).

Examples of an inflammatory hypersensitivity condition include urinary incontinence, benign prostatic hypertrophy, cough, asthma, rhinitis and nasal hypersensitivity, itch, contact dermatitis and/or dermal allergy, and chronic obstructive pulmonary disease.

Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, neuralgias (trigeminal neuralgia, glossopharyngeal neuralgia, postherpetic neuralgia and causalgia), lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

Examples of anxiety include social anxiety, post-traumatic stress disorder, phobias, social phobia, special phobias, panic disorder, obsessive-compulsive disorder, acute stress disorder, separation anxiety disorder, and generalized anxiety disorder.

Examples of depression include major depression, bipolar disorder, seasonal affective disorder, post-natal depression, manic depression, and bipolar depression.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:

| | |
|---|---|
| CAN | ceric ammonium nitrate |
| DCE | 1,2-dichloroethane |
| DCM | dichloromethane |
| DIEA | diisopropyl-ethyl amine |
| DMF | N,N-dimethylformamide |
| DMSO | dimethylsulfoxide |
| DPPA | diphenylphosphoryl azide |
| EDC | N-(3-dimethylaminopropyl)-N'-ethylcarbodiimide hydrochloride |
| ESI | electron-spray ionization |
| EtOAc | ethyl acetate |
| EtOH | ethanol |
| HEK | human embryonic kidney |
| HPLC | high performance liquid chromatography |
| MeCN | acetonitrile |
| MeOH | methanol |
| MeOTf | methyl triflate |
| MHz | megahertz |
| min | minutes |
| MS | mass spectroscopy |
| NBS | N-bromosuccinimide |
| NMR | nuclear magnetic resonance |
| RP | reverse-phase |
| $R_t$ | retention time |
| TEA/Et$_3$N | triethylamine |
| TFA | trifluoroacetic acid |
| THF | tetrahydrofuran |
| TLC | thin layer chromatography |
| TMS | tetramethylsilane |

LC-MS/HPLC Methods:

method 1 (HPLC): Instrument: HP 1100 with DAD-detection, column. Gemini C18, 110 A, 30×4.60 mm, 3.0µ; eluent A: water (0.1% TFA), eluent B: acetonitrile (0.1% TFA); gradient: 0 min 96% A→8.5 min 95% B; flow: 1.2 mL/min; UV detection: 210 and 254 nm.

method 2 (LC-MS): Instrument MS: Micromass LCZ; instrument HPLC Agilent Series 1100; column: SupelcoCosil ABZ+PLUS 3µ, 3.3 cm×2.1 mm; eluent A: water (0.1% TFA), eluent B: acetonitrile (0.1% TFA); gradient: 0.0 min 100% A→6.5 min 100% B; flow 0.5 ml/min; UV detection: 210 and 254 nm.

method 3 (RP-HPLC): Instrument HPLC Gilson, 215 Liquid Handler, 306 Pumps; column: Gemini AXIA, C18, 110 A, 5µ, 100×30.0 mm; eluent A: water (0.1% TFA), eluent B: acetonitrile (0.1% TFA); gradient 0.0 min starting % A→12 min ending % B; flow 32 ml/min; UV detection: 210 and 254 nm.

Scheme A illustrates a route for the synthesis of certain intermediates of the present invention, wherein $Y_A$ is hydrogen or alkyl; and $R^2$, $R^3$ and $R^4$ are as defined herein.

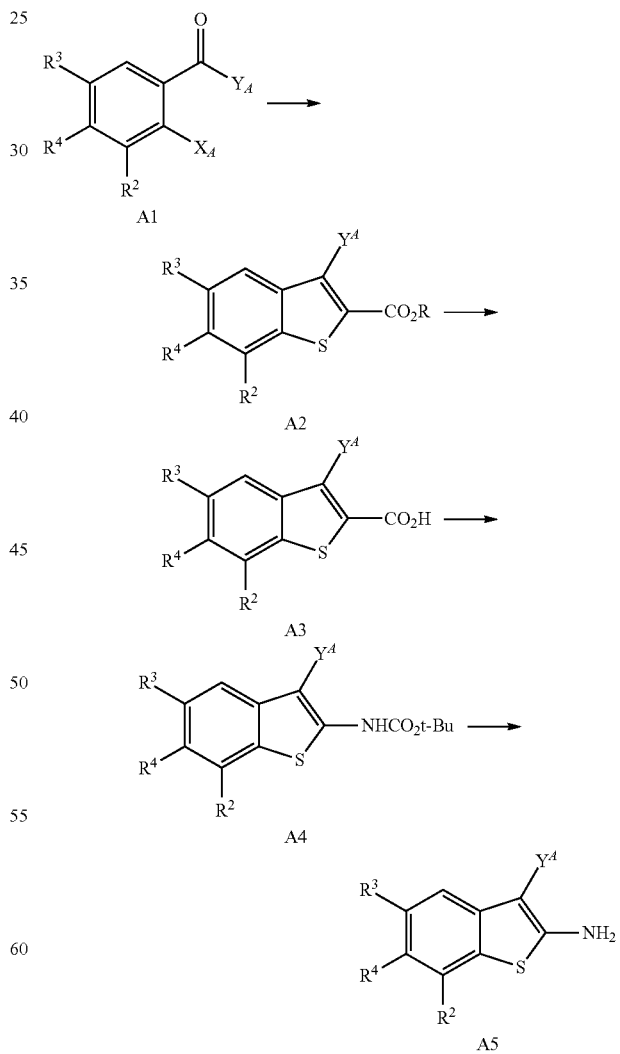

Scheme A

A compound of the formula A1 is either commercially available or may be prepared by known methods described in the scientific literature. A compound of the formula A1, wherein $X_A$ is chloro or fluoro and $Y_A$ is hydrogen or alkyl, may be reacted with an R-substituted thioglycolate (wherein R is $C_{1-6}$alkyl) in the presence of base to afford a compound of the formula A2, which may be saponified to afford a compound of the formula A3 using conventional chemistry known to one skilled in the art. A compound of the formula A3 may be converted to a compound of the formula A4 using diphenylphosphoryl azide, tert-butanol and an organic base. A compound of the formula A4 may be converted to the corresponding amine, a compound of the formula A5, by the action of HCl or another mineral acid, or by the action of an organic acid, such as trifluoroacetic acid.

Scheme B illustrates a route for the synthesis of compounds of formula (I)-B wherein $R^A$ and $R^B$ are taken together to form an optionally substituted pyrrolidinyl or piperidinyl ring.

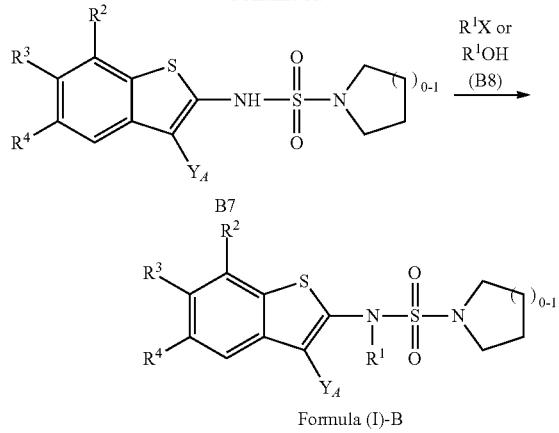

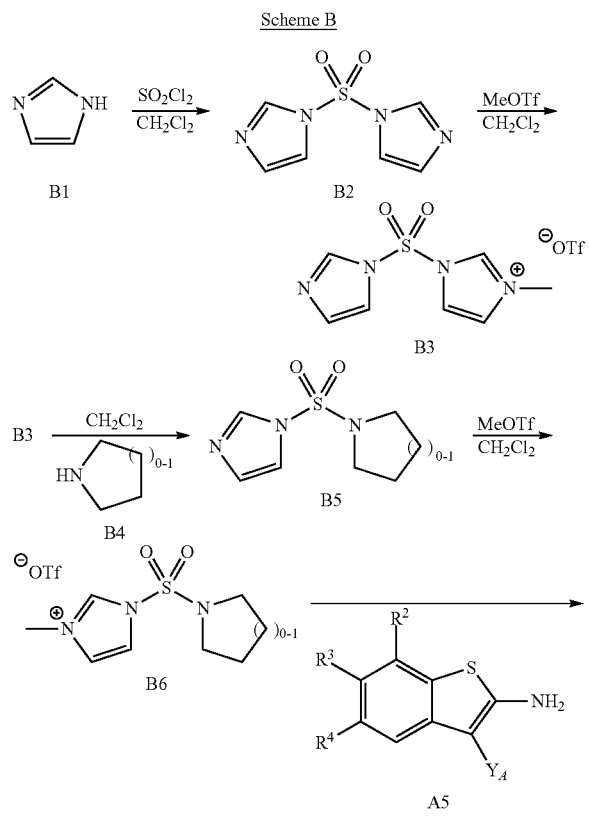

A compound B1 may be converted to a compound B2 using sulfuryl chloride in an aprotic organic solvent. A compound B2 may be methylated in the presence of methyl triflate to form a compound B3. A compound B3 may be treated with a cyclic amine of the formula B4 to form a compound of the formula B5. Subsequent treatment with methyl triflate forms a methylated product of the formula B6, which may be reacted with a compound of the formula A5 to form a compound of the formula B7. A compound of the formula B7 may be treated with a base such as sodium hydride, lithium bis(trimethylsilyl)amide, n-butyllithium, potassium carbonate, or potassium tert-butoxide followed by alkylation with a compound of the formula, $R^1X$, where X is a leaving group such as bromo, chloro, iodo, tosylate, mesylate, and the like, to afford a compound of the formula (I)-B. Alternatively, a compound of the formula B7 may be treated with a triarylphosphine such as triphenylphosphine, tri-o-tolylphosphine, tri-2-furylphosphine and the like; a $C_{1-6}$ dialkyl azodicarboxylate such as diethyl-, diisopropyl-, or di-t-butyl-azodicarboxylate, and the like; and an appropriately substituted alcohol, $R^1OH$, to afford a compound of the formula (I)-B.

Scheme C illustrates a route for the synthesis of compounds of formula (I)-C1 and formula (I)-C2 wherein $R^A$ and $R^B$ are taken together to form an optionally substituted ring containing an additional heteroatom G (G is selected from the group consisting of O, S, S($O_2$), N(PG), and N($R^C$), wherein PG is a conventional amino protecting group.

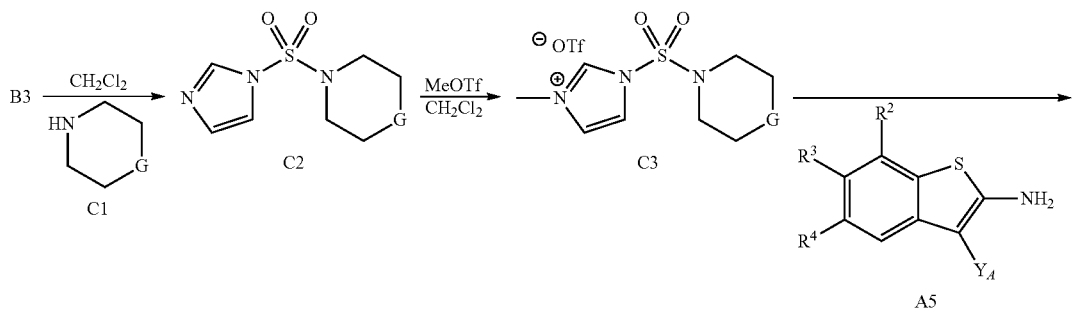

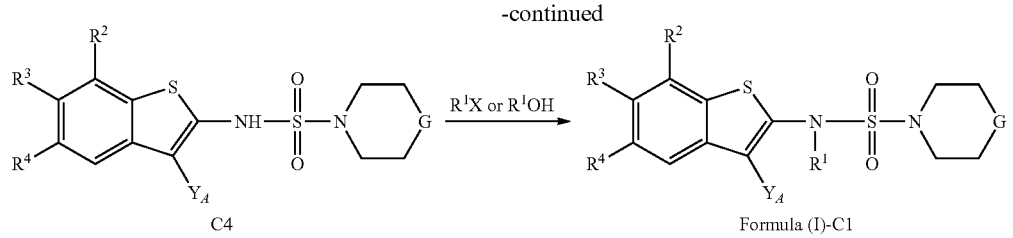

C4 → Formula (I)-C1

1) R¹X or R¹OH
2) when G is N(PG), amino deprotection

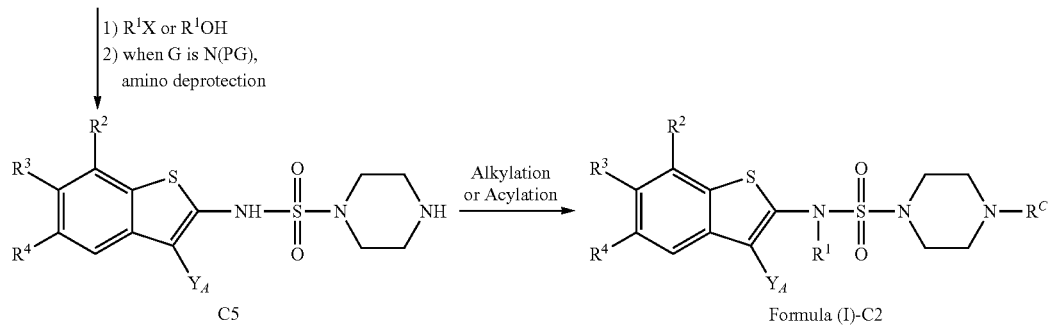

C5 → Formula (I)-C2

A compound B3 may be treated with a cyclic amine of the formula C1 to form a compound of the formula C2. Methylation of a compound of the formula C2 with methyl triflate affords a compound of the formula C3. Treatment with a compound of the formula A5 affords a compound of the formula C4, which may be alkylated according to the methods described in scheme B to form a compound of the formula (I)-C1 (wherein G is O, S, or S(O₂)). Alternatively, G may be a protected amino group, N(PG). When G is N(PG), the protecting group may be removed using conventional chemistry to afford an amine of the formula C5, which may be alkylated or acylated using conventional reductive amination, alkylation, or acylation chemistry with an appropriate $R^C$-substituted reagent to form a compound of the formula (I)-C2 wherein $R^C$ is as defined herein.

Scheme D illustrates a route for the synthesis of compounds of formula (I)-D wherein $R^A$ and $R^B$ are taken together to form a piperidinyl ring substituted at the 4-position with $NR^D R^E$.

Scheme D

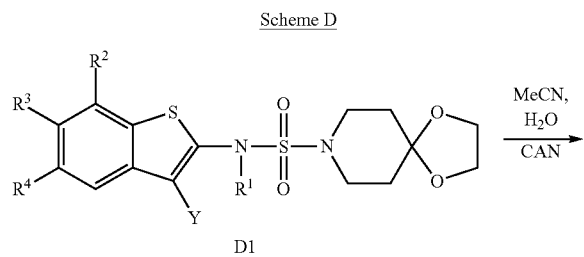

A compound of the formula D1 may be prepared according to the methods described in scheme B, substituting 1,4-dioxa-8-aza-spiro[4,5]decane for a compound of the formula B4. Treatment with ceric ammonium nitrate (CAN) affords a ketone of the formula D2. Reductive amination with an amine of the formula D3 in the presence of a hydride source such as triacetoxysodiumborohydride affords a compound of the formula (I)-D.

Scheme E illustrates a route for the synthesis of compounds of formula (I)-E wherein piperidin-1-yl is substituted with 4-C(O)NR^Y R^Z, wherein $R^Y$ and $R^Z$ are as defined herein, and are optionally taken together to form a 5 or 6-membered ring, wherein said 6-membered ring optionally contains an O or N-methyl.

Scheme E

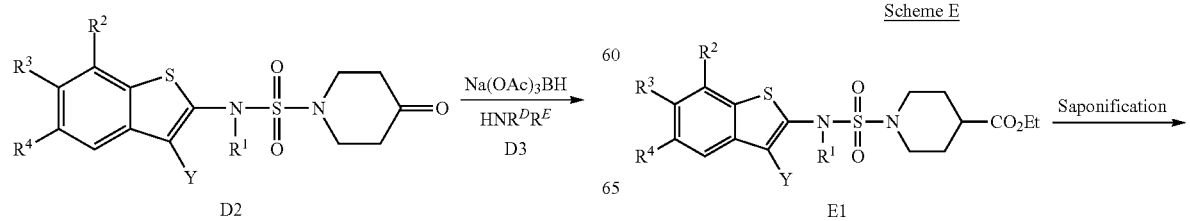

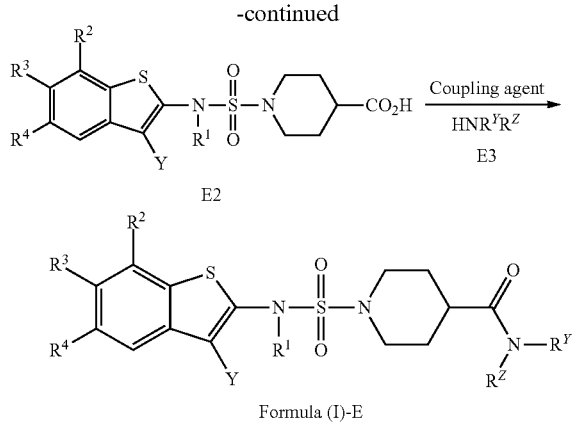

A compound of the formula E1 may be prepared according to the methods described in scheme B, by substituting a 4-ethoxycarbonyl-piperidine for a compound of the formula B4. Conventional saponification of a compound of the formula E1 affords a carboxylic acid of the formula E2. Coupling of the acid with an amine of the formula E3 in the presence of a coupling agent such as HBTU, DCC, HATU, EDC, and the like; in an aprotic solvent, affords an amide of the formula (I)-E.

Scheme F illustrates a route for the synthesis of compounds of formula (I)-F wherein $R^A$ is $C_{1-6}$alkyl substituted at a terminal carbon atom with a substituent selected from the group consisting of carboxy and $C_{1-4}$alkoxycarbonyl.

A compound of the formula F1 is either commercially available or may be prepared by known methods described in the scientific literature. A compound of the formula F1 may be treated with diphenylphosphorylazide in the presence of a base and t-butyl alcohol to form a Boc-protected amine of the formula F2, which may then be alkylated according to the methods described in scheme B to form an $R^1$-substituted compound of the formula F3. The Boc protecting group may be removed using conventional chemistry, such as by the action of HCl or another mineral acid, or by the action of an organic acid, such as trifluoroacetic acid to form a compound of the formula F4. Treatment of an amine of the formula F4 with chlorosulfonyl isocyanate, in the presence of t-butyl alcohol, affords a sulfamide of the formula F5. A compound of the formula F5 may be alkylated by the action of a base in the presence of an $R^A$-substituted alkylating agent of the formula F6, wherein LG is a leaving group such as a bromide, iodide, tosylate, and the like. Final removal of the Boc amino protecting group affords a compound of the formula (I)-F.

Scheme G illustrates a route for the synthesis of certain intermediates of formula G5 wherein Y is fluoro.

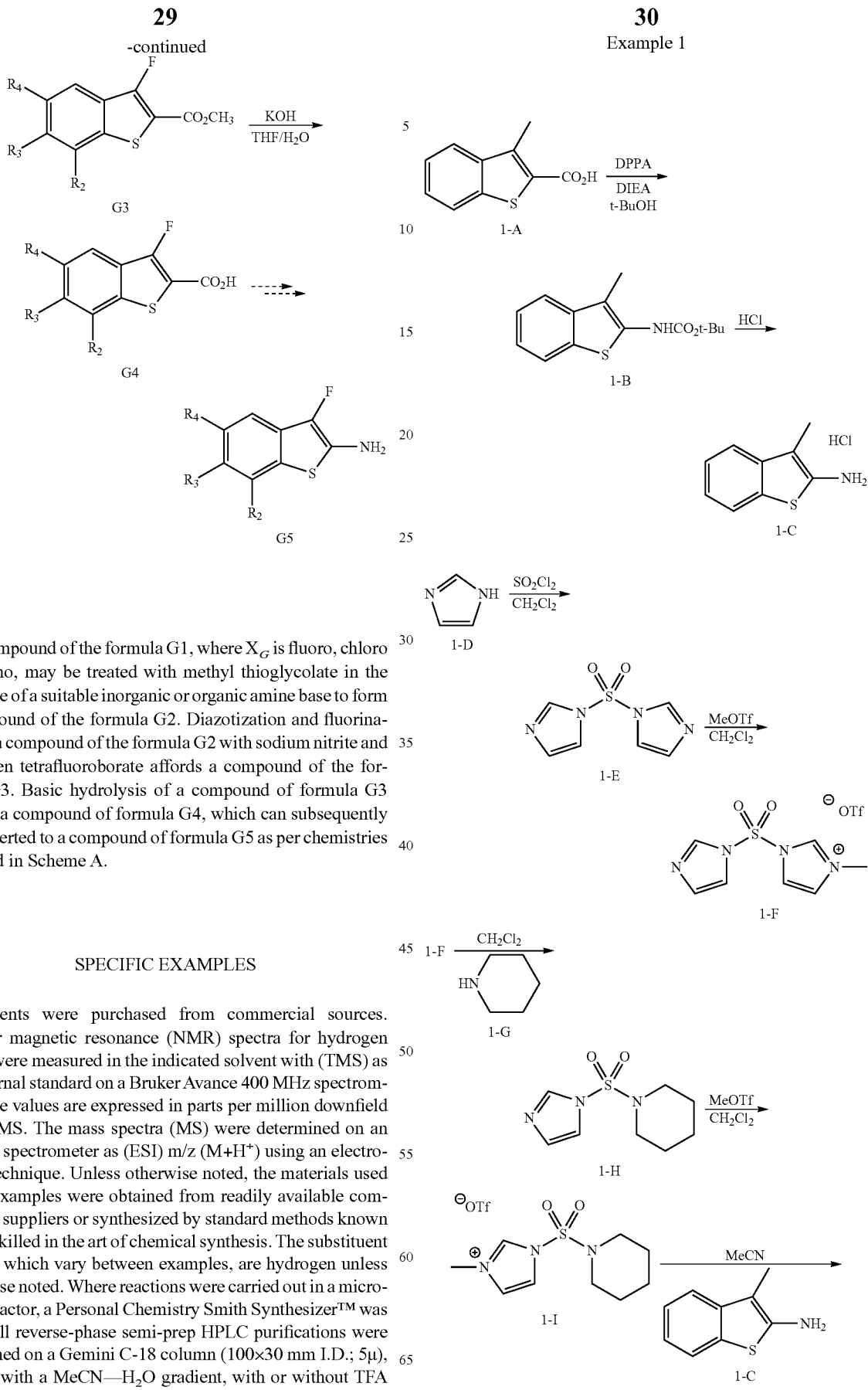

A compound of the formula G1, where $X_G$ is fluoro, chloro or bromo, may be treated with methyl thioglycolate in the presence of a suitable inorganic or organic amine base to form a compound of the formula G2. Diazotization and fluorination of a compound of the formula G2 with sodium nitrite and hydrogen tetrafluoroborate affords a compound of the formula G3. Basic hydrolysis of a compound of formula G3 affords a compound of formula G4, which can subsequently be converted to a compound of formula G5 as per chemistries outlined in Scheme A.

SPECIFIC EXAMPLES

Reagents were purchased from commercial sources. Nuclear magnetic resonance (NMR) spectra for hydrogen atoms were measured in the indicated solvent with (TMS) as the internal standard on a Bruker Avance 400 MHz spectrometer. The values are expressed in parts per million downfield from TMS. The mass spectra (MS) were determined on an Agilent spectrometer as (ESI) m/z (M+H$^+$) using an electrospray technique. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted. Where reactions were carried out in a microwave reactor, a Personal Chemistry Smith Synthesizer™ was used. All reverse-phase semi-prep HPLC purifications were performed on a Gemini C-18 column (100×30 mm I.D.; 5μ), eluting with a MeCN—H$_2$O gradient, with or without TFA additive.

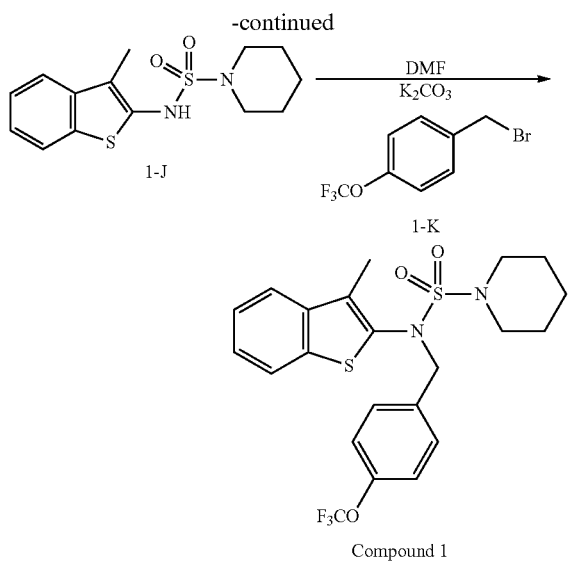

Compound 1

A. tert-Butyl-3-methylbenzo[b]thiophen-2-ylcarbamate (1-B). A 5-L 4-neck flask equipped with an overhead mechanical stirrer, $N_2$ inlet/outlet adapter, reflux condenser, heating mantle and thermocouple was charged with t-butyl alcohol (2.11 L), compound 1-A (225.0 g, 1.17 mol), and diisopropylethylamine (225 mL, 1.29 mol). Diphenylphosphorylazide (304 mL, 1.4 mol) was premixed with toluene (300 mL) and then added drop-wise over 10 min. The reaction mixture was refluxed with stirring for 21 h, cooled to 22° C. and then evaporated in vacuo. The residue was dissolved in $CH_2Cl_2$ (1 L), washed with 1N NaOH (500 mL), brine (500 mL), the organic layer separated, dried over $MgSO_4$, filtered, and evaporated in vacuo to afford a dark orange oil (557 g). The crude residue was purified by the flash column chromatography ($SiO_2$) eluting with heptane-EtOAc to afford 265 g of compound 1-B as a pale yellow solid. $^1$H-NMR ($CDCl_3$): δ 7.71 (d, 1H), 7.54 (d, 1H), 7.36-7.31 (m, 1H), 7.30-7.20 (m, 1H), 6.75 (br s, 1H), 2.23 (s, 3H), 1.55 (s, 9H).

B. 3-Methylbenzo[b]thiophen-2-amine hydrochloride (1-C). A 5-L 3-neck flask equipped with an overhead mechanical stirrer, $N_2$ inlet/outlet adapter, and thermocouple was charged with 4M HCl in dioxane (3.1 L), compound 1-B (265 g, 1.0 mol) and stirred for 18 h at 22° C. The white precipitate was collected by filtration, washed with diethyl ether (3×500 mL), and dried under house vacuum at 40° C. for 48 h to afford 174 g of compound 1-C as a white solid. $^1$H-NMR (DMSO-$d_6$): δ 8.7 (br s, 3H), 7.71 (d, 1H), 7.44 (d, 1H), 7.29 (t, 1H), 7.14 (t, 1H), 2.184 (s, 3H).

C. 1,1'-Bis-imidazole-1-sulfonyl (1-E). To a solution of compound 1-D (20.0 g, 294 mmol) in anhydrous $CH_2Cl_2$ (210 mL), cooled to 0° C., was added a solution of sulfuryl chloride (5.0 mL, 61.6 mmol) in $CH_2Cl_2$ (28 mL), drop-wise. The reaction mixture was allowed to warm to ambient temperature and stirred for 16 hours. The reaction mixture was filtered, the solvent evaporated under reduced pressure, and the resulting solid crystallized from isopropyl alcohol (100 mL). The white needles were filtered, washed with cold isopropyl alcohol and dried under reduced pressure to afford 7.81 g (64%) of compound 1-E as a white solid. $^1$H-NMR (DMSO-$d_6$, 400 MHz): δ 8.50-8.51 (d, 2H), 7.92 (s, 2H), 7.24-7.23 (d, 2H); MS (method 2) m/z 198.9 (M+1).

D. 1,1'-Bis-(3-methyl-imidazole)-1-sulfonyl triflate salt (1-F). To a solution of compound 1-E (1.26 g, 6.36 mmol) in $CH_2Cl_2$ (10 mL), cooled to 0° C., was added methyl triflate (0.719 mL, 6.36 mmol). The reaction mixture was allowed to warm to ambient temperature and stirred for 18 hours. The solvent was evaporated under reduced pressure to afford compound 1-F as a white solid.

E. 1-(Imidazole-1-sulfonyl)-piperidine (1-H). To compound 1-F (0.375 g, 1.03 mmol) dissolved in MeCN (1 mL) was added piperidine (1-G) (0.123 mL, 1.24 mmol) and the reaction mixture was stirred at room temperature for 18 hours. The reaction mixture was purified by reverse-phase semi-prep HPLC (method 3) eluting with a 30% to 50% gradient (no TFA additive) to afford 79.6 mg (36%) of compound 1-H as a white solid. MS (method 2): m/z 216.0 (M+1).

F. 1-Methyl-3-(piperidine-1-sulfonyl)-3H-imidazol-1-ium triflate salt (1-I). To a solution of compound 1-H (79.6 mg, 0.37 mmol) in $CH_2Cl_2$ (2 mL), cooled to 0° C., was added methyl triflate (46 μL, 0.407 mmol). The reaction mixture was allowed to warm to ambient temperature and stirred for 3 hours. The solvent was evaporated under reduced pressure to afford compound 1-I as a white solid. MS (method 2): m/z 229.9 (MH$^+$).

G. Piperidine-1-sulfonic acid (3-methyl-benzo[b]thiophen-2-yl)-amide (1-J). To a solution of compound 1-I (85.2 mg, 0.37 mmol) in MeCN (1.0 mL) was added a solution of compound 1-C (120.8 mg, 0.74 mmol) in MeCN (1.0 mL) and the reaction mixture was heated under microwave irradiation at 140° C. for 10 minutes. The reaction mixture was purified by reverse-phase semi-prep HPLC (method 3) eluting with a 45% MeCN—$H_2O$ (0.1% TFA) to 65% MeCN—$H_2O$ (0.1% TFA) gradient to afford 46 mg of compound 1-J as a film. $^1$H-NMR ($CDCl_3$, 400 MHz): δ 7.71-7.73 (t, 1H), 7.63-7.66 (t, 1H), 7.34-7.40 (m, 2H), 6.28 (s, 1H), 3.27-3.29 (m, 4H), 2.39 (s, 3H), 1.53-1.73 (m, 6H); MS (method 2): m/z 311.0 (M+1).

H. Piperidine-1-sulfonic acid (3-methyl-benzo[b]thiophen-2-yl)-(4-trifluoromethoxy-benzyl)-amide, Compound 1. To a solution of compound 14 (46 mg, 0.148 mmol) in DMF (1.5 mL) was added potassium carbonate (30.7 mg; 0.222 mmol) and the reaction mixture was stirred at room temperature for 30 minutes. 4-Trifluoromethoxy benzyl bromide (1-K) (45.3 mg, 0.178 mmol) was added drop-wise and the reaction mixture was stirred at room temperature for 18 hours. The reaction mixture was partitioned between $H_2O$ and EtOAc, the organic phase washed with $H_2O$, brine, dried over $Na_2SO_4$, filtered, and the solvent evaporated under reduced pressure to afford a yellow oil. The crude residue was purified by reverse-phase semi-prep HPLC (method 3) eluting with a 65% MeCN—$H_2O$ (0.1% TFA) to 85% MeCN—$H_2O$ (0.1% TFA) gradient to afford 40.6 mg of compound 1 as a semi-solid. $^1$H-NMR ($CDCl_3$, 400 MHz): δ 7.71-7.73 (m, 1H), 7.52-7.58 (m, 1H), 7.34-7.37 (m, 2H), 7.27-7.31 (m, 2H), 6.99-7.21 (m, 2H), 4.72 (s, 2H), 3.24-3.27 (m, 4H), 1.97 (s, 3H), 1.52-1.62 (m, 6H); MS (method 2): m/z 485.0 (M+1).

Following the procedure described above for Example 1 and substituting the appropriate reagents, starting materials and purification methods known to those skilled in the art, the following compounds of the present invention were prepared:

Morpholine-1-sulfonic acid (3-methyl-benzo[b]thiophen-2-yl)-(4-trifluoromethoxy-benzyl)-amide, Compound 2. Compound 2 was prepared substituting morpholine for piperidine in Example 1, step E, to afford 32.6 mg as a semi-solid. $^1$H-NMR ($CDCl_3$, 400 MHz): δ 7.71-7.75 (m, 1H), 7.54-7.64 (m, 1H), 7.34-7.40 (m, 2H), 7.27-7.29 (m, 2H), 6.99-7.16 (m, 2H), 4.76 (s, 2H), 3.68-3.70 (m, 4H), 3.11-3.30 (m, 4H), 1.97 (s, 3H); MS (method 2): m/z 487.0 (M+1).

Example 2

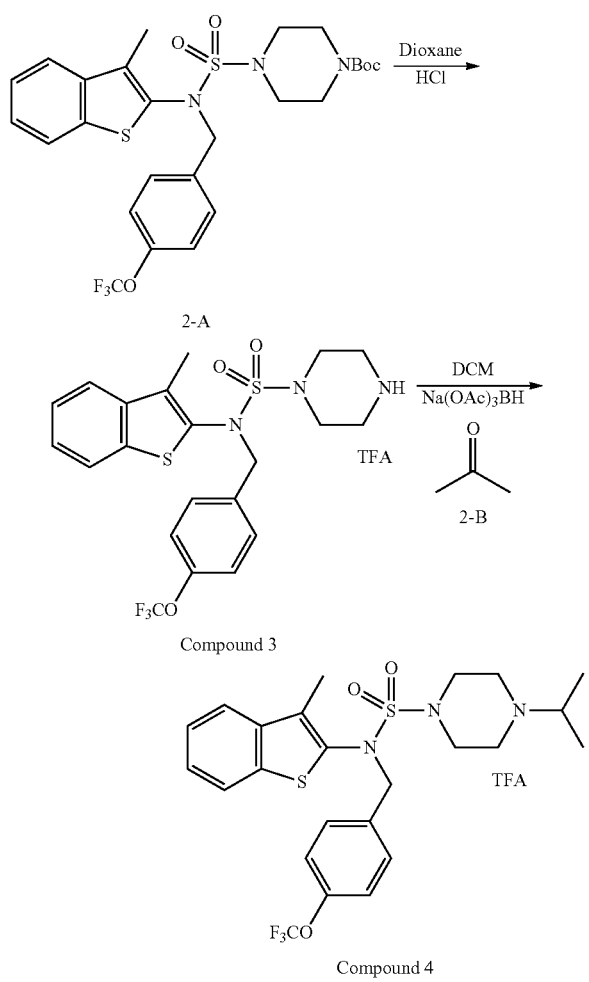

A. 4-[(3-Methyl-benzo[b]thiophen-2-yl)-(4-trifluoromethoxy-benzyl)-sulfamoyl]-piperazine-1-carboxylic acid tert butyl ester (2-A). Compound 2-A (159.9 mg (80%), white foam) was prepared substituting N-boc piperazine for piperidine in Example 1, step E, and using the chemistry outlined in steps F to H. $^1$H-NMR (DMSO-$d_6$, 400 MHz): δ 7.86-7.88 (m, 1H), 7.64-7.66 (m, 1H), 7.35-7.41 (m, 4H), 7.27-7.29 (m, 2H), 4.77 (s, 2H), 3.38-3.40 (m, 4H), 3.25-3.27 (m, 4H), 1.99 (s, 3H), 1.40 (s, 9H); MS (method 2): m/z 485.9 (M-Boc$^+$); HPLC (method 1): $R_t$=7.76 minutes.

B. Piperazine-1-sulfonic acid (3-methyl-benzo[b]thiophen-2-yl)-(4-trifluoromethoxy-benzyl)-sulfamoyl]-amide, Compound 3. To a solution of compound 2-A (159.9 mg, 0.273 mmol) was added 4N hydrochloride solution in dioxane (4 mL) and the reaction mixture was stirred at room temperature for 3 hours. The solvent was evaporated under reduced pressure and the crude reaction mixture purified by reverse-phase semi-prep HPLC (method 3) eluting with a 40% MeCN—H$_2$O (0.1% TFA) to 60% MeCN—H$_2$O (0.1% TFA) gradient to afford 129.2 mg (79%) of compound 3 as a waxy white solid. MS (method 2): m/z 485.9 (MH$^+$); HPLC (method 1): $R_t$ 5.18 minutes.

C. 4-Isopropyl-piperazine-1-sulfonic acid (3-methyl-benzo[b]thiophen-2-yl)-(4-trifluoromethoxy-benzyl)-sulfamoyl]-amide, Compound 4. To a solution of compound 3 (38.4 mg, 0.066 mmol) in dichloromethane (0.8 mL) was added triethylamine (10 μL, 0.073 mmol) and acetone (2-B) (24 μL, 0.33 mmol) and the reaction mixture was stirred at room temperature for 30 minutes. Sodium triacetoxyborohydride (21 mg, 0.099 mmol) was added and the reaction mixture was stirred for 18 hours. The reaction mixture was diluted with dichloromethane, washed with H$_2$O, dried over Na$_2$SO$_4$, filtered, and the solvent evaporated under reduced pressure. The crude reaction mixture purified by reverse-phase semi-prep HPLC (method 3) eluting with a 40% MeCN—H$_2$O (0.1% TFA) to 60% MeCN—H$_2$O (0.1% TFA) gradient to afford 28.2 mg of compound 4 as a clear semi-solid. $^1$H-NMR (CD$_3$OD, 400 MHz): δ 7.72-7.84 (m, 1H), 7.57-7.70 (m, 1H), 7.29-7.46 (m, 4H), 7.17 (d, 2H), 4.76 (s, 2H), 3.98 (s, 1H), 3.43-3.64 (m, 4H), 3.32-3.39 (m, 4H), 1.98 (s, 3H), 1.35 (d, 6H); MS (method 2): m/z 528.0 (M+1); HPLC (method 1): $R_t$ 4.94 minutes.

Following the procedure described above for Example 2 and substituting the appropriate reagents, starting materials and purification methods known to those skilled in the art, the following compounds of the present invention were prepared:

4-(3-Methyl-butyl)-piperazine-1-sulfonic acid (3-methyl-benzo[b]thiophen-2-yl)-(4-trifluoromethoxy-benzyl)-sulfamoyl]-amide, Compound 5. Compound 5 was prepared by substituting valeraldehyde for acetone in Example 2, step B, to afford 34.2 mg as a clear semi-solid. $^1$H-NMR (CD$_3$OD, 400 MHz): δ 7.73-7.86 (m, 1H), 7.54-7.69 (m, 1H), 7.28-7.45 (m, 4H), 7.17 (d, 2H), 4.76 (s, 2H), 3.98 (s, 1H), 3.43-3.64 (m, 4H), 3.32-3.39 (m, 4H), 3.06-3.25 (m, 3H), 1.98 (s, 3H), 1.53-1.74 (m, 3H), 0.98 (d, 6H); MS (method 2): m/z 556.0 (M+1); HPLC (method 1): $R_t$ 5.33 minutes.

4-Methyl-piperazine-1-sulfonic acid (3-methyl-benzo[b]thiophen-2-yl)-(4-trifluoromethoxy-benzyl)-sulfamoyl] amide, Compound 6. Compound 6 was prepared by substituting formaldehyde for acetone in Example 2, step B, to afford 3.6 mg as a clear semi-solid. $^1$H-NMR (CD$_3$OD, 400 MHz): δ 7.75-7.79 (m, 1H), 7.61-7.63 (m, 1H), 7.34-7.41 (m, 4H), 7.16-7.18 (d, 2H), 4.76 (s, 2H), 3.43-3.64 (m, 4H), 3.32-3.39 (m, 4H), 2.92 (s, 3H), 1.98 (s, 3H); MS (method 2): m/z 500.0 (M+1); HPLC (method 1): $R_t$ 5.29 minutes.

Example 3

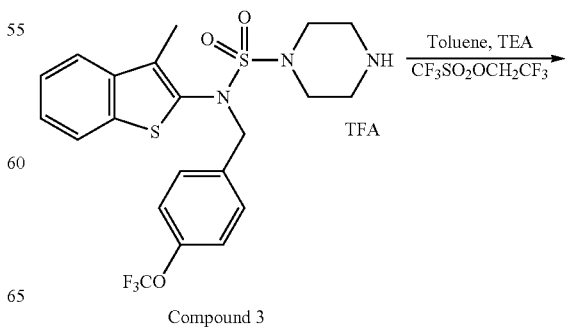

Compound 3

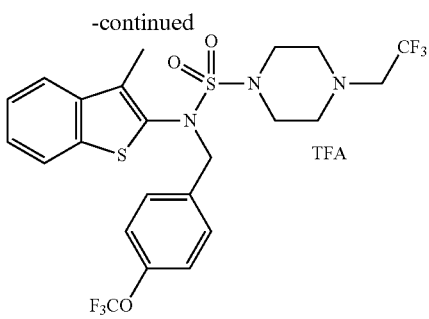

Compound 7

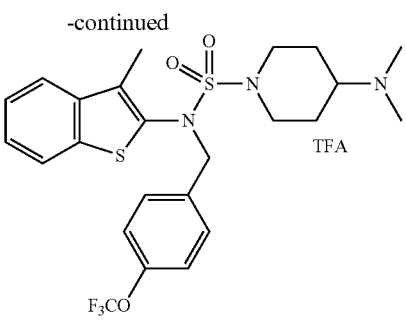

Compound 8

4-(2,2,2-Trifluoro-ethyl)-piperazine-1-sulfonic acid (3-methyl-benzo[b]thiophen-2-yl)-(4-trifluoromethoxy-benzyl)-sulfamoyl]-amide, Compound 7. To a solution of compound 3 (38.4 mg, 0.066 mmol) in toluene (1.0 mL) was added diisopropylamine (14 µL, 0.083 mmol) followed by trifluoromethanesulfonic acid 2,2,2-trilfluoromethyl (30 mg, 0.128 mmol) and the reaction mixture was heated at 82° C. for 18 hours. The reaction mixture was cooled and the solvent evaporated under reduced pressure. The crude reaction mixture purified by reverse-phase semi-prep HPLC (method 3) eluting with a 50% MeCN—H$_2$O (0.1% TFA) to 70% MeCN—H$_2$O (0.1% TFA) gradient to afford 21.8 mg of compound 7 as a white solid. $^1$H-NMR (CD$_3$OD, 400 MHz): δ 7.70-7.86 (m, 1H), 7.60 (m, 1H), 7.26-7.43 (m, 4H), 7.15 (d, 2H), 4.79 (s, 2H), 3.32-3.43 (m, 4H), 3.10 (m, 2H), 2.65-2.81 (m, 4H), 1.96 (s, 3H); MS (method 2): m/z 567.9 (MH$^+$); HPLC (method 1): R$_t$ 7.29 minutes.

Example 4

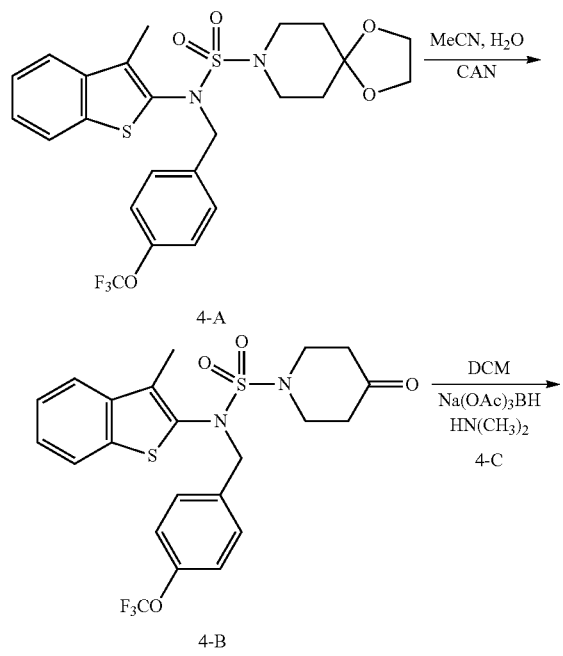

A. 1,4-Dioxa-8-aza-spiro[4,5]decane-8-sulfonic acid (3-methyl-benzo[b]thiophen-2-yl)-(4-trifluoromethoxy-benzyl)-amide (4-A). Compound 4-A was prepared substituting 1,4-dioxa-8-aza-spiro[4,5]decane for piperidine in Example 1, step E, and using the chemistry outlined in steps F to H, to afford 204.1 mg (54%) as a white foam. $^1$H-NMR (CD$_3$OD, 400 MHz): δ 7.74-7.76 (m, 1H), 7.54-7.60 (m, 1H), 7.28-7.37 (m, 4H), 7.13-7.15 (m, 2H), 4.76 (s, 2H), 3.93 (m, 4H), 3.41-3.42 (m, 4H), 1.96 (s, 3H), 1.70-1.73 (m, 4H); MS (method 2): m/z 542.8 (MH$^+$); HPLC (method 1): R$_t$ 6.77 minutes.

B. 4-Oxo-piperidine-1-sulfonic acid (3-methyl-benzo[b]thiophen-2-yl)-(4-trifluoromethoxy-benzyl)-sulfamoyl]-amide (4-B). To a solution of compound 4-A (204.1 mg, 0.376 mmol) in acetonitrile (3.0 mL), heated to 70° C., was added a solution of ceric ammonium nitrate (515.5 mg, 0.94 mmol) in H$_2$O (2.0 mL) and the reaction mixture was heated at 70° C. for 1 hour. The reaction mixture was cooled, diluted with EtOAc, the organic phase washed with H$_2$O, brine, dried over Na$_2$SO$_4$, filtered and the solvent evaporated under reduced pressure. The crude reaction mixture purified by flash column chromatography (SiO$_2$) eluting with 100% heptane to 50% heptane-50% EtOAc to afford 67.9 mg (36%) of compound 4-B as a clear oil. $^1$H-NMR (CDCl$_3$, 400 MHz): δ 7.71-7.75 (m, 1H), 7.57-7.66 (m, 1H), 7.35-7.40 (m, 2H), 7.21-7.27 (m, 2H), 7.04-7.16 (m, 2H), 4.77 (s, 2H), 3.58-3.64 (m, 4H), 2.50-2.53 (m, 4H), 1.99 (s, 3H); MS (method 2): m/z 499.0 (M+1); HPLC (method 1): R$_t$ 6.82 minutes.

C. 4-Dimethylamino-piperidine-1-sulfonic acid (3-methyl-benzo[b]thiophen-2-yl)-(4-trifluoromethoxy-benzyl)-sulfamoyl]-amide, Compound 8. To a solution of compound 4-B (33.9 mg, 0.068 mmol) in dichloromethane (1.0 mL) was added a 2M solution of dimethylamine in THF (4-C) (170 µL, 0.34 mmol) and the reaction mixture was stirred at room temperature for 30 minutes. Sodium triacetoxyborohydride (22 mg, 0.102 mmol) was added and the reaction mixture was stirred for 18 hours. An additional portion of dimethylamine-THF (0.5 mL) and sodium triacetoxyborohydride (22 mg) were added and the reaction mixture stirred at room temperature for an additional 18 hours. The reaction mixture was diluted with dichloromethane, washed with H$_2$O, dried over Na$_2$SO$_4$, filtered, and the solvent evaporated under reduced pressure. The crude reaction mixture purified by reverse-phase semi-prep HPLC (method 3) eluting with a 40% MeCN—H$_2$O (0.1% TFA) to 60% MeCN—H$_2$O (0.1% TFA) gradient to afford 19.2 mg of compound 8 as a clear semi-solid. $^1$H-NMR (CD$_3$OD, 400 MHz): δ 7.73-7.78 (m, 1H), 7.59-7.63 (m, 1H), 7.32-7.39 (m, 4H), 7.15-7.17 (d, 2H), 4.79 (s, 2H), 3.95-3.98 (m, 2H), 2.91-3.13 (m, 2H), 2.84 (m, 7H), 2.07-2.10 (m, 2H), 1.98 (s, 3H), 1.66-1.77 (m, 2H); MS (method 2): m/z 528.0 (M+1); HPLC (method 1): R$_t$ 5.29 minutes.

Following the procedure described above for Example 4 and substituting the appropriate reagents, starting materials and purification methods known to those skilled in the art, the following compounds of the present invention were prepared:

4-Pyrrolidin-1-yl-piperazine-1-sulfonic acid (3-methyl-benzo[b]thiophen-2-yl)-(4-trifluoromethoxy-benzyl)-sulfamoyl]amide, Compound 9. Compound 9 was prepared by substituting pyrrolidine for dimethylamine in Example 4, step B, to afford 13.2 mg as a clear semi-solid. Only one treatment with pyrrolidine was necessary to complete this reaction. $^1$H-NMR (CD$_3$OD, 400 MHz): δ 7.73-7.77 (m, 1H), 7.59-7.62 (m, 1H), 7.32-7.39 (m, 4H), 7.15-7.17 (d, 2H), 4.79 (s, 2H), 3.91-3.94 (m, 3H), 3.42-3.48 (m, 2H), 3.10-3.12 (m, 2H), 2.93-2.96 (t, 2H), 2.14-2.20 (m, 4H), 1.98 (s, 3H), 1.65-1.72 (m, 2H); MS (method 2): m/z 554.0 (M+1); HPLC (method 1): R$_t$ 5.38 minutes.

Example 5

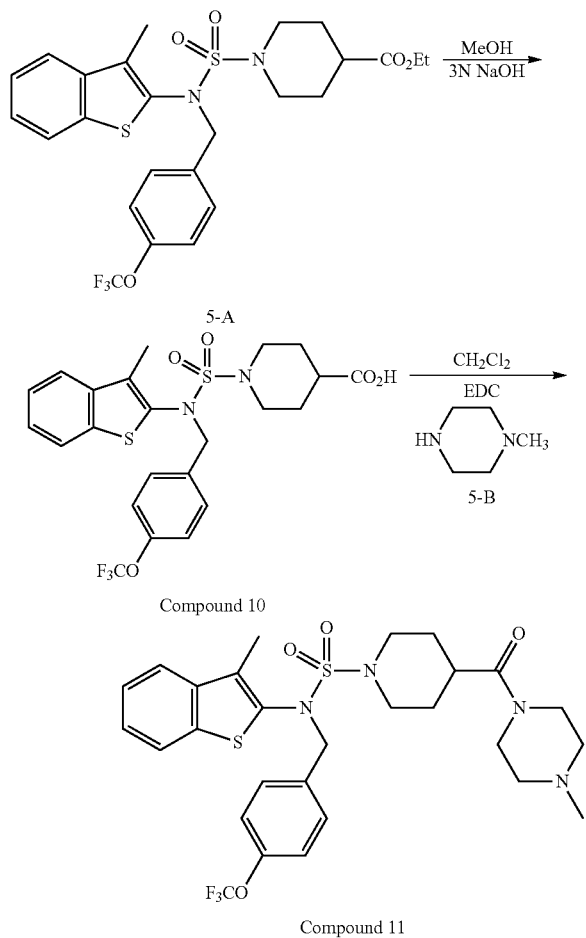

Compound 10

Compound 11

A. 1-[(3-Methyl-benzo[b]thiophen-2-yl)-(4-trifluoromethoxy-benzyl)-sulfamoyl]-piperidine-4-carboxylic acid ethyl ester (5-A). Compound 5-A was prepared by substituting piperidine-4-carboxylic acid ethyl ester for piperidine in Example 1, step E, and using the chemistry outlined in steps F to H, to afford 27 mg (60%) as an oil. $^1$H-NMR (CD$_3$OD, 400 MHz): δ 7.71-7.86 (m, 1H), 7.54-7.61 (m, 1H), 7.29-7.42 (m, 4H), 7.10-7.23 (m, 2H), 4.72-4.85 (br s, 2H), 4.07-4.23 (q, 2H), 3.63-3.79 (m, 2H), 2.95-3.11 (m, 2H), 2.44-2.61 (m, 1H), 1.99 (s, 3H), 1.87-1.96 (m, 2H), 1.60-1.81 (m, 2H), 1.15-1.31 (t, 4H); MS m/z 557.0 (M+1); HPLC (method 1): R$_t$ 7.60 minutes.

B. 1-[(3-Methyl-benzo[b]thiophen-2-yl)-(4-trifluoromethoxy-benzyl)-sulfamoyl]-piperidine-4-carboxylic acid, Compound 10. To a solution of compound 5-A (27 mg, 0.049 mmol), dissolved in MeOH (1.0 mL), was added 3N NaOH (24 µL, 0.073 mmol) and the reaction mixture was refluxed for 18 hours. The reaction was cooled and the solvent evaporated under reduced pressure. The residual solid was partitioned between H$_2$O and EtOAc, the organic layer collected, dried over Na$_2$SO$_4$, filtered and the solvent evaporated under reduced pressure. The crude material was purified by reverse-phase semi-prep HPLC (method 3) eluting with a 50% MeCN—H$_2$O (0.1% TFA) to 70% MeCN—H$_2$O (0.1% TFA) gradient to afford 11.2 mg of compound 10 as a white solid. $^1$H-NMR (CD$_3$OD, 400 MHz): δ 7.71-7.86 (m, 1H), 7.54-7.61 (m, 1H), 7.29-7.42 (m, 4H), 7.10-7.23 (m, 2H), 4.72-4.85 (br s, 2H), 3.63-3.79 (m, 2H), 2.95-3.11 (m, 2H), 2.44-2.61 (m, 1H), 1.99 (s, 3H), 1.87-1.96 (m, 2H), 1.60-1.81 (m, 2H); MS (method 2): m/z 528.9 (MH$^+$); HPLC (method 1): R$_t$ 6.68 minutes.

C. 4-(4-Methyl-piperazine-1-carbonyl)-piperidine-1-sulfonic acid 3-methyl-benzo[b]thiophen-2-yl)-(4-trifluoromethoxy-benzyl)-amide, Compound 11. To a solution of compound 10 (49 mg, 0.093 mmol), dissolved in dichloromethane (2.0 mL), was added EDC (27 mg, 0.139 mmol) and N-methyl-piperazine (5-B) (12 µL, 0.111 mmol) and the reaction mixture stirred for 18 hours. The reaction mixture was diluted with dichloromethane, washed with H$_2$O, dried over Na$_2$SO$_4$, filtered, and the solvent evaporated under reduced pressure. The crude material was purified by reverse-phase semi-prep HPLC (method 3) eluting with a 38% MeCN—H$_2$O (0.1% TFA) to 58% MeCN—H$_2$O (0.1% TFA) gradient to afford 17.6 mg of compound 11 as an oil. $^1$H-NMR (CD$_3$OD, 400 MHz): δ 7.70-7.82 (m, 1H), 7.53-7.67 (m, 1H), 7.27-7.43 (m, 4H), 7.10-7.23 (m, 2H), 4.70-4.84 (br s, 2H), 3.82-3.90 (m, 2H), 3.40-3.65 (m, 3H), 2.89-3.07 (m, 3H), 2.92 (s, 3H), 2.76-2.89 (m, 1H), 1.87-2.00 (m, 4H), 1.63-1.85 (m, 5H); MS (method 2): m/z 611.0 (M+1); HPLC (method 1): R$_t$ 5.24 minutes.

Following the procedure described above for Example 5 and substituting the appropriate reagents, starting materials and purification methods known to those skilled in the art, the following compounds of the present invention were prepared:

1-[(3-Methyl-benzo[b]thiophen-2-yl)-(4-trifluoromethoxy-benzyl)-sulfamoyl]-piperidine-4-carboxylic acid (2-dimethylamino-ethyl)-amide, Compound 12. Compound 12 was prepared by substituting dimethylamino-ethylamine for n-methyl-piperazine in Example 5, step B, to afford 25.0 mg as an oil. $^1$H-NMR (CD$_3$OD, 400 MHz): δ 7.69-7.86 (m, 1H), 7.53-7.67 (m, 1H), 7.28-7.45 (m, 4H), 7.08-7.23 (m, 2H), 4.69-4.83 (br s, 2H), 3.83-3.91 (m, 2H), 3.74-3.83 (m, 2H), 3.46-3.61 (m, 2H), 3.18-3.27 (m, 8H), 2.25-2.45 (m, 1H), 1.90-2.00 (m, 4H), 1.80-1.90 (m, 2H), 1.60-1.80 (m, 2H); MS (method 2): m/z 599.1 (M+1); HPLC (method 1): R$_t$ 5.31 minutes.

Example 6

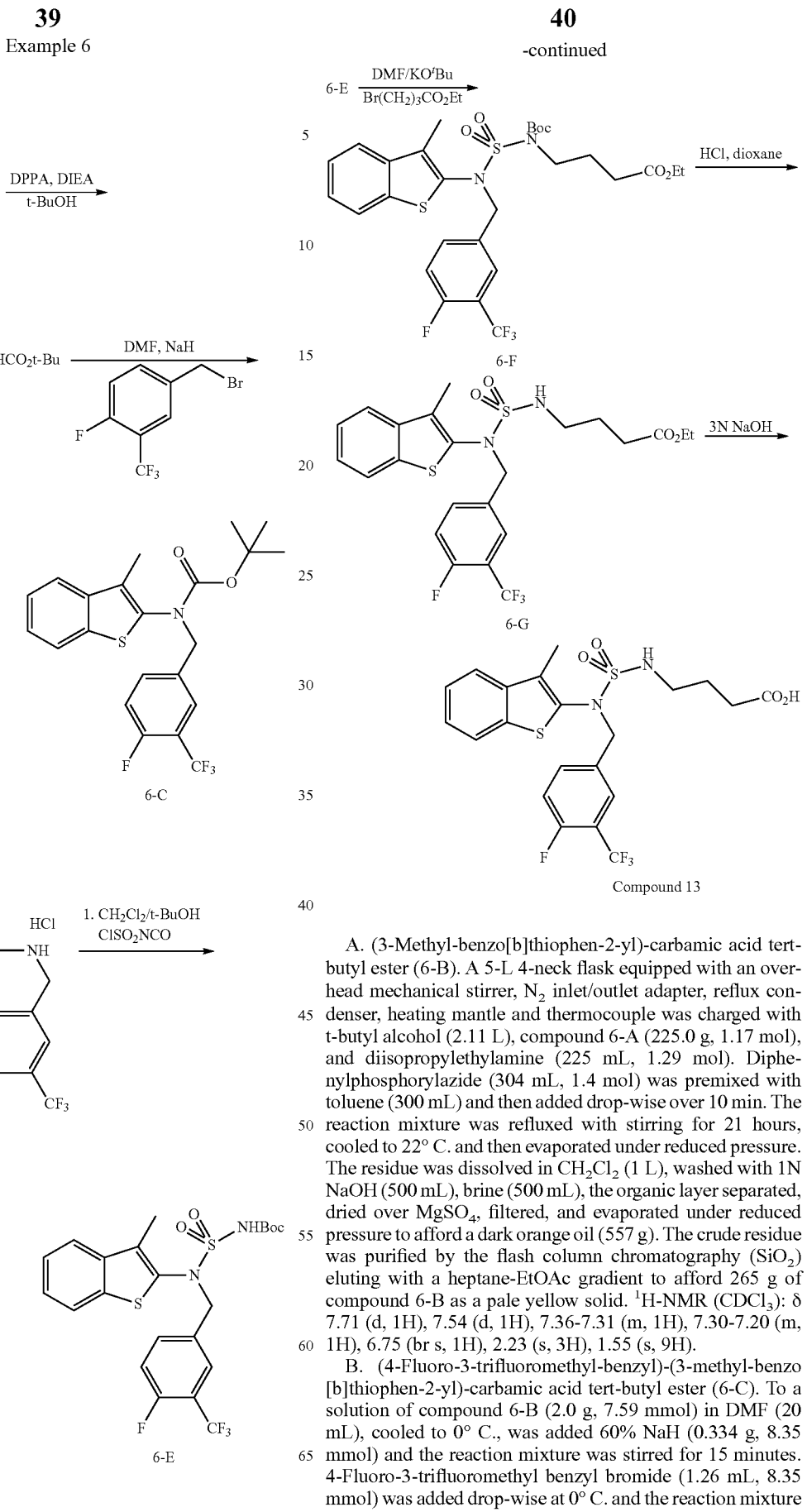

A. (3-Methyl-benzo[b]thiophen-2-yl)-carbamic acid tert-butyl ester (6-B). A 5-L 4-neck flask equipped with an overhead mechanical stirrer, $N_2$ inlet/outlet adapter, reflux condenser, heating mantle and thermocouple was charged with t-butyl alcohol (2.11 L), compound 6-A (225.0 g, 1.17 mol), and diisopropylethylamine (225 mL, 1.29 mol). Diphenylphosphorylazide (304 mL, 1.4 mol) was premixed with toluene (300 mL) and then added drop-wise over 10 min. The reaction mixture was refluxed with stirring for 21 hours, cooled to 22° C. and then evaporated under reduced pressure. The residue was dissolved in $CH_2Cl_2$ (1 L), washed with 1N NaOH (500 mL), brine (500 mL), the organic layer separated, dried over $MgSO_4$, filtered, and evaporated under reduced pressure to afford a dark orange oil (557 g). The crude residue was purified by the flash column chromatography ($SiO_2$) eluting with a heptane-EtOAc gradient to afford 265 g of compound 6-B as a pale yellow solid. $^1$H-NMR ($CDCl_3$): δ 7.71 (d, 1H), 7.54 (d, 1H), 7.36-7.31 (m, 1H), 7.30-7.20 (m, 1H), 6.75 (br s, 1H), 2.23 (s, 3H), 1.55 (s, 9H).

B. (4-Fluoro-3-trifluoromethyl-benzyl)-(3-methyl-benzo[b]thiophen-2-yl)-carbamic acid tert-butyl ester (6-C). To a solution of compound 6-B (2.0 g, 7.59 mmol) in DMF (20 mL), cooled to 0° C., was added 60% NaH (0.334 g, 8.35 mmol) and the reaction mixture was stirred for 15 minutes. 4-Fluoro-3-trifluoromethyl benzyl bromide (1.26 mL, 8.35 mmol) was added drop-wise at 0° C. and the reaction mixture was stirred for 1 hour. The reaction mixture was poured into ice water, extracted with ethyl acetate, the organic phase washed with $H_2O$, brine, dried over $MgSO_4$, filtered, and the solvent evaporated under reduced pressure. The crude oil was purified by flash column chromatography ($SiO_2$) eluting with a 0% EtOAc-heptane to 25% EtOAc-heptane gradient to afford compound 6-C as a clear oil. Compound 6-C was used without further purification in the next step.

C. (4-Fluoro-3-trifluoromethyl-benzyl)-(3-methyl-benzo[b]thiophen-2-yl)-amine hydrochloride (6-D). To compound 6-C was added a solution of 4N HCl in dioxane (20 mL) and the reaction mixture was stirred for 3 hours. The reaction mixture was diluted with ether, the solid filtered, washed with ether, and dried under vacuo to afford 1.86 g of compound 6-D as a white solid. $^1$H NMR ($CD_3OD$, 300 MHz): δ 7.61-7.83 (m, 3H), 7.52 (d, 1H), 7.26-7.39 (m, 2H), 7.10-7.26 (m, 1H), 4.57 (s, 2H), 2.22 (s, 3H); MS (method 2): m/z 340.0 ($MH^+$); HPLC (method 1): $R_t$ 6.78 minutes.

D. N-(4-Fluoro-3-trifluorobenzyl)-N-(3-methyl-benzo[b]thiophen-2-yl)-[N'-tert-butyloxycarbonyl]-sulfonamide (6-E). To a solution of chlorosulfonyl isocyante (0.720 mL, 3.91 mmol) in $CH_2Cl_2$ (7.0 mL), at 0° C., was added t-butanol (0.793 mL, 3.91 mmol) in $CH_2Cl_2$ (4.0 mL) and the reaction was allowed to stir at 0° C. for 30 min. (reaction exotherms upon addition of t-butanol). The prepared solution was then added to a cold (0° C.) solution of compound 6-D (1.47 g, 3.91 mmol) in $CH_2Cl_2$ (7.0 mL) and TEA (1.63 mL, 11.73 mmol), drop-wise, and the reaction mixture was allowed to warm to ambient temperature for 18 hours. The reaction mixture was diluted with EtOAc, washed with 1N HCl, $H_2O$, brine, dried over $Na_2SO_4$, filtered, and the solvent evaporated under reduced pressure. The crude residue was purified by flash column chromatography ($SiO_2$) eluting with a heptane-EtOAc gradient to afford 813 mg of compound 6-E as a white foam. $^1$H-NMR (DMSO-$d_6$, 400 MHz): δ 11.65 (s, 1H), 7.91-7.93 (m, 1H), 7.68-7.62 (m, 2H), 7.61-7.65 (m, 4H), 7.37-7.48 (m, 3H), 5.00 (br s, 2H), 2.01 (s, 3H), 1.52 (s, 9H); MS (method 2): m/z 541.0 (M+Na); HPLC (method 1): $R_t$ 6.79 minutes.

E. N-(4-Fluoro-3-trifluoromethyl-benzyl)-N-(3-methyl-benzo[b]-thiophen-2-yl)-N'-(butyric acid ethyl ester)-N-(tert-butyloxycarbonyl)-sulfonamide (6-F). To a solution of compound 6-E (200 mg, 0.386 mmol) in DMF (2.0 mL), at room temperature, was added a solution of 1.0M KOtBu in THF (0.579 mL, 0.579 mmol), and the suspension was allowed to stir at room temperature for 30 minutes. Ethyl 4-bromobutryate (0.221 mL, 1.54 mmol) was added drop-wise to the reaction mixture and it was allowed to stir for 18 hours. The reaction mixture was incomplete, and $K_2CO_3$ (53 mg) followed by ethyl 4-bromobutyrate (0.1 mL) were added and the reaction mixture was stirred at 65° C. for 18 hours. The reaction mixture was diluted with EtOAc, washed with $H_2O$, brine, dried over $Na_2SO_4$, filtered, and the solvent evaporated under reduced pressure. The crude residue was purified by flash column chromatography ($SiO_2$) eluting with a heptane-EtOAc gradient to afford 186.6 mg of compound 6-F as a viscous oil. MS (method 2): m/z 533.1 ((M-Boc)+1)/655.2 (M+Na); HPLC (method 1): $R_t$ 7.36 minutes.

F. N-(4-Fluoro-3-trifluoromethyl-benzyl)-N-(3-methyl-benzo[b]-thiophen-2-yl)-N'-(butyric acid ethyl ester)-sulfonamide (6-G). To compound 6-F (186 mg, 0.296 mmol) was added a solution of 4N HCl in dioxane (4.0 mL) and the reaction mixture was stirred at room temperature for 24 hours. The solvent was evaporated under reduced pressure, the residue azeotroped with $CH_2Cl_2$ (2×), and the residue dried under vacuo to afford 164.4 mg of compound 6-G as a yellow oil. HPLC (method 1): $R_t$ 6.49 minutes.

G. N-(4-Fluoro-3-trifluoromethyl-benzyl)-N-(3-methyl-benzo[b]-thiophen-2-yl)-N'-(butyric acid)-sulfonamide, Compound 13. To a solution of compound 6-G (164.4 mg, 0.309 mmol) in MeOH (3.0 mL) was added 3N NaOH (0.206 mL, 0.617 mmol) and the reaction mixture was refluxed for 18 hours. The reaction mixture was cooled and the crude residue purified by reverse-phase semi-prep HPLC (method 3) eluting with a 60% $MeCN—H_2O$ (0.1% TFA) to 80% $MeCN—H_2O$ (0.1% TFA) gradient to afford 44.8 mg of compound 13 as a clear oil. $^1$H-NMR (DMSO-$d_6$, 400 MHz): δ 12.09 (s, 1H), 7.99 (m, 1H), 7.83-7.88 (m, 1H), 7.62-7.69 (m, 2H), 7.34-7.45 (m, 3H), 4.76 (s, 2H), 3.07-3.17 (m, 2H), 2.06-2.07 (m, 4H), 1.23-1.77 (t, 2H); MS (method 2): m/z 505.0 (M+1); HPLC (method 1): $R_t$ 6.31 minutes.

Example 7

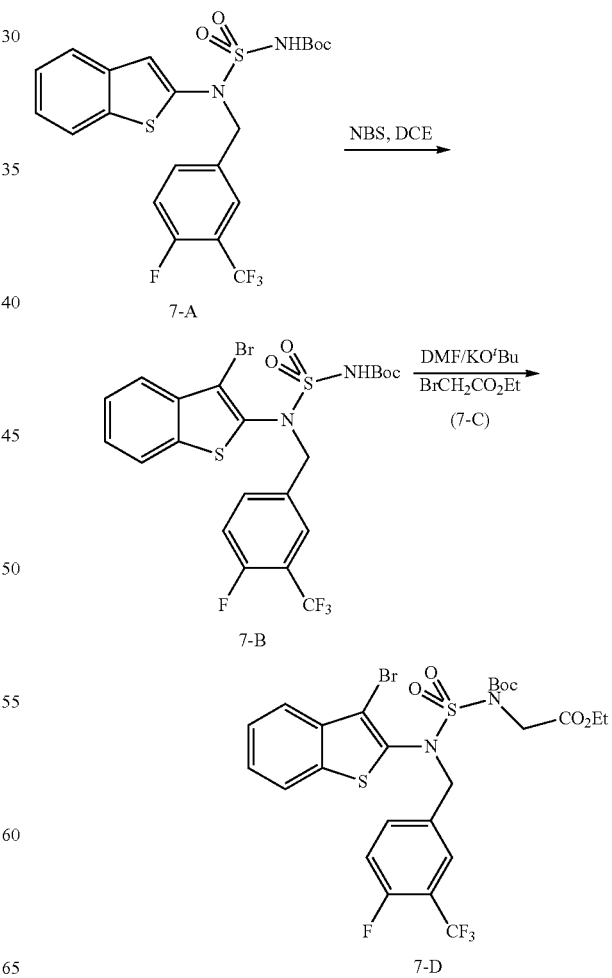

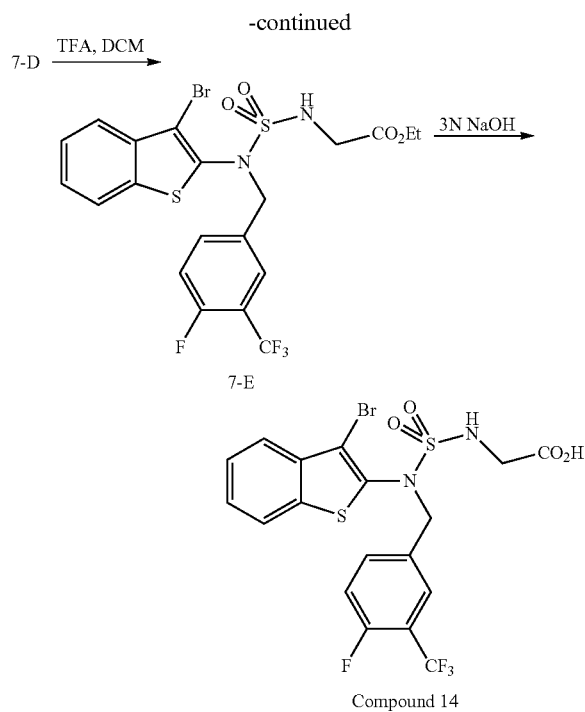

Compound 14

A. N-(4-Fluoro-3-trifluorobenzyl)-N-(benzo[b]thiophen-2-yl)-[N'-tert-butyloxycarbonyl]-sulfonamide (7-A). Compound 7-A was prepared substituting benzo[b]thiophene-2-carboxylic acid for compound 6-A in Example 6, step A, and using the chemistry outlined in steps B to D, to afford 654 mg as an orange oil. $^1$H-NMR (DMSO-$d_6$, 400 MHz): δ 11.76 (s, 1H), 7.87-7.91 (m, 1H), 7.69-7.80 (m, 3H), 7.46-7.51 (t, 1H), 7.33-7.38 (m, 2H), 7.29 (s, 1H), 5.13 (s, 2H), 1.48 (s, 9H); HPLC (method 1): $R_t$ 6.71 minutes.

B. N-(3-Bromo-benzo[b]thiophen-2-yl)-N-(4-fluoro-3-trifluorobenzyl)-[N'-tert-butyloxycarbonyl]-sulfonamide (7-B). To a solution of compound 7-A (654 mg, 1.29 mmol) in DCE (6.0 mL), at room temperature, was added NBS (254 mg, 1.42 mmol), and the reaction was allowed to stir at room temperature for 18 hours. Additional NBS (100 mg) was added and the reaction mixture was stirred at room temperature for 18 hours. The reaction mixture was diluted with EtOAc, washed with H$_2$O, brine, dried over Na$_2$SO$_4$, filtered, and the solvent evaporated. The crude residue was purified by flash column chromatography (SiO$_2$) eluting with a heptane-EtOAc gradient to afford 565 mg of compound 7-B as a brown solid. $^1$H-NMR (DMSO-$d_6$, 400 MHz): δ 11.80 (s, 1H), 8.00-8.03 (m, 1H), 7.70-7.77 (m, 2H), 7.62-7.66 (m, 1H), 7.49-7.54 (m, 2H), 7.41-7.45 (t, 1H), 5.06 (s, 2H), 1.51 (s, 9H); HPLC (method 1): $R_t$ 6.87 minutes.

C. N-(3-Bromo-benzo[b]thiophen-2-yl)-N-(4-fluoro-3-trifluorobenzyl)-[N'-tert-butyloxycarbonyl]-sulfonamide (7-B). To a solution of compound 7-A (654 mg, 1.29 mmol) in DCE (6.0 mL), at room temperature, was added NBS (254 mg, 1.42 mmol), and the reaction was allowed to stir at room temperature for 18 hours. Additional NBS (100 mg) was added and the reaction mixture was stirred at room temperature for 18 hours. The reaction mixture was diluted with EtOAc, washed with H$_2$O, brine, dried over Na$_2$SO$_4$, filtered, and the solvent evaporated. The crude residue was purified by flash column chromatography (SiO$_2$) eluting with a heptane-EtOAc gradient to afford 565 mg of compound 7-B as a brown solid. $^1$H-NMR (DMSO-$d_6$, 400 MHz): δ 11.80 (s, 1H), 8.00-8.03 (m, 1H), 7.70-7.77 (m, 2H), 7.62-7.66 (m, 1H), 7.49-7.54 (m, 2H), 7.41-7.45 (t, 1H), 5.06 (s, 2H), 1.51 (s, 9H); HPLC (method 1): $R_t$ 6.87 minutes.

D. N-(3-Bromo-benzo[b]thiophen-2-yl)-N-(4-fluoro-3-trifluorobenzyl)-(N-acetic acid ethyl ester)-[N'-tert-butyloxycarbonyl]-sulfonamide (7-D). To a solution of compound 7-B (92 mg, 0.158 mmol) in DMF (0.5 mL), at room temperature, was added 60% NaH (8.0 mg, 0.205 mmol), and the suspension was allowed to stir at room temperature for 30 minutes. Bromo acetoacetate (7-C) (21 µL, 0.190 mmol) was added drop-wise to the reaction mixture and it was allowed to stir for 18 hours. The reaction mixture was treated with additional 60% NaH (8 mg) followed by bromo acetoacetate (21 µL) and the reaction mixture was stirred at room temperature for 18 hours. The reaction mixture was diluted with EtOAc, washed with H$_2$O, brine, dried over Na$_2$SO$_4$, filtered, and the solvent evaporated under reduced pressure. The crude residue was purified by flash column chromatography (SiO$_2$) eluting with a heptane-EtOAc gradient to afford 34.6 mg of compound 7-D as a yellow oil. $^1$H-NMR (CD$_3$OD, 400 MHz): δ 7.73-7.82 (m, 2H), 7.67-7.69 (m, 1H), 7.45-7.55 (m, 3H), 7.16-7.21 (t, 1H), 5.15 (s, 2H), 4.23 (s, 2H), 4.12-4.21 (m, 2H), 1.57 (s, 9H), 1.15-1.29 (m, 3H); MS (method 2): m/z 570.6 ((M-Boc)+1); HPLC (method 1): $R_t$ 7.79 minutes.

E. N-(3-Bromo-benzo[b]thiophen-2-yl)-N-(4-fluoro-3-trifluorobenzyl)-(N-acetic acid ethyl ester)-sulfonamide (7-E). To compound 7-D (34.6 mg, 0.052 mmol) was CH$_2$Cl$_2$ (2 mL) followed by TFA (2 mL) and the reaction mixture was stirred at room temperature for 2 hours. The solvent was evaporated under reduced pressure and dried. The crude residue was purified by flash column chromatography (SiO$_2$) eluting with a heptane-EtOAc gradient to afford 23.9 mg of compound 7-E as an oil. MS (method 2): m/z 570.6 (M+1); HPLC (method 1): $R_t$ 6.58 minutes.

F. N-(3-Bromo-benzo[b]thiophen-2-yl)-N-(4-fluoro-3-trifluorobenzyl)-(N-acetic acid)-sulfonamide, Compound 14. To a solution of compound 7-E (23.9 mg, 0.042 mmol) in MeOH (0.5 mL) was added 3N NaOH (21 µL, 0.062 mmol) and the reaction mixture was refluxed for 2 hours. The reaction mixture was cooled and the crude residue purified by reverse-phase semi-prep HPLC (Gemini, C-18 column; 100× 30 mm I.D.; 5µ) eluting with a 55 to 75% MeCN—H$_2$O (0.1% TFA) gradient to afford 9.8 mg of compound 14 as a clear oil. $^1$H-NMR (CD$_3$OD, 400 MHz): δ 7.68-7.79 (m, 3H), 7.54-7.56 (m, 1H), 7.40-7.45 (m, 2H), 7.12-7.17 (m, 1H), 4.00 (s, 2H); MS (method 2): m/z 543.0 (M+1); HPLC (method 1): $R_t$ 5.81 minutes.

Following the procedure described above for Example 7 and substituting the appropriate reagents, starting materials and purification methods known to those skilled in the art, the following compounds of the present invention were prepared:

N-(3-Bromo-benzo[b]thiophen-2-yl)-N-(4-fluoro-3-trifluorobenzyl)-(N-butyric acid)-sulfonamide, Compound 15. Compound 15 was prepared by substituting ethyl 4-bromobutyrate for bromo acetoacetate in Example 7, step B, to afford 17.6 mg as an oil. $^1$H-NMR (CD$_3$OD, 400 MHz): δ 7.38-7.79 (m, 6H), 7.11-7.23 (m, 1H), 5.45 (s, 2H), 2.32-2.41 (m, 2H), 1.75-1.88 (m, 2H); MS (method 2): m/z 570.9 (M+1); HPLC (method 1): $R_t$ 5.91 minutes.

N-(3-Bromo-benzo[b]thiophen-2-yl)-N-(4-fluoro-3-trifluorobenzyl)-(N-hexanoic acid)-sulfonamide, Compound 16. Compound 16 was prepared by substituting ethyl 5-bromovalerate for bromo acetoacetate in Example 7, step B, to afford 17.6 mg as an oil. $^1$H-NMR (DMSO-$d_6$, 400 MHz): δ 12.06 (s, 1H), 8.15-8.18 (m, 1H), 7.94-7.98 (m, 1H), 7.64-7.75 (m, 3H), 7.40-7.51 (m, 3H), 4.81 (s, 2H), 3.02-3.16 (m, 2H), 2.21-2.34 (m, 2H), 1.54-1.55 (m, 4H); MS (method 2): m/z 585.0 (M+2); HPLC (method 1): $R_t$ 6.54 minutes.

Compounds 1 through 16 of Formula (I), shown in Table 1, were prepared according to the Schemes and Examples described herein.

TABLE 1

(I)

[Structure of Formula (I)]

| Cpd No | Y | R¹ | R⁴ | R^B | or, R⁴—N—R^B are taken together to form |
|---|---|---|---|---|---|
| 1 | methyl | 4-trifluoromethoxy phenylmethyl | | | piperidin-1-yl |
| 2 | methyl | 4-trifluoromethoxy phenylmethyl | | | morpholin-4-yl |
| 3 | methyl | 4-trifluoromethoxy phenylmethyl | | | piperazin-1-yl |
| 4 | methyl | 4-trifluoromethoxy phenylmethyl | | | 4-isopropyl-piperazin-1-yl |
| 5 | methyl | 4-trifluoromethoxy phenylmethyl | | | 4-(3-methyl-butyl)-piperazin-1-yl |
| 6 | methyl | 4-trifluoromethoxy phenylmethyl | | | 4-methyl piperazin-1-yl |
| 7 | methyl | 4-trifluoromethoxy phenylmethyl | | | 4-(2,2,2-trifluoroethyl)-piperazin-1-yl |
| 8 | methyl | 4-trifluoromethoxy phenylmethyl | | | 4-(dimethylamino) piperidin-1-yl |
| 9 | methyl | 4-trifluoromethoxy phenylmethyl | | | 4-(pyrrolidin-1-yl) piperidin-1-yl |
| 10 | methyl | 4-trifluoromethoxy phenylmethyl | | | 4-carboxy piperidin-1-yl |
| 11 | methyl | 4-trifluoromethoxy phenylmethyl | | | 4-(4-methylpiperazin-1-ylcarbonyl) piperidin-1-yl |
| 12 | methyl | 4-trifluoromethoxy phenylmethyl | | | 4-(2-dimethylamino-ethylaminocarbonyl) piperidin-1-yl |
| 13 | methyl | 4-fluoro-3-trifluoromethyl phenylmethyl | H | 3-carboxy-propyl | |
| 14 | bromo | 4-fluoro-3-trifluoromethyl phenylmethyl | H | carboxy-methyl | |
| 15 | bromo | 4-fluoro-3-trifluoromethyl phenylmethyl | H | 3-carboxy-propyl | |
| 16 | bromo | 4-fluoro-3-trifluoromethyl phenylmethyl | H | 4-carboxy-butyl | |

BIOLOGICAL EXAMPLES

Example 1

In Vitro Canine TRPM8 Functional Assay

The functional activity of compounds of the formula (I) was determined by measuring changes in intracellular calcium concentration using a $Ca^{2+}$-sensitive fluorescent dye. The changes in fluorescent signal were monitored by a fluorescence plate reader, either a FLIPR™ (Molecular Devices) or FDSS (Hamamatsu). Increases in intracellular $Ca^{2+}$ concentration were readily detected upon activation with icilin.

At 24 hrs prior to assay, HEK293 cells stably expressing canine TRPM8 were seeded in culture medium in black wall, clear-base poly-D-lysine coated 384-well plates (BD Biosciences, NJ, USA) and grown overnight in 5% $CO_2$ at 37° C. On assay day, growth media was removed and cells were loaded with Calcium 3 Dye (Molecular Devices) for 35 min at 37° C., under 5% $CO_2$ and then for 25 min at room temperature and atmosphere. Subsequently, cells were tested for agonist-induced increases in intracellular $Ca^{2+}$ levels using FLIPR™ or FDSS. Cells were challenged with a compound of the Formula (I) (at varying concentrations) and intracellular $Ca^{2+}$ was measured for 5 min prior to the addition of icilin to all wells to achieve a final concentration that produces approximately an 80% maximal response. $EC_{50}$ or $IC_{50}$ values for compounds of the present invention were determined from eight-point dose-response studies. Curves were generated using the average of quadruplicate wells for each data point. The resultant data are displayed in Table 2.

TABLE 2

| Cpd No. | $IC_{50}$ (μM) @ 0.2 (μM) | % Inh @ 0.2 (μM) |
|---|---|---|
| 1 | 0.0036 | 99 |
| 2 | 0.0057 | 100 |
| 3 | | 19 |
| 4 | 0.060 | |
| 5 | 0.071 | |
| 6 | 0.046 | 90 |
| 7 | 0.013 | 100 |
| 8 | | 36 |
| 9 | | 9 |
| 10 | 0.0046 | 101 |
| 11 | | 30 |
| 12 | 0.061 | 70 |
| 13 | 0.062 | 72 |
| 14 | | 33 |
| 15 | 0.018 | 101 |
| 16 | 0.0085 | 101 |

*$IC_{50}$ values are based on single determinations

In Vivo Models

Example 2

Inhibition of Icilin-induced Behaviors in Rodents

Icilin was initially developed as a "super-cooling" compound by Delmar Chemicals Ltd. Subsequently it was shown to be one of the most potent known agonists of TRPM8 (McKemy D D, et al. Nature 2002, 416(6876): 52-8), having an $EC_{50}$=0.2 μM in stimulating calcium ion influx into TRPM8 transfected cells (Behrendt H J et al. Brit J Pharmacol 2004, 141(4): 737-45). Initial in vivo testing of icilin showed it to cause "wet-dog" shakes in rats. Similar shaking or jumping behavior was also evident in mice, rabbits, cats, dogs and monkeys. In humans, icilin produced a sensation of coolness on contact with mucous membranes, cold prickling when 0.1 mg was dropped on the tongue and coldness in the mouth, pharynx and chest lasting 30-60 minutes when 5-10 mg was ingested orally (Wei E T, Seid D A, J Pharm Pharmacol. 1983, 35, 110). The inhibition or reversal of icilin-induced shaking behaviors in rodents provides evidence for the utility of TRPM8 antagonists of the formula (I) in treating or preventing a disease, syndrome, disorder, or condition in a subject in which the disease, syndrome, disorder or condition is affected by the modulation of TRPM8 receptors.

Example 2a

Inhibition of Icilin-induced "Wet-dog" Shakes in Rats

Male Sprague Dawley rats (220-450 g, Charles River Labs, n=6-9/treatment) may be used to evaluate the ability of selected compounds of the formula (I) to block icilin-induced "wet-dog" shakes (WDS). Compounds of the formula (I) may be administered in an appropriate vehicle, such as hydroxypropyl-β-cyclodextrin (HPβCD), methocellulose, 10% Solutol, or $H_2O$, or the like, by the appropriate route, i.p. or p.o., 30-120 minutes before icilin. Icilin may be administered in PEG-400 or 10% solutol/$H_2O$, at 1.0 or 3.0 mg/kg, i.p. and spontaneous "wet-dog" shakes may be counted 10-20 minutes post-icilin.

Example 2b

Reversal of Icilin-induced Behaviors in Rats

Compounds of the present invention capable of inhibiting the onset of icilin-induced "wet-dog" shaking behavior may also be assessed for their ability to reverse an existing icilin-induced "wet-dog" shaking behavior. In this paradigm, icilin-induced shaking is counted for 10 minutes followed by administration of a compound of the present invention in a suitable vehicle such as hydroxypropyl methylcellulose, hydroxypropyl-β-cyclodextrin or 10% Solutol in water. The diminution of shaking behavior is represented as a percent inhibition relative to icilin-induced shakes in the absence of test compound administration, as described by the following formula: % Inhibition=[1−(WDS count following test compound dose/WDS count prior to test compound dose)]×100. The resultant data are shown in Table 3.

TABLE 3

| Cpd No. | Dose (mg/kg) | Route | Post-icilin | % Inhibition |
|---|---|---|---|---|
| 10 | 10 | p.o. | 1 h | 57 |

Example 3

In vivo Model of Subacute Inflammatory Pain: Carrageenan-induced Hyperalgesia

Intraplantar injection of carrageenan into the hind paw of rats causes a robust acute inflammatory response characterized by reddening, swelling and hypersensitivity of the paw to thermal and mechanical stimuli typically peaking 3-6 hours following application and subsiding over the 12-24 hours.

Example 3a

Rat Carrageenan-induced Radiant Heat Hypersensitivity

To assess the effect of test compounds of the formula (I) on inflammatory hyperalgesia, radiant heat response latencies may be evaluated 3 hours following intraplantar carrageenan (Lambda, Type IV, 200 uL) injection into a single hind paw in male Sprague-Dawley rats. The test compound may be administered either 2 hours prior to or 1 hour following carrageenan injection. The intent is to determine whether the compound may prevent or retard the hypersensitivity associated with this inflammogen. Baseline thermal response latencies may be determined prior to any treatment and again 3 hours after carrageenan injection. Percent reversal of hyperalgesia relative to vehicle treatment (% R) may be calculated for both compound treatment paradigms according to the following formula:

% $R$=(Post compound latency−Post vehicle latency)/
((Baseline latency−Post vehicle latency)×100%.

Example 4

In vivo Model for of Chronic Inflammatory Pain: Complete Freund's Adjuvant (CFA)-induced Hyperalgesia Intraplantar injection of complete Freund's adjuvant (CFA) in rodents results in a long-lasting inflammatory reaction, characterized by a pronounced hypersensitivity to both thermal and mechanical stimuli. This hypersensitivity peaks between 24-72 hours following injection and can last for several weeks. To assess whether test compounds of the formula (I) reverse established hypersensitivity, a 100 μL intraplantar injection of CFA (suspended in a 1:1 emulsion of saline and heat-killed *Mycobacterium tuberculosis* in mineral oil) can be injected into a single hind paw of Sprague-Dawley rats (typically males ranging from 150-350 g). This paradigm also may be conducted with a multiple dosing or a prophylactic dosing regime designed to alter the course of hyperalgesia development. This test predicts the analgesic, anti-allodynic and antihyperalgesic effect of numerous effective clinical agents, including acetaminophen, NSAIDS such as aspirin and ibuprofen, and opioids, such as morphine.

Example 4a

CFA-induced Paw Radiant Heat Hypersensitivity

Each rat may be placed in a test chamber on a warm glass surface and allowed to acclimate for approximately 10 minutes. A radiant thermal stimulus (beam of light) may then be focused through the glass onto the plantar surface of each hind paw in turn. The thermal stimulus may be automatically shut off by a photoelectric relay when the paw is moved or when the cut-off time is reached (20 seconds for radiant heat at ~5 Amps). An initial (baseline) response latency to the thermal stimulus may be recorded for each animal prior to the injection of CFA. Twenty-four hours following intraplantar CFA injection, the response latency of the animal to the thermal stimulus may be re-evaluated and compared to the animal's baseline response time. Only rats that exhibit at least a 25% reduction in response latency (i.e., hyperalgesia) are included in further analysis Immediately following the post-CFA latency assessment, test compound or vehicle (usually Solutol, hydroxypropyl methylcellulose, hydroxypropyl beta-cyclodextrin or PEG-400) may be administered i.p. or p.o. to rats. Post-compound treatment withdrawal latencies may be assessed at fixed time intervals, typically 30, 60 and 120 minutes. The percent reversal (% R) of hypersenstivitiy is calculated according to the following formula:

% Reversal=(Treatment Response–CFA Response)/
(Baseline Response–CFA Response)×100.

Example 4b

CFA-induced Paw Cold Hypersensitivity

Prior to intraplantar CFA injection, mice or rats may be placed individually in elevated observation chambers having wire mesh floors. Through the mesh floor a series of three applications of acetone (0.04-0.10 mL/application) may be sprayed onto the bottom of the paw using a multidose syringe device. A positive response can take the form of an abrupt withdrawal and licking of the paw. The cumulative duration of licking may be recorded for each of the three trials which are then averaged to give the individual's response. Twenty-four hours following CFA injection acetone licking durations may be markedly elevated implying a hypersensitivity to cooling. Test compounds of the formula (I) can be assessed for its ability to return acetone-evoked paw licking durations to pre-CFA levels (typically near zero) following systemic administration. Percent inhibition is calculated as follows % Inhibition=[1–(treatment licking duration/vehicle
licking duration)]×100.

Example 5

Chemically-induced Abdominal Irritant Models of Visceral Pain

A chemical irritant (such as acetic acid, kaolin, bradykinin, phenyl-p-(benzo) quinine, bromo-acetylcholine, or zymosan) may be injected in mice intraperitoneally, causing a contraction of the abdominal musculature, which is characterized by an elongation of the body extending through to the hind limbs The number of such responses may be quantitated and may be reduced by pretreatment of analgesic agents, thus forming the basis for a screening test (Collier H O et al. Br J Pharmacol Chemother 1968, 32(2): 295-310). This type of abdominal irritant test has been used to predict the analgesic effect of numerous clinically effective agents, the potency of which in the abdominal irritant test parallels the magnitude of the dose needed in the relief of clinical pain. Such agents include acetaminophen, NSAIDS such as aspirin and ibuprofen, opioids, such as morphine and codeine, and other centrally acting analgesics, such as tramadol.

One modification of the chemically-induced abdmonial irritant model of visceral pain is to pretreat animals with agents known to induce inflammatory responses following intraperitoneal injection (such as LPS, zymosan, or thioglycolate). A small intraperitoneal dose of such an inflammogen, administered hours or days before the acute chemical irritant challenge, has been shown to increase the number of abdominal contractions observed (Ribeiro R A, et al. Eur J Pharmacol 2000, 387(1): 111-8). While some analgesic agents are effective at mitigating acute viscerochemical nociception, others, particularly those dependent upon receptor induction are more effective at preventing or reversing the enhancement of behavioral responses caused by a preconditioning inflammatory stimulus. Because of the up-regulation of the TRPM8 receptor in inflammation, TRPM8 antagonists that are effective at reducing the mean number of contractions are predicted to provide analgesic action in human clinical use.

The ability of compounds of the formula (I) to mitigate chemical irritant-induced abdominal contractions following a pre-conditioning inflammatory stimulus may be studied as follows. Thioglycolate (3%, w/v, 2-3 mL i.p.) may be injected into male CD1 mice (20-40 g, Charles River Labs), at a maximum dosage volume of 80 mL/kg, to induce peritoneal inflammation. Following a twenty-four hour pre-inflammation period these mice may be dosed orally with compounds of the formula (I) (30 mg/kg; n=10) or vehicle (HPMC with 2% Tween80; n=9) and then one hour later subjected to an abdominal irritant challenge of acetic acid (1%, 10 mL/kg, i.p.). Immediately following injection of acetic acid, mice may be placed individually in glass bell jars (approximately 15 cm in diameter) for counting of abdominal contractions over the next 15 minutes. The total number of abdominal contractions may be summed for each treatment group and employed in the following formula to calculate Percent Inhibition (% I):

% I=[1–(test compound contractions/vehicle contractions)]×100.

Example 6

In vivo Models of Neuropathic Pain

The sciatic nerve is the major sensorimotor innervation of the (hind) leg and foot. Injury to the sciatic nerve or its constituent spinal nerves often results in pain-related behaviors. In rats and mice, tight ligation of the L5 spinal nerve with silk suture, partial tight ligation of the sciatic nerve with silk suture or loose ligation of the sciatic nerve with chromic gut suture each result in behaviors reminiscent of neuropathic pain in humans. These lesions (one per animal) may be performed surgically in anesthetized rodents. Both the spinal nerve and sciatic nerve lesions result in allodynia, a painful response to normally innocuous stimuli, and hyperalgesia, an exaggerated response to normally noxious stimuli. It is important to note that both of these pain-related behaviors may be evoked by the testing procedures and that normal use of the paw (e.g., walking) is relatively uncompromised, apart from occasional "guarding" of the paw. Subsequent to the surgery, the subjects' behaviors, such as grooming, feeding, and weight gain, are normal, except for hypersensitivity (as defined above) of the affected paw.

In addition to induction by nerve damage resulting from accidental trauma or surgical procedures, neuropathic pain can also be induced by diabetes (Fox, A et al., Pain 81:307-316, 1999) or by treatment with chemotherapeutic agents, such as paclitaxel or vincristine (Yaksh, T L et al., Pain 93:69-76, 2001).

Agents that attenuate neuropathic pain in the clinic also are effective in rodent neuropathic pain models. These agents include the recently approved Cymbalta (Duloxetine, Iyengar, S., et al., JPET 2004 311:576-584), morphine (Suzuki, R et al., Pain 1999 80:215-228) and gabapentin (Hunter, J C et al., Eur J Pharmacol 1997 324:153-160). The dual TRPV1/TRPM8 receptor antagonist BCTC reduced mechanical hyperalgesia and tactile allodynia in the chronic constriction injury rodent neuropathic pain model (Pomonis, J D et al., JPET 2003 306:387-393; Behrendt, H et al., Brit J Pharm 2004 141:737). Cold allodynia is a particularly debilitating symptom of neuropathic pain conditions (Jorum E et al. Pain 2003 101: 229-235). The antiallodynic effect of compounds of the formula (I) in this rodent model is predictive of clinical effect for these novel agents.

Example 6a

Chronic Constriction Injury (CCI)-induced Model of Neuropathic Pain—Acetone-induced Hypersensitivity Male Sprague Dawley rats (225-450 g; n=5-8/treatment) may be used to evaluate the ability of selected compounds of the formula (I) to reverse CCI-induced cold hypersensitivity. Four loose ligatures of 4-0 chromic gut may be surgically placed around the left sciatic nerve under inhalation anesthesia as described by Bennett et al (Bennett G J, Xie Y K. *Pain* 1988, 33(1): 87-107). Fourteen to 35 days following CCI surgery, subjects may be placed in elevated observation chambers containing wire mesh floors and five applications of acetone (0.05 mL/application separated by approximately 5 minutes) may be spritzed onto the plantar surface of the paw using a multidose syringe. An abrupt withdrawal or lifting of the paw may be considered as a positive response. The number of positive responses may be recorded for each rat over the five trials. Following baseline withdrawal determinations, compounds of formula (I) may be administered in an appropriate vehicle, such as hydroxypropyl-β-cyclodextrin (HP-βCD), methylcellulose, Methocel, 10% Solutol, or $H_2O$, or the like, by the appropriate route, i.p. or p.o. The number of withdrawals may be redetermined 1 to 3 h after compound administration. Results may be presented as a percent inhibition of shakes, which was calculated for each subject as [1−(test compound withdrawals/pre-test withdrawals)]×100 and then averaged by treatment.

Example 6b

Chronic Constriction Injury (CCI)-induced Model of Neuropathic Pain—Cold Plate-induced Hypersensitivity In male SD rats (175-325 g), four loose ligatures of 4-0 chromic gut may be surgically placed around the left sciatic nerve under inhalation anesthesia as described by Bennet et al (Bennett G J, Xie Y K. *Pain* 1988, 33(1): 87-107). Seven to 21 days following sciatic chronic constriction injury (CCI) surgery, the subjects can be placed onto a commercial cold plate device cooled by peltier elements such that the surface temperature is held at 1° C. Each subject can undergo a 6 minute conditioning period followed by a 3 minute assessment period during which the total duration of hind paw lifting is recorded. This procedure is repeated at several intervals prior to and following systemic drug administration. Compounds of the formula (I) can be assessed for their ability to return duration of paw lifting back to pre-lesion levels. The duration of paw lifting during the 3 minute test period following administration of test compound is taken as a percentage of the duration of paw lifting during the 3 minute test period prior to test compound treatment.

Example 6c

Chronic Constriction Injury (CCI)-induced Model of Neuropathic Pain—Mechanical Allodynia (Von Frey Test)

In male SD rats (175-325 g), four loose ligatures of 4-0 chromic gut may be surgically placed around the left sciatic nerve under inhalation anesthesia as described by Bennet et al (Bennett G J, Xie Y K. *Pain* 1988, 33(1): 87-107). Seven to 21 days following sciatic chronic constriction injury (CCI) surgery, the subjects can be placed onto an elevated rack of plexigas chambers having wire mesh or another type of perforated flooring. The measurement of mechanical allodynia can be performed using the von Frey hairs (Semmes-Weinstein Monofilaments, Stoelting Co., IL) wherein the rats can be habituated to the wire mesh bottom cages before the start of the experiment. Static allodynia can be tested in the unrestrained rats by touching the plantar surface of the hind paw with von Frey hairs in ascending order of force (1.2, 1.5, 2.0, 3.6, 5.5, 8.5, 12, 15, 29, and 76 g) for up to 6 s or until a paw withdrawal response can be elicited. The lowest amount of force required to elicit a response can be recorded as the withdrawal threshold in log g. This procedure is repeated at several intervals prior to and following systemic drug administration. Compounds of the formula (I) can be assessed for their ability to return the threshold force which elicits paw lifting back to pre-lesion levels.

Example 7

Inflammatory Agent-induced Models of Pyresis/Antipyresis

Compounds of the formula (I) can be tested in animal models of pyresis, according to previously documented and validated methods, such as those described by Kozak et al (Kozak W, Fraifeld V. *Front Biosci* 2004, 9: 3339-55). Fever is a frequent accompaniment of inflammatory disease. Animal models make use of the pyretic properties of yeast and other inflammatory agents, injecting a yeast suspension or other agent subcutaneously (Tomazetti J et al. *J Neurosci Methods* 2005, 147(1): 29-35); Van Miert A S, Van Duin C T. *Eur J Pharmacol* 1977, 44(3): 197-204). For example, Male Wistar rats (75-100 g) can be housed in groups of four to a cage at controlled temperature (23±1° C.) with a 12 h light: 12 h dark cycle (lights on at 07:00 h) and with standard lab chow and tap water ad libitum. All measured temperatures can be taken between 08:00 and 19:00 h. Each animal can be used in only one study. Rectal temperature (TR) can be measured by inserting a lubricated thermistor probe (external diameter: 3 mm) 2.8 cm into the rectum of the animal. The probe can be linked to a digital device, which displayed the temperature at the tip of the probe with a 0.1° C. precision and logs the values over time. Immediately after measuring the initial basal rectal temperature, the animals can be injected with commercially available dried baker yeast (*Saccharomyces cerevisiae*) suspended in pyrogen-free 0.9% NaCl (0.05-0.25 g/kg, i.p.) or 0.9% NaCl (10 ml/kg). TR changes can be recorded every hour up to 12 h, and expressed as the difference from the basal value. Since it has been previously reported that handling and temperature measuring-related stress alter rectal temperature, these animals can be habituated to the injection and measuring procedure for 2 days before experiments are carried out. In these sessions, the animals can be subjected to the same temperature measuring procedure described above, and can be injected intraperitoneally (i.p.) with 0.9% NaCl (10 ml/kg).

To assess the effect of potential antipyretic compounds on basal rectal temperature study animals can have their TR measured for 4 h, and after the fourth TR measurement they can be subcutaneously (s.c.) injected with vehicle (such as 10% Solutol in sterile water 5 ml/kg) or compounds of the formula (I) prepared in vehicle. TR can then be recorded every hour up to 8 h after the compound injections. To assess the effect of compounds of the formula (I) on baker yeast-induced hyperthermia, study animals can have their basal TR measured and then be injected with a pyrogenic dose of baker yeast (for example, 0.135 g/kg). TR changes can be recorded every hour up to 4 h, when potential antipyretics agents such as those compounds of the formula (I) are administered. Rectal temperature can then be monitored over the following 8 h. Basal rectal temperature and changes in rectal temperature can be expressed as means±S.E.M. of the differences from TR at 07:00 h. Data can be analyzed by two-way analysis of variance (ANOVA), with time of measures treated as within subject factor, depending on the experimental design. Post hoc analysis can be carried out by the F-test for simple effect and the Student-Newman-Keuls test, when appropriate. A value of $P<0.05$ would be considered statistically significant.

The modification of the subsequent pyretic response by therapeutic agents can also be monitored by rectal telemetry or other measurements of body temperature. Several clinically relevant agents such as acetaminophen, aspirin and ibuprofen, reduce fever in these models. The antipyretic effect of TRPM8 antagonists, such as compounds of the formula (I), in these tests would also be predictive of their clinical effect.

Example 8

CFA-induced Model of Rheumatoid Arthritis

Compounds of the formula (I) can be tested in animal models of rheumatoid arthritis, according to previously documented and validated methods, such as those described by Nagakura et al (Nagakura Y, et al. *J Pharmacol Exp Ther* 2003, 306(2): 490-7). For example, arthritis can be induced by the CFA inoculation in the rats (Male Lewis rats150-225 g; Charles River). Briefly, 100 mg of *Mycobacterium butyricum* (Difco, Detroit, Mich.) can be thoroughly mixed with 20 mL of paraffin oil. Then mixture can be autoclaved for 20 min at 120° C. Each rat can be injected in the right footpad (hind paw) with the mixture in a 0.1-mL volume under inhalation anesthesia. The rats serving as controls can be injected with 0.1 mL of saline. Pain and other disease development parameters can be measured in the CFA- or saline-treated rats just before inoculation and up to 28 days post-inoculation. The measurement for pain parameters can be conducted for both mechanical and thermal (hot or cold) endpoints. The measurement of mechanical allodynia can be performed using the von Frey hairs (Semmes-Weinstein Monofilaments, Stoelting Co., IL) wherein the rats can be habituated to wire mesh bottom cages before the start of the experiment. Static allodynia can be tested in the unrestrained rats by touching the plantar surface of the hind paw with von Frey hairs in ascending order of force (1.2, 1.5, 2.0, 3.6, 5.5, 8.5, 12, 15, 29, and 76 g) for up to 6 s or until a paw withdrawal response can be elicited. The lowest amount of force required to elicit a response can be recorded as the withdrawal threshold in log g. Thermal hyperalgesia can be assessed using the radiant heat test wherein a mobile radiant heat source can be located under a glass surface upon which the rat is placed. The beam of light can be focused on the hind paw, and the paw withdrawal latencies are defined as the time taken by the rat to remove its hind paw from the heat source. The measurement of joint hyperalgesia can be performed by a modification of the previously reported method (Rupniak N M J et al. *Pain* 1997, 71: 89-97). The torso of each rat can be held from the back with the left palm, and the bending and extension (one after the other and five times in each direction) of the ankle within its limits of range of motion can be performed with the right fingers. The total number of vocalizations emitted after the manipulation (the bending and extension, five times in each direction) can be recorded for each paw (the maximum score is 10 for each paw).

The scoring of mobility can be performed by modifying the evaluation scale reported by Butler et al. (Butler S H et al *Pain* 1992, 48: 73-81): score 6, walks normally; score 5, walks being protective toward the ipsilateral hind paw (touches the ipsilateral hind paw fully on the floor); score 4, walks being protective toward the ipsilateral hind paw (touches only the toe of the ipsilateral hind paw on the floor); score 3, walks being protective toward both hind paws (touches the contralateral hind paw fully on the floor); score 2, walks being protective toward both hind paws (touches only the toe of the contralateral hind paw on the floor); score 1, crawls only using the fore paws; and score 0, does not move. Paw volumes can be measured by volume displacement of electrolyte solution in a commercially available plethysmometer device. The hind paw can be immersed to the junction of the hairy skin, and the volumes can be read on a digital display. The scoring of joint stiffness can be performed as follows: the body of rats can be held from the back with the left palm, and the bending and extension (once in each direction) of the ankle within its limits of range of motion can be performed with the right fingers. It can be confirmed beforehand that there is no restriction of ankle joint movement in the bending and extension manipulations in naive rats, and the scoring can be performed according to the evaluation scale reported by Butler (Butler S H et al *Pain* 1992, 48: 73-81): score 2, there are restrictions of full range of movement of the ankle in both bending and extension; score 1, there is a restriction of full range of movement of the ankle in bending or extension; and score 0, no restriction. The measurements for paw volume and joint stiffness can be conducted for both hind paws.

Compounds of the formula (I) can be assessed for antihyperalgesic efficacy as follows: thirty-two rats (8 rats per dose and four doses per compound) that are be treated with the CFA and another eight rats as naive controls can be used for each drug evaluation. The analgesic effects can be evaluated on post-inoculation day 9, when mechanical allodynia, thermal hyperalgesia, joint hyperalgesia, and joint stiffness in the ipsilateral paw reached almost the maximum, although those parameters in the contralateral paw changed only slightly and the systemic disturbance shown by the change of mobility score is small. On the day before evaluation, body weight, mechanical allodynia, thermal hyperalgesia, and joint hyperalgesia can be measured for the 32 rats that are to be used for compound evaluation. The rats are allocated to four groups (eight rats per group) such that the differences in the averages of those parameters among the groups became small. All the analgesic effect evaluations and behavioral observations can be carried out by the observer who is blind to the drug treatment.

Data can be expressed as the mean+/−S.E.M. The time-course curves for mechanical allodynia, thermal hyperalgesia, joint hyperalgesia, body weight, and paw volume can be subjected to two-way repeated measures analysis of variance with post hoc t test. In experiments for evaluation of compounds of formula (I), the difference in scores between the vehicle-treated and naive control groups can be analyzed by Student's t test to confirm significant changes in the pain parameters in the ipsilateral paw. The analgesic effects can be analyzed by Dunnett's t test, and in each case the drug-treated groups can be compared with the vehicle-treated group. In each statistical analysis, the comparison can be conducted for paws on the corresponding side. $P<0.05$ is considered statistically significant. In this model, the centrally acting analgesics morphine and tramadol fully relieved pain, whereas the NSAIDs, indomethacin and diclofenac are partially effective, evidencing the model's clinical predictability. The analgesic effect of compounds of the formula (I) in this test would predict their clinical usefulness in treating arthritis.

Example 9

In vivo Model for Arthritis: Inflammogen-induced Hyperalgesia of the Knee Joint

Compounds of the formula (I) can be tested in animal models of osteoarthritis, according to previously documented and validated methods, such as those described by Sluka et al (Sluka K A, Westlund K N. *Pain* 1993, 55(3): 367-77). For example, male Sprague-Dawley rats (Harlan, Indianapolis, Ind.) weighing 225 to 350 g can be briefly anesthetized with vaporized halothane and then injected with a mixture of 3% carrageenan and 3% kaolin (100 µL in 0.9% sterile saline) into the joint cavity of one knee. After the injection, the animals can be returned to their cages until the time of testing. For behavioral testing animals can be placed in individual clear plastic cages on top of an elevated wire mesh surface that restricted movement. The animals should be allowed to acclimate for approximately 1 hour before testing. Von Frey filaments, as described above, can then be used to test for enhanced responses to mechanical stimuli. The filaments can be successively applied through the wire mesh perpendicularly to the plantar surface in between the pads of the third and fourth phalanges. The response threshold to mechanical stimuli can be determined before inflammation of the knee joint; 4 hours after inflammation to confirm the development of hyperalgesia; immediately after the administration of test compound such as those of Formula (I) i.e. 5 hours after inflammation; and at 8, 12, and 24 hours after inflammation.

The Kruskal-Wallis test, a nonparametric test, can be used to analyze the effects for frequency, intensity, and group for response to mechanical stimuli at baseline, 4 hours after inflammation, and after compound treatment (5 hours, 8 hours, 12 hours, and 24 hours after inflammation). Further post hoc testing between groups can be executed by using the Mann-Whitney signed rank test. The data can be presented as median with 25th and 75th percentiles. Significance is $P \leq 0.05$.

Additionally, the gait of the animal or other pain-related behavior can be scored as the dependent measure of the painful effect of the arthritis on the animal's activity (Hallas B, Lehman S, Bosak A, et al. *J Am Osteopath Assoc* 1997, 97(4): 207-14). The effect of test drug on the animal's normal behavior can be quantified from zero, meaning no response, to three for incapacitating impairment. Effective analgesic treatment includes the clinically used indomethacin (Motta A F, et al. *Life Sci* 2003, 73(15): 1995-2004). Thus the benefit of compounds of the formula (I) in this model would predict their clinical relevance.

Example 10

Sarcoma Cell-induced Models of Bone Cancer Pain

Compounds of the formula (I) can be tested in animal models of bone cancer pain, according to previously documented and validated methods, such as those described in the scientific literature (El Mouedden M, Meert T F. *Pharmacol Biochem Behav* 2005, 82(1): 109-19; Ghilardi J R, et al. *J Neurosci* 2005, 25(12): 3126-31). In preparation for cell inoculation and tumor induction, osteolytic murine sarcoma cells (NCTC 2472, American Type Culture Collection (ATCC), Rockville, Md., USA) can be cultured in NCTC 135 medium (Invitrogen) containing 10% horse serum (Gibco) and passaged 2 times weekly according to ATCC guidelines. For their administration, cells can be detached by scraping and then centrifuged at 1000×g. The pellet can be suspended in fresh NCTC 135 medium ($2.5 \times 10^6$ cells/20 µL) and then used for intramedullary femur inoculation. Male C3H/HeN-Crl mice (25-30 g, Charles River Labs) can be used in such experiments. After induction of general anesthesia with xylazine (10 mg/kg i.p.) and ketamine (100 mg/kg i.p.) the left hind paw can be shaved and disinfected with povidone-iodine followed by 70% ethanol. A superficial incision of 1 cm can then be made over the knee overlaying the patella. The patellar ligament can then be cut, exposing the condyles of the distal femur. A 23-gauge needle can be inserted at the level of the intercondylar notch and the intramedullary canal of the femur to create a cavity for injection of the cells. Twenty microliters of media (sham animals) or media containing tumor cells (approximately $2.5 \times 10^6$ cells) can then be injected into the bone cavity using a syringe. To prevent leakage of cells outside the bone, the injection site can be sealed with dental acrylic and the wound closed with skin stitches.

Pain behaviors can be evaluated in separate groups (n=6) of sham and bone tumor mice with confirmed hyperalgesia as assessed by spontaneous lifting behavior. Animals can be behaviorally tested during a 3-week period prior to and after tumor inoculation. Body weight of the mice can be recorded throughout the experimental period to help monitor general health status. To measure the spontaneous lifting, the animals can be habituated in a transparent acrylic cylinder of 20 cm diameter put on an horizontal surface and thereafter observed during 4 min for spontaneous lifting behavior of the left hind paw. After spontaneous lifting behavior assessment, animals can be immediately placed on a mouse rotarod (e.g. ENV-575M\, Med Associates Inc., GA, USA) at a speed of 16 rpm for 2 min wherein limb-use during forced ambulation is scored: 4=normal; 3=limping; 2=partial non-use of left hind paw; 1=substantial non-use of left hind paw; 0=non-use of left hind paw. Assessment of cold allodynia may be made by exposing the ipsilateral hind paw of the mouse to 5 repeated applications of acetone (20 µL) and quantifying the lift/licking frequency and/or duration. Post-mortem evaluation of bone destruction can be assessed by ACT processing followed by scanning using a system such as the Skyscan 1076 microtomograph system for small animal imaging (Skyscan 1076\, Skyscan, Aartselaar, Belgium). Measured histomorphometry parameters of bone destruction can be subsequently correlated with behavioral endpoints.

The antihyperalgesic, antiallodynic and disease modifying effects of compounds of the formula (I) can be tested in this murine model of bone cancer pain in separate groups (n=6 per dose group). Animals with confirmed hyperalgesia, as assessed by spontaneous or acetone-evoked lifting, can be behaviorally tested, for example, on days 15 and 22 after distal femur tumor inoculation before and 1 h after systemic administration of vehicle (e.g. 20% HPbCD in sterile water) or compounds of the formula (I). The statistical analysis can be performed by one-way ANOVA to compare behavioral measurements and bone parameters among the experimental groups. To compare behavioral measurements and bone parameters between sham and tumor-bearing animals, a Mann-Whitney U test can be used. Results are considered statistically significant at $P < 0.05$ (two-tailed). Data are expressed as mean+/−S.E.M.

Bone cancer causes intense pain in humans, mimicked in animal models of bone cancer pain in rodents such as that described above. Analgesic treatments that are effective in this model include COX-2 inhibitors (Sabino M A, Ghilardi J R, Jongen J L, et al. *Cancer Res* 2002, 62(24): 7343-9) and high doses of morphine (Luger N M et al. *Pain* 2002, 99(3): 397-406), agents used clinically for pain relief in patients experiencing bone cancer pain. Because this model so closely mimics the human disease state, the finding that cold allodynia is a prominent symptom (Lee, Seong et al. *Yonsei Med J* 2005, 46(2): 252-9) strongly supports the concept that TRPM8 antagonists of the present invention will provide relief of pain associated with human bone cancer.

Example 11

Respiratory Irritant-induced Models of Cough

Compounds of the formula (I) can be tested in animal models of antitussive activity, according to previously documented and validated methods, such as those described by: Tanaka, M. and Maruyama, K. *J Pharmacol. Sci* 2005, 99(1), 77-82; Trevisani, M. et al., *Throax* 2004, 59(9), 769-72; and Hall, E. et al., *J Med. Microbiol.* 1999, 48: 95-98. Testing is conducted in transparent ventilated chambers with a constant airflow of 400 mL/min. The tussive agent (citric acid 0.25 M or capsaicin 30 mM) can be nebulised via a miniultrasonic nebuliser with an output of 0.4 mL/min. The appearance of cough can be detected by means of a tie clip microphone and confirmed by the characteristic posture of the animal. The cough sounds can be recorded and digitally stored. A blinded observer subsequently counts the number of elicited cough efforts. In some cases, animals can be sensitized by pre-exposure to certain agents such as ovalbumin. A test compound can be administered to at the peak of irritant-induced cough to evaluate the antitussive effects of the compound. In addition, prophylactic or multiple dosing regimes can be utilized to evaluate the test compound for modulation of the onset and duration of irritant-induced cough. Variations of these tests predict the antitussive effects of effective clinical agents, including NMDA antagonists such as dextrorphan and dextromethorphan, opioids such as codeine, beta 2 agonists such as salbutamol and antimuscarinics such as ipratropium (Bolser, D. C. et al., *Eur J Pharmacol* 1995, 277(2-3), 159-64; Braga, P. C. *Drugs Exper Clin Res* 1994, 20, 199-203). The antitussive action of menthol in both guinea pig and humans Eccles R. *Curr Allergy Asthma Rep* 2003, 3(3): 210-4; Laude E A, et al. *Pulm Pharmacol* 1994, 7(3): 179-84; Morice A H, et al. *Thorax* 1994, 49(10): 1024-6) is predictive of the clinical utility of compounds of the formula (I) as antitussive agents.

Example 12

Chemical Irritant-induced Models of Itch, Contact Dermatitis, Eczema and Other Manifestations of Dermal Allergy, Hypersensitivity and/or Inflammation Compounds of the formula (I) can be tested in animal models of contact dermatitis or itch, according to previously documented and validated methods, such as those described in the scientific literature (Saint-Mezard P et al. *Eur J Dermatol* 2004, 14(5): 284-95; Thomsen J. S., et al. *J Exp Dermatol* 2002, 11(4): 370-5; Weisshaar E, et al. *Arch Dermatol Res* 1998, 290(6): 306-11; Wille J J, et al. *Skin Pharmacol Appl Skin Physiol* 1999, 12(1-2): 18-27). Mice (or species such as guinea pig or rat) can be sensitized with 25 mL of 0.5% dinitrofluorobenzene solution (DNFB diluted 4:1 in acetone:olive oil immediately before application or other haptens, such as 12-myristate-13 acetate, picryl chloride, oxazolone, capsaicin, arachidonic acid, lactic acid, trans-retinoic acid or sodium lauryl sulfate) painted to the shaved dorsal skin or untreated (controls). Five days later, 10 mL of 0.2% DNFB a nonirritant dose) can be applied onto both sides of the right ear and the same amount of solvent alone onto the left ear. Ear thickness can be monitored daily using a caliper. Compounds of the formula (I) can be administered at the peak of inflammation to evaluate the anti-allergy activity of compounds. In addition, prophylactic or multiple dosing regimes can be utilized to evaluate the test compound for modulation of the onset and duration of anti-allergy activity. Variations of these tests can predict the anti-allergy and itch activity of effective clinical agents. The ability of these models to predict the therapeutic effect of compounds in human dermal conditions is supported by the cross-species ability of serotonin to induce itch (Weisshaar E, Gollnick H. *Skin Therapy Left* 2000, 5(5): 1-2, 5). Additionally, the contact sensitizing property of commercially important drugs and the ability of ion channel modulators to prevent and treat skin sensitization in these models (Kydonieus A, et al., *Proceedings of the International Symposium on Controlled Release of Bioactive Materials* 24$^{th}$: 23-24, 1997) demonstrate the therapeutic utility of compounds of the formula (I) in dermal sensitization.

Example 13

Chemical Irritant-induced Models of Rhinitis and Other Manifestations of Nasal Hypersensitivity and/or Inflammation Compounds of the formula (I) can be tested in animal models of rhinitis, according to previously documented and validated methods, such as those described in the scientific literature (Hirayama Y, et al. *Eur J Pharmacol* 2003, 467(1-3): 197-203; Magyar T, et al *Vaccine* 2002, 20(13-14): 1797-802; Tiniakov R L, et al. *J Appl Physiol* 2003, 94(5): 1821-8). Testing can be conducted in mouse, guinea pig, dog or human in response to intranasal challenge with one or more irritants such as cold air, capsaicin, bradykinin, histamine, pollens, dextran sulfate, 2,4-tolylene diisocyanate, Bordetella bronchiseptica, Pasteurella multodica or acetic acid. In some cases, animals can be sensitized by pre-exposure to certain agents including, but not limited to, ragweed or ovalbumin. Prior to or following irritant administration, the test subject can receive, respectively, the prophylactic or therapeutic administration one or more times of compounds of the formula (I), or vehicle control, by the enteral or parenteral route. Significant differences indicative of nasal rhinitis or sensitization for the test compound-treated subjects compared with vehicle-treated subjects can be taken as evidence of anti-rhinitis activity. Independent variables include dose, frequency and route of administration, time interval between prophylactic or therapeutic test compound administration and irritant challenge as well as sex and non-sex genotype of the test subject. The intimate role of neurogenic inflammation in these hypersensitivity states demonstrates that compounds of the formula (I) desensitize or block the sensitization underlying these disease states.

Example 14

Conflict-Induced Models of Anxiety, Panic Disorder and Other Non-adaptive Stressful or Phobic Responses Compounds of the formula (I) can be tested in animal models of anxiety, panic disorders and other non-adaptive responses, according to previously documented and validated methods, such as those described by Cryan and Holmes (Cryan J F, Holmes A. *Nat Rev Drug Discov* 2005, 4(9): 775-90) or Braw et. al. (Y. Braw et al. *Behav Brain Res* 2006, 167: 261-269). Specifically, for studies in rats, the following apparati may be utilized: an open-field arena (62 cm×62 cm) enclosed by opaque walls (30 cm high) and plus-maze consists of two open arms, 50 cm×10 cm, and two enclosed arms, 50 cm×10 cm×40 cm with an open roof, arranged such that the two arms of each type are opposite each other. The maze is elevated to a height of 70 cm. The walls of the enclosed arms are made from black Plexiglas, while the floors from white Plexiglas. Videotape recordings can be analyzed using the 'Observer' system (Noldus Information Technology). A subject rat can be removed from its home cage, weighed and placed gently in the center of the open-field arena. The rat can be allowed to explore the open-field freely while its behavior is videotaped for 5 min. Afterwards, it can be transferred to the plus-maze and placed at the center, facing a closed arm. The rat's behavior can again be videotaped for 5 min, after which it can be returned to its home cage. The apparatus can cleaned using a 70% ethanol solution between rats.

Open-field and plus-maze measures can be grouped into two behavioral classes, namely 'anxiety-like behaviors' and 'activity'. Open-field behavioral measures may include 1) Anxiety measures: % time in center square, % number of entries to center square (from total squares entered), % time freezing, latency to first freezing (freezing is scored when the subject is in an immobile state for at least 3 seconds; and 2) Activity measures: Total squares entered, number of rearings (standing on two hind legs), latency for first rearing. Plus-maze measures may include 1) Anxiety: % time in open arms, % number of entries to open arms (from total entries), number of unprotected head dips, latency to enter open arm; and 2) Activity: Total entries to all arms. Anxiety-like behaviors and activity can be analyzed by one-way ANOVA's on each of the measures, for each the between-subject comparisons. Plus-maze analyses can be conducted in a similar fashion.

Testing may also be conducted in mouse or rat in this fashion in order to measure avoidance of other aversive environmental stimuli such as Geller or Vogel anticonflict tests, the light/dark test and the hole-board test (see Cryan J F, Holmes A. *Nat Rev Drug Discov* 2005, 4(9): 775-90). Prior to environmental exposure, the test subject can receive the prophylactic administration one or more times of compounds of the formula (I), or vehicle control (e.g. 10% Solutol in sterile water), by the enteral or parenteral route. The cumulative time or number of times spent engaged in the aversive behavior can be measured. Significant differences in one or more of these measures for the test compound-treated subjects compared with vehicle-treated subjects can be taken as evidence of anxiolytic activity. Because these models are pharmacologically validated by the effectiveness of clinically useful anxiolytics (Cryan J F, Holmes A. *Nat Rev Drug Discov* 2005, 4(9): 775-90), they will be useful for the detection of anxiolytic compounds of the formula (I).

Example 15

Bladder Pressure- and Hypertrophy-induced Models of Urinary Incontinence

Compounds of the formula (I) can be tested in animal models of urinary incontinence according to previously documented and validated methods, such as those described by in the scientific literature (Kaiser S, Plath T, (Metagen Pharmaceuticals GmbH, Germany DE Patent 10215321; McMurray G, et al. *Br J Pharmacol* 2006, 147 Suppl 2: S62-79). TRPM8 is expressed in human prostate, testicle, seminiferous tubules, scrotal skin and inflamed bladder (Stein R J, et al. *J Urol* 2004, 172(3): 1175-8; Stein R J, et al. *J Urol* 2004, 172(3): 1175-8; Mukerji et al. *BMC Urology* 2006, 6:6). Excitation of TRPM8 receptors through cooling or application of menthol causes contraction in the bladder and a decrease in micturation threshold volume (Tsukimi Y, Mizuyachi K, et al. *Urology* 2005, 65(2): 406-10). To assess compounds of the formula (I) for potential urinary incontinence activity, Sprague-Dawley rats are surgically implanted with bladder catheters allowing for the delivery of fluid (typically saline) and the monitoring of pressure (using a pressure transducer). Cystometry recordings can be monitored with a polygraph to evaluate voiding interval, threshold pressure, bladder capacity, bladder compliance, and the number of spontaneous bladder contractions. For example, the bladder catheter can be connected to a Harvard infusion pump, and bladders perfused overnight with saline at 2 mL/h The next morning the bladder catheter can be attached (using a "T" connector) to a Statham pressure transducer (Model P23 Db) and to a Harvard infusion pump. A plastic beaker attached to a force displacement transducer (Grass FTO3) can be placed under the rat's cage to collect and record urine volume. The cystometric evaluation of bladder function can be started by infusing saline (20 mL/h) and after the first micturition the infusion is maintained for 20 min. Two hours after the first cystometry period, the rats can be dosed orally with compounds of the formula (I) and a second cystometry is performed between 30 min and 4 h after administration of test compound. The appropriate vehicle (e.g. 10% Solutol in sterile water) can be similarly administered to groups of rats that served as controls and the cystometry can be performed at the same respective time points.

Compounds of the formula (I) can also be evaluated under conditions of bladder hypertrophy and instability. Under anesthesia, a silk ligature is tied around the proximal urethra of rodents producing a partial outlet obstruction and subsequent hypertrophied bladder development within 6-9 weeks (Woods M. et al., *J Urology* 2001, 166:1142-47). Cystometry recordings can then be evaluated as described above. Such preclinical procedures are sensitive to compounds having clinical utility for the treatment of urinary incontinence (Soulard C, et al. *J Pharmacol Exp Ther* 1992, 260(3): 1152-8), and the activity of compounds of the formula (I) in this model would be predictive of clinical utility.

Example 16

In Vivo Model for Cold-enhanced Central Pain States

Injury to the brain or spinal cord, such as that caused by trauma, interrupted Blood flow or neurodegenerative diseases, often precipitates a central pain condition. Examples of such injuries characterized, in part by, a hypersensitivity to cold stimuli include multiple sclerosis (Morin C, et al. *Clin J Pain* 2002, 18(3): 191-5; Svendsen K B, et al. *Pain* 2005, 114(3): 473-81), stroke or cerebral ischemia (Greenspan J D, et al. *Pain.* 2004, 109(3): 357-66) and spinal cord injury (Defrin R, Ohry A, Blumen N, Urca G. *Pain* 2001, 89(2-3): 253-63; Defrin R, et al. *Brain* 2002, 125(Pt 3): 501-10; Finnerup N B, et al. *Anesthesiology* 2005, 102(5): 1023-30). Each of these conditions may be readily modeled in animals for assessment of the ability of compounds of the formula (I) to mollify the hypersensitive state. For example, a spinal cord injury (SCI) can be performed in adult Sprague-Dawley rats having a body weight of 150-200 g at time of surgery (Erichsen et al. *Pain* 2005, 116: 347-358). The rats can be anaesthetized with chloral hydrate (300 mg/kg, i.p., Sigma, USA) and a catheter can be inserted into the jugular vein. A midline skin incision can then be made along the back to expose the T11-L2 vertebrae. The animals can be positioned beneath a tunable argon ion laser (Innova model 70, Coherent Laser Products Division, CA, USA) operating at a wavelength of 514 nm with an average power of 0.17 W. The laser light can be focused into a thin beam covering the single T13 vertebra, which can be irradiated for 10 min. Immediately before the irradiation, erythrosin B (Aldrich, 32.5 mg/kg dissolved in 0.9% saline) can be injected intravenously via the jugular catheter. Due to rapid metabolism of erythrosin B, the injection can be repeated after 5 min in order to maintain adequate blood concentrations. During irradiation, the body core temperature can be maintained at 37-38° C. by a heating pad. After irradiation the wound can be closed in layers and the skin sutured together.

SCI rats can be routinely tested for the presence of pain-like behaviors from 3-4 weeks after surgery. The fur of the animals can be shaved at least a day prior to examination of the cutaneous pain threshold to avoid sensitization of the skin receptors. During testing, the rats can be gently held in a standing position by the experimenter and the flank area and hindlimbs can be examined for hypersensitivity to sensory stimulation. On the day of drug testing, SCI rats can be administered drug according to the experimental schedule and the time course of pain-like behaviors can be measured. To test for the presence of cold allodynia, ethyl chloride or acetone can be sprayed onto the skin of the animals, often that which has been previously determined to be sensitive to mechanical stimulation by von Frey filament testing. The subsequent response to cold stimulation can be observed and classified according to the following scale: 0, no visible response; 1, localized response (skin twitch) without vocalization; 2, transient vocalization; 3, sustained vocalization. Kruskal Wallis ANOVA on ranks can be used to analyze the overall effects of non-parametric data obtained in response to cold stimulation following pretreatment with either compounds of the formula (I) or vehicle.

Example 17

In vivo Model for Post-anesthetic Shivering

Spontaneous post-anesthetic tremor that resembles shivering is common during recovery from anesthesia. Risks to postoperative patients include an increase in metabolic rate of up to 400%, hypoxemia, wound dehiscence, dental damage, and disruption of delicate surgical repairs. The etiology of spontaneous post-anesthetic tremor is most commonly attributed to normal thermoregulatory shivering in response to intraoperative hypothermia. In most operating and recovery rooms, shivering is controlled by the use of humidifiers, warming blankets, and inhalation of humidified heated oxygen. However, pharmacological control is an effective alternate treatment modality (Bhatnagar S, et al. *Anaesth Intensive Care* 2001, 29(2): 149-54; Tsai Y C, Chu K S. *Anesth Analg* 2001, 93(5): 1288-92). Compounds of the formula (I) may be assessed for their ability to mitigate post-ansethetic induced-shaking by using animal models such as that described by Nikki et al (Nikki P, Tammisto T. *Acta Anaesthesiol Scand* 1968, 12(3): 125-34) and Grahn (Grahn, D A, et al. *J Applied Physiology* 1996, 81: 2547-2554). For example, Wistar rats (males, weighing 250-450 g) may be surgically implanted with an EEG/EMG recording array to assess post anesthetic tremor activity. The EEG electrodes are located bilaterally 2 mm off midline and adjacent to bregma and lamda. Following a one-week recovery period, frontal-occipital EEG, raw EMG, and integrated EMG activities, as well as three temperatures (skin, rectal, and water blanket temperatures during anesthesia), and ambient temperature post-anesthesia can be monitored throughout the experiment using copper-constantin thermocouples. The EEG and EMG signals can be recorded on polygraph paper (5 mm/s, Grass model 7E polygraph) and, during recovery from anesthesia, the EEG is computer scored in 10 second epochs as either synchronized: high amplitude (0.100 µV), low frequency (1-4 Hz dominated) activity characteristic of slow-wave sleep (SWS-like) or desynchronized: low amplitude (75 µV), high frequency (5-15 Hz dominated), characteristic of waking and rapid-eye-movement sleep (W-like). The EMG activity can be quantified as the averaged summed voltage/time interval by processing the raw EMG signal through an integrator (Grass model 7P3, 0.5 s time constant). On the day of an experiment, the animal can be placed in a small acrylic box (15×15×15 cm) and exposed to a halothane vapor-air mixture (4% halothane). Immediately after the induction of anesthesia, the animal can be removed from the enclosure and subsequently anesthetized through a nose cone. Following cessation of anesthesia, two stages of recovery can be judged: emergence from anesthesia and restoration of behavioral activity (behavioral recovery). Emergence from anesthesia may be defined as an increase in tonic EMG activity and a change in the EEG from a SWS-like pattern to a W-like pattern. Behaviorally, recovery has occurred when the animal rises from a prone position and initiated coordinated movements. The time intervals from termination of anesthesia to emergence and behavioral recovery can be measured in all animals. Time interval data can be subjected to a repeated measure analysis of variance, and the Scheffe's method can be employed for testing differences between pairs of means.

Example 18

Cold-evoked Cardiovascular Pressor Responses

Compounds of the formula (I) can be tested in animals and humans for their ability to mitigate cardiovascular pressor responses evoked by cold exposure. Seasonal environmental cooling is directly associated with elevated blood pressure and an increased incidence of coronary events in human populations worldwide (Barnett, A G et al. *J Epidemiol Community Heath* 2005, 59 551-557). Cold-evoked pulmonary hypertention and cold aggravation of chronic obstructive pulmonary disease are clinical indications succeptible to heightened cardiopulmonary sensitivity to cold (Marno P et al. *Eur Respiratory Review* 2006, 15 (101): 185; Acikel M et al *Int J of Cardiol* (2004) 97: 187-192). The clinical cold pressor test assesses changes in blood pressure (BP) and cold pain perception during a 2-3 minute immersion of one hand into ice water. This test may be utilized to characterize analgesic compounds (Koltzenberg M et al. *Pain* 2006, 126(1-3): 165-74) and to assess cold hypersensitivity (Desmeules J A et al. *Arthritis Rheum* 2003, 48(5): 1420-9). Compounds of the formula (I) can be studied in an anesthetized rat cold pressor paradigm to determine whether TRPM8 antagonism would interfere with the blood pressure pressor response to cold stimulation of the forepaws. Male Sprague-Dawley rats (300-450 g) anesthetized with sodium pentobarbital are instrumented with a jugular catheter and an indwelling carotid artery cannula connected to a pressure transducer. Vehicle (e.g. 20% HPbCD in sterile water) or test compound is infused (1 mL/kg) over one minute through the intravenous catheter. Ten minutes later both forelimbs are packed in crushed ice for 5 minutes. Alternatively, the test compound and vehicle treatments may be administered orally at an appropriated time prior to the surgical cannulations and cold challenge. Percent changes in mean arterial pressure in response to this cold stimulus are calculated for vehicle and test compound pretreatments. Percent inhibition attributed to treatment with test compound is then determined using the following formula: % Inhibition=[1−(cold evoked % change in BP post-test compound/cold evoked % change in BP post-vehicle)]×100. Results are shown in Table 11

Example 19

Cold-induced Vasoconstriction: Ramifications for Tissue Perfusion

Damage may occur to a bodily tissue when blood flow is compromised or interrupted. Reasons for vascular compromise include peripheral vascular disease (Lamah M et al, European journal of vascular and endovascular surgery (1999), 18(1), 48-51), prior traumatic or frostbite injury, Raynaud's syndrome (Lutolf, O et al Microvascular research (1993), 46(3), 374-82), diabetic neuropathy (Forst T et al, Clinical science (London, England: 1979) (1998), 94(3), 255-61.), surgical intervention and autonomic dysregulation (Gherghel D et al, Investigative ophthalmology & visual science (2004), 45(10), 3546-54). In the case of marginal resting perfusion, vasoconstriction as enchanced by cool temperature may aggravate symptoms and potentiate tissue injury (Cankar K et al, The Journal of hand surgery (2000), 25(3), 552-8; Lutolf O et al Microvascular research (1993), 46(3), 374-82.). Several of these conditions may be readily modeled in animals to assess of the ability of TRPM8 antagonists such as compounds of the formula (I) to preserve tissue perfusion in the face of local cooling. For example, laser Doppler assessment of skin blood flow may be studied in the paws of anesthetized rats (Hord A H et al, Anesthesia and analgesia (1999), 88(1), 103-8), wherein the paw is subject to a series of decreasing temperatures steps as applied by physical contact with a Peltier cooling element under computer control. The laser Doppler measures skin perfusion in the face of cooling-induced vasoconstriction thereby generating a temperature x perfusion relationship. Systemic administratin of a TRPM8 antagonist is anticipated to shift this curve toward preserving perfusion at reduced temperatures relative to vehicle pretreatment. This activity is envisioned to be therapeutic in protecting tissue from hypo-perfusion and ischemia thereby minimizing the associated symptoms (e.g. pain) and potential tissue damage.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

I claim:
1. A compound of Formula (I)

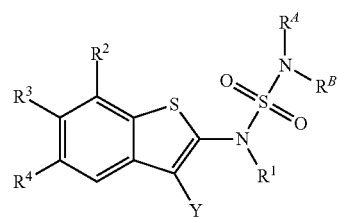

wherein
Y is
   (i) H;
   (ii) bromo;
   (iii) chloro;
   (iv) fluoro;
   (v) iodo;
   (vi) $C_{3-6}$ cycloalkyl; or
   (vii) $C_{1-6}$ alkyl;
$R^1$ is
   (i) $C_{3-6}$ cycloalkyl;
   (ii) $C_{1-6}$ alkyl substituted with one $C_{6-10}$ aryl group and optionally one additional substituent selected from the group consisting of hydroxy and oxo, wherein said $C_{6-10}$ aryl group is optionally substituted with 1 to 3 substituents independently selected from the group consisting of chloro, fluoro, bromo, $C_{1-4}$ alkyl, $C_{1-4}$ alkoxy optionally substituted with 1 to 3 fluoro substituents, hydroxy, $C_{1-4}$ alkoxycarbonyl, $C_{1-3}$ alkylthio, trifluoromethylthio, cyano, trifluoromethyl, aminocarbonyl, $C_{1-3}$ alkylaminocarbonyl, di($C_{1-3}$) alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, and $C_{1-3}$ alkylcarbonyl; with the proviso that not more than two of the substituents are selected from the group consisting of $C_{1-4}$ alkoxy substituted with 1 to 3 fluoro substituents, $C_{1-4}$ alkoxycarbonyl, $C_{1-3}$ alkylthio, trifluoromethylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, and $C_{1-3}$ alkylcarbonyl;
   (iii) $C_{1-6}$ alkyl substituted with phenyl, wherein phenyl is substituted with 4 or 5 fluoro substituents; or phenyl is substituted with methoxy and 3 to 4 fluoro substituents;
   (iv) $C_{1-6}$ alkyl optionally substituted with $C_{3-6}$ cycloalkyl or trifluoromethyl; or
   (v) methylene substituted with benzo[1,3]dioxol-5-yl, 2,2-difluoro-benzo[1,3]dioxol-5-yl, or 2,3-dihydro-benzo[1,4]dioxin-6-yl;
$R^2$ is
   (i) hydrogen,
   (ii) fluoro,
   (iii) chloro,
   (iv) methoxy, or
   (v) methyl;
$R^3$ is
   (i) hydrogen,
   (ii) fluoro, (iii) chloro, or
(iv) methyl;

$R^4$ is
(i) hydrogen,
(ii) $C_{1-6}$ alkyl,
(iii) trifluoromethyl,
(iv) $C_{1-4}$ alkoxy,
(v) bromo,
(vi) chloro,
(vii) fluoro, or
(viii) hydroxy;

$R^A$ is $C_{1-6}$alkyl substituted at a terminal carbon atom with a substituent selected from the group consisting of carboxy, $C_{1-4}$alkoxycarbonyl, $C_{1-3}$alkoxy, and hydroxy;

$R^B$ is hydrogen or $C_{1-6}$alkyl;

or, $R^A$ and $R^B$ are taken together with the nitrogen atom to which they are attached to form a 6 membered ring containing one heteroatom selected from the group consisting of O, S, and $S(O_2)$;

or, $R^A$ and $R^B$ are taken together with the nitrogen atom to which they are attached to form a 5 or 6 membered ring, optionally containing one additional N atom, to form
 (i) piperizin-1-yl wherein the piperizinyl nitrogen is substituted with $R^C$;
 (ii) pyrrolidin-1-yl optionally substituted at the 3-position with $NR^D R^E$; wherein $R^D$ and $R^E$ are independently selected from the group consisting of hydrogen and $C_{1-4}$alkyl; or, $R^D$ and $R^E$ are taken together with the nitrogen atom to which they are both attached to form a 5 or 6 membered ring; or
 (iii) piperidin-1-yl optionally substituted with carboxy; $C_{1-3}$alkoxycarbonyl; or $C_{1-4}$alkyl substituted at a terminal carbon atom with a substituent selected from the group consisting of carboxy, $C_{1-3}$alkoxy, and hydroxy;
  or piperidinyl is optionally substituted at the 4-position with
   (i) $C(O)NR^Y R^Z$; wherein $R^Y$ is hydrogen or $C_{1-6}$alkyl; and $R^Z$ is hydrogen or $C_{1-6}$alkyl optionally substituted with amino, $C_{1-2}$alkylamino, or di($C_{1-2}$alkyl) amino; or, $R^Y$ and $R^Z$ are taken together with the nitrogen atom to which they are both attached to form a 5 or 6 membered ring, and said 6 membered ring is optionally containing O or 4-N(methyl);
   (ii) $NR^H R^J$; wherein $R^H$ and $R^J$ are independently selected from the group consisting of hydrogen and $C_{1-4}$alkyl; or, $R^H$ and $R^J$ are taken together with the nitrogen atom to which they are both attached to form a 5 or 6 membered ring; or
   (iii) a spirofused pyrrolidinyl ring bound via a carbon atom of said ring, wherein the pyrrolidinyl nitrogen atom is optionally substituted with $C_{1-4}$alkyl, $C_{3-6}$cycloalkyl($C_{1-3}$)alkyl, or $CH_2CF_3$;
  and wherein a piperidinyl ring is optionally benzofused to form a 1,2,3,4-tetrahydro-isoquinolin-1-yl, wherein said 1,2,3,4-tetrahydro-isoquinolin-1-yl is optionally substituted on the heterocyclyl portion of said ring with one to two substituents independently selected from the group consisting of methyl and fluoro;
  or, the heterocyclyl portion of said 1,2,3,4-tetrahydro-isoquinolin-1-yl is unsubstituted and the benzo portion of said ring is optionally substituted with one to two substituents independently selected from the group consisting of fluoro, chloro, bromo, iodo, methyl, trifluoromethyl, cyano, ethoxycarbonyl, carboxy, and methoxy; provided that no more than one of the substituents is carboxy or ethoxycarbonyl;

$R^C$ is
 (i) $C(O)R^{1a}$, wherein $R^{1a}$ is $C_{1-6}$alkyl, $C_{3-6}$cycloalkyl, or phenyl; or
 (ii) $SO_2R^{2a}$, wherein $R^{2a}$ is methyl or phenyl;
and enantiomers, diastereomers, and pharmaceutically acceptable salts thereof.

2. A compound of Formula (I)

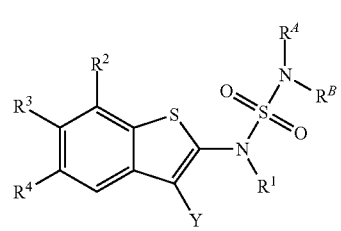

wherein
Y is hydrogen; bromo; chloro; fluoro; iodo; $C_{3-6}$ cycloalkyl; or $C_{1-4}$ alkyl;

$R^1$ is
(i) $C_{3-6}$ cycloalkyl;
(ii) $C_{1-6}$ alkyl substituted with one $C_{6-10}$ aryl group, wherein said $C_{6-10}$ aryl group is optionally substituted with 1 to 3 substituents independently selected from the group consisting of chloro, fluoro, bromo, $C_{1-4}$ alkyl, $C_{1-4}$ alkoxy, hydroxy, $C_{1-4}$ alkoxycarbonyl, $C_{1-3}$ alkylthio, trifluoromethylthio, cyano, trifluoromethyl, $C_{1-3}$ alkylsulfonyl optionally substituted with 1 to 3 fluoro substituents, nitro, and $C_{1-3}$ alkylcarbonyl; with the proviso that not more than two of the substituents are selected from the group consisting of $C_{1-4}$ alkoxy, $C_{1-4}$ alkoxycarbonyl, $C_{1-3}$ alkylthio, trifluoromethylthio, cyano, trifluoromethyl, $C_{1-3}$ alkylsulfonyl, nitro, and $C_{1-3}$ alkylcarbonyl;
(iii) $C_{1-6}$ alkyl substituted with phenyl, wherein phenyl is substituted with 4 or 5 fluoro substituents; or phenyl is substituted with methoxy and 3 to 4 fluoro substituents;
(iv) $C_{1-6}$alkyl optionally substituted with $C_{3-6}$cycloalkyl or trifluoromethyl; or
(v) methylene substituted with benzo[1,3]dioxol-5-yl, 2,2-difluoro-benzo[1,3]dioxol-5-yl, or 2,3-dihydro-benzo[1,4]dioxin-6-yl;

$R^2$ is
(i) hydrogen or
(ii) fluoro;

$R^3$ is
(i) hydrogen or
(ii) fluoro;

$R^4$ is
(i) hydrogen;
(ii) methyl; or
(iii) fluoro;

$R^A$ is $C_{1-4}$alkyl substituted at a terminal carbon atom with a substituent selected from the group consisting of carboxy, $C_{1-3}$alkoxy, and hydroxy;

$R^B$ is hydrogen or $C_{1-4}$alkyl;

or, $R^A$ and $R^B$ are taken together with the nitrogen atom to which they are attached to form a 6 membered ring containing one additional heteroatom selected from the group consisting of O, S, and $S(O_2)$;

or, $R^A$ and $R^B$ are taken together with the nitrogen atom to which they are attached to form a 5 or 6 membered ring, optionally containing one additional N atom, to form
  (i) piperizin-1-yl wherein the piperizinyl nitrogen is substituted with $R^C$;
  (ii) pyrrolidin-1-yl optionally substituted at the 3-position with $C_{1-4}$alkyl or $NR^DR^E$; wherein $R^D$ and $R^E$ are independently selected from the group consisting of hydrogen and $C_{1-4}$alkyl; or, $R^D$ and $R^E$ are taken together with the nitrogen atom to which they are both attached to form a 5 or 6 membered ring; and
  (iii) piperidin-1-yl optionally substituted with carboxy; $C_{1-3}$alkoxycarbonyl; or $C_{1-4}$alkyl substituted at a terminal carbon atom with a substituent selected from the group consisting of carboxy, $C_{1-3}$alkoxy, and hydroxy;
  or piperidinyl is optionally substituted at the 4-position with
    (i) $C(O)NR^YR^Z$; wherein $R^Y$ is hydrogen or $C_{1-6}$alkyl; and $R^Z$ is hydrogen or $C_{1-6}$alkyl optionally substituted with amino, $C_{1-2}$alkylamino, or di($C_{1-2}$alkyl)amino; or, $R^Y$ and $R^Z$ are taken together with the nitrogen atom to which they are both attached to form a 5 or 6 membered ring, and said 6 membered ring is optionally containing O or 4-N(methyl); or
    (ii) $NR^HR^J$; wherein $R^H$ and $R^J$ are independently selected from the group consisting of hydrogen and $C_{1-4}$alkyl; or, $R^H$ and $R^J$ are taken together with the nitrogen atom to which they are both attached to form a 5 or 6 membered ring;
$R^C$ is
  (i) hydrogen;
  (ii) $C_{1-8}$ alkyl;
  (iii) $C_{3-6}$cycloalkyl;
  (iv) $C_{3-6}$cycloalkyl($C_{1-4}$)alkyl;
  (v) $CH_2CF_3$; or
  (vi) phenyl optionally independently substituted with one to two substituents selected from the group consisting of methyl, methoxy, chloro, fluoro, and trifluoromethyl;
and enantiomers, diastereomers, and pharmaceutically acceptable salts thereof.

3. A compound of Formula (I)

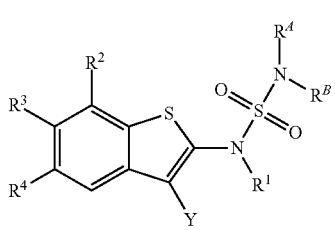

(I)

wherein
Y is hydrogen; methyl; isopropyl; chloro; cyclopropyl; cyclobutyl; or cyclopentyl; bromo;
$R^1$ is
  (i) $C_{1-6}$ alkyl substituted with one $C_{6-10}$ aryl group, wherein said $C_{6-10}$ aryl group is optionally substituted with 1 to 3 substituents independently selected from the group consisting of chloro, fluoro, bromo, $C_{1-4}$ alkyl, $C_{1-4}$ alkoxy, hydroxy, $C_{1-4}$ alkylthio, trifluoromethylthio, cyano, trifluoromethyl, and $C_{1-3}$ alkylcarbonyl; with the proviso that not more than two of the substituents are selected from the group consisting of $C_{1-4}$ alkoxy, $C_{1-3}$ alkylthio, trifluoromethylthio, cyano, trifluoromethyl, and $C_{1-3}$ alkylcarbonyl;
  (ii) $C_{1-3}$ alkyl substituted with phenyl, wherein phenyl is substituted with 4 or 5 fluoro substituents; or phenyl is substituted with methoxy and 3 to 4 fluoro substituents;
  (iii) $C_{1-3}$alkyl optionally substituted with cyclopropyl or trifluoromethyl; or
  (iv) methylene substituted with benzo[1,3]dioxol-5-yl, 2,2-difluoro-benzo[1,3]dioxol-5-yl, or 2,3-dihydro-benzo[1,4]dioxin-6-yl;
$R^2$ is
  (i) hydrogen or
  (ii) fluoro;
$R^3$ is
  (i) hydrogen or
  (ii) fluoro;
$R^4$ is
  (i) hydrogen;
  (ii) methyl; or
  (iii) fluoro;
$R^A$ is $C_{1-4}$alkyl substituted at a terminal carbon atom with a substituent selected from the group consisting of carboxy, $C_{1-3}$alkoxy, and hydroxy;
$R^B$ is hydrogen or $C_{1-4}$alkyl;
or, $R^A$ and $R^B$ are taken together with the nitrogen atom to which they are attached to form a 6 membered ring containing one heteroatom selected from the group consisting of O, S, and $S(O_2)$;
or, $R^A$ and $R^B$ are taken together with the nitrogen atom to which they are attached to form a 5 or 6 membered ring, optionally containing one additional N atom, selected from the group consisting of
  (i) piperizin-1-yl wherein the piperizinyl nitrogen is substituted with $R^C$;
  (ii) pyrrolidin-1-yl optionally substituted at the 3-position with $C_{1-4}$alkyl or $NR^DR^E$; wherein $R^D$ and $R^E$ are independently selected from the group consisting of hydrogen and $C_{1-4}$alkyl; or, $R^D$ and $R^E$ are taken together with the nitrogen atom to which they are both attached to form a 5 or 6 membered ring; and
  (iii) piperidin-1-yl optionally substituted with carboxy; $C_{1-3}$alkoxycarbonyl; or $C_{1-4}$alkyl substituted at a terminal carbon atom with a substituent selected from the group consisting of carboxy, $C_{1-3}$alkoxy, and hydroxy;
  or piperidinyl is optionally substituted at the 4-position with
    (i) $C(O)NR^YR^Z$; wherein hydrogen or $C_{1-6}$alkyl; and $R^Z$ is hydrogen or $C_{1-6}$alkyl optionally substituted with amino, $C_{1-2}$alkylamino, or di($C_{1-2}$alkyl)amino; or, $R^Y$ and $R^Z$ are taken together with the nitrogen atom to which they are both attached to form a 5 or 6 membered ring, and said 6 membered ring is optionally containing O or 4-N(methyl); or
    (ii) $NR^HR^J$; wherein $R^H$ and $R^J$ are independently selected from the group consisting of hydrogen and $C_{1-4}$alkyl; or, $R^H$ and $R^J$ are taken together with the nitrogen atom to which they are both attached to form a 5 or 6 membered ring;
$R^C$ is
  (i) hydrogen;
  (ii) $C_{1-8}$ alkyl;
  (iii) $C_{3-6}$cycloalkyl;
  (iv) $C_{3-6}$cycloalkyl($C_{1-4}$)alkyl;
  (v) $CH_2CF_3$; or (vi) phenyl optionally independently substituted with one to two substituents selected from the group consisting of methyl, methoxy, chloro, fluoro, and trifluoromethyl;

and enantiomers, diastereomers, and pharmaceutically acceptable salts thereof.

4. A compound of Formula (I)

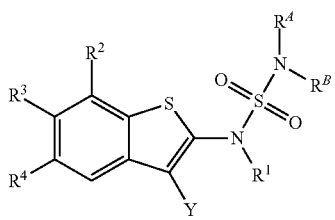

wherein

Y is hydrogen; methyl; isopropyl; chloro; cyclopropyl; or bromo;

$R^1$ is
  (i) $C_{1-6}$ alkyl substituted with one $C_{6-10}$ aryl group, wherein said $C_{6-10}$ aryl group is optionally substituted with 1 to 3 substituents independently selected from the group consisting of chloro, fluoro, bromo, $C_{1-4}$ alkyl, $C_{1-4}$ alkoxy, hydroxy, $C_{1-3}$ alkylthio, trifluoromethylthio, cyano, trifluoromethyl, and $C_{1-3}$ alkylcarbonyl; with the proviso that not more than two of the substituents are selected from the group consisting of $C_{1-4}$ alkoxy, $C_{1-3}$ alkylthio, trifluoromethylthio, cyano, trifluoromethyl, and $C_{1-3}$ alkylcarbonyl;
  (ii) $C_{1-3}$ alkyl substituted with phenyl, wherein phenyl is substituted with 4 or 5 fluoro substituents; or phenyl is substituted with methoxy and 3 to 4 fluoro substituents; o
  (iii) $C_{1-3}$ alkyl optionally substituted with cyclopropyl or trifluoromethyl; or
  (iv) methylene substituted with benzo[1,3]dioxol-5-yl, 2,2-difluoro-benzo[1,3]dioxol-5-yl, or 2,3-dihydro-benzo[1,4]dioxin-6-yl;

$R^2$ is
  (i) hydrogen or
  (ii) fluoro;

$R^3$ is
  (i) hydrogen or
  (ii) fluoro;

$R^4$ is
  (i) hydrogen;
  (ii) methyl; or
  (iii) fluoro;

$R^A$ is $C_{1-4}$alkyl substituted at a terminal carbon atom with a substituent selected from the group consisting of carboxy, $C_{1-3}$alkoxy, and hydroxy;

$R^B$ is hydrogen or $C_{1-4}$alkyl;

or, $R^A$ and $R^B$ are taken together with the nitrogen atom to which they are attached to form a 6 membered ring containing one heteroatom selected from the group consisting of O, S, and $S(O_2)$;

or, $R^A$ and $R^B$ are taken together with the nitrogen atom to which they are attached to form a 5 or 6 membered ring, optionally containing one additional N atom, selected from the group consisting of
  (i) piperizin-1-yl wherein the piperizinyl nitrogen is substituted with $R^C$;
  (ii) pyrrolidin-1-yl optionally substituted at the 3-position with $C_{1-4}$alkyl or $NR^DR^E$; wherein $R^D$ and $R^E$ are independently selected from the group consisting of hydrogen and $C_{1-4}$alkyl; or, $R^D$ and $R^E$ are taken together with the nitrogen atom to which they are both attached to form a 5 or 6 membered ring; and
  (iii) piperidin-1-yl optionally substituted with carboxy; $C_{1-3}$alkoxycarbonyl; or $C_{1-4}$alkyl substituted at a terminal carbon atom with a substituent selected from the group consisting of carboxy, $C_{1-3}$alkoxy, and hydroxy;
    or piperidinyl is optionally substituted at the 4-position with
    (i) $C(O)NR^YR^Z$; wherein $R^Y$ is hydrogen or $C_{1-6}$alkyl; and $R^Z$ is hydrogen or $C_{1-6}$alkyl optionally substituted with amino, $C_{1-2}$alkylamino, or di($C_{1-2}$alkyl)amino; or, $R^Y$ and $R^Z$ are taken together with the nitrogen atom to which they are both attached to form a 5 or 6 membered ring, and said 6 membered ring is optionally containing O or 4-N(methyl); or
    (ii) $NR^HR^J$; wherein $R^H$ and $R^J$ are independently selected from the group consisting of hydrogen and $C_{1-4}$alkyl; or, $R^H$ and $R^J$ are taken together with the nitrogen atom to which they are both attached to form a 5 or 6 membered ring;

$R^C$ is
  (i) hydrogen;
  (ii) $C_{1-8}$ alkyl;
  (iii) $C_{3-6}$cycloalkyl;
  (iv) $C_{3-6}$cycloalkyl($C_{1-4}$)alkyl;
  (v) $CH_2CF_3$; or
  (vi) phenyl optionally independently substituted with one to two substituents selected from the group consisting of methyl, methoxy, chloro, fluoro, and trifluoromethyl;

and enantiomers, diastereomers, and pharmaceutically acceptable salts thereof.

5. A compound of Formula (I)

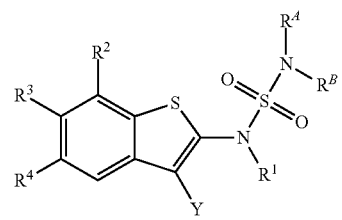

selected from the group consisting of a compound wherein Y is bromo, $R^1$ is 4-fluoro-3-trifluoromethylphenylmethyl, $R^2$, $R^3$, and $R^4$ are H, $R^A$ is H, and $R^B$ is carboxymethyl;

a compound wherein Y is bromo, $R^1$ is 4-fluoro-3-trifluoromethylphenylmethyl, $R^2$, $R^3$, and $R^4$ are H, $R^A$ is H, and $R^B$ is 3-carboxypropyl;

a compound wherein Y is methyl, $R^1$ is 4-fluoro-3-trifluoromethylphenylmethyl, $R^2$, $R^3$, and $R^4$ are H, $R^A$ is H, and $R^B$ is 3-carboxypropyl;

a compound wherein Y is bromo, $R^1$ is 4-fluoro-3-trifluoromethylphenylmethyl, $R^2$, $R^3$, and $R^4$ are H, $R^A$ is H, and $R^B$ is 4-carboxybutyl;

a compound wherein Y is methyl, $R^1$ is 4-trifluoromethoxyphenylmethyl, $R^2$, $R^3$, and $R^4$ are H, and $R^A$ and $R^B$ are taken together to form 4-methylpiperazin-1-yl;

a compound wherein Y is methyl, $R^1$ is 4-trifluoromethoxyphenylmethyl, $R^2$, $R^3$, and $R^4$ are H, and $R^A$ and $R^B$ are taken together to form 4-carboxypiperidin-1-yl;

a compound wherein Y is methyl, $R^1$ is 4-trifluoromethoxyphenylmethyl, $R^2$, $R^3$, and $R^4$ are H, and $R^A$ and $R^B$ are taken together to form 4-(4-methylpiperazin-1-ylcarbonyl)piperidin-1-yl ;

a compound wherein Y is methyl, $R^1$ is 4-trifluoromethoxyphenylmethyl, $R^2$, $R^3$, and $R^4$ are H, and $R^A$ and $R^B$ are taken together to form 4-(2-dimethylamino-ethylaminocarbonyl)piperidin-1-yl ;

a compound wherein Y is methyl, $R^1$ is 4-trifluoromethoxyphenylmethyl, $R^2$, $R^3$, and $R^4$ are H, and $R^A$ and $R^B$ are taken together to form piperazin-1-yl;

a compound wherein Y is methyl, $R^1$ is 4-trifluoromethoxyphenylmethyl, $R^2$, $R^3$, and $R^4$ are H, and $R^A$ and $R^B$ are taken together to form 4-isopropyl-piperazin-1-yl;

a compound wherein Y is methyl, $R^1$ is 4-trifluoromethoxyphenylmethyl, $R^2$, $R^3$, and $R^4$ are H, and $R^A$ and $R^B$ are taken together to form 4-(3-methyl-butyl)-piperazin-1-yl;

a compound of Formula (I) wherein Y is methyl, $R^1$ is 4-trifluoromethoxyphenylmethyl, $R^2R^3$, and $R^4$ are H, and $R^A$ and $R^B$ are taken together to form 4-(2,2,2-trifluoroethyl)-piperazin-1-yl;

a compound of Formula (I) wherein Y is methyl, $R^1$ is 4-trifluoromethoxyphenylmethyl, $R^2$, $R^3$, and $R^4$ are H, and $R^A$ and $R^B$ are taken together to form 4-(dimethylamino)piperidin-1-yl;

a compound of Formula (I) wherein Y is methyl, $R^1$ is 4-trifluoromethoxyphenylmethyl, $R^2R^3$, and $R^4$ are H, and $R^A$ and $R^B$ are taken together to form 4-(pyrrolidin-1-yl)piperidin-1-yl;

a compound of Formula (I) wherein Y is methyl, $R^1$ is 4-trifluoromethoxyphenylmethyl, $R^2R^3$, and $R^4$ are H, and $R^A$ and $R^B$ are taken together to form piperidin-1-yl;

a compound of Formula (I) wherein Y is methyl, $R^1$ is 4-trifluoromethoxyphenylmethyl, $R^2R^3$, and $R^4$ are H, and $R^A$ and $R^B$ are taken together to form morpholin-4-yl;

and enantiomers, diastereomers, and pharmaceutically acceptable salts thereof.

6. A pharmaceutical composition comprising a compound of claim 1 and at least one of a pharmaceutically acceptable carrier, a pharmaceutically acceptable excipient, and a pharmaceutically acceptable diluent.

7. A pharmaceutical composition of claim 6, wherein the composition is a solid, oral dosage form.

8. A pharmaceutical composition of claim 6, wherein the composition is a syrup, an elixir, or a suspension.

* * * * *